(12) United States Patent
Schmidt et al.

(10) Patent No.: US 9,245,337 B2
(45) Date of Patent: Jan. 26, 2016

(54) CONTEXT DRIVEN IMAGE MINING TO GENERATE IMAGE-BASED BIOMARKERS

(71) Applicant: Definiens AG, Munich (DE)

(72) Inventors: Guenter Schmidt, Munich (DE); Gerd Binnig, Kottgeisering (DE); Ralf Schoenmeyer, Gilching (DE); Arno Schaepe, Starnberg (DE)

(73) Assignee: Definiens AG, Munich (DE)

( * ) Notice: Subject to any disclaimer, the term of this patent is extended or adjusted under 35 U.S.C. 154(b) by 323 days.

(21) Appl. No.: 14/067,932

(22) Filed: Oct. 30, 2013

(65) Prior Publication Data

US 2014/0050384 A1    Feb. 20, 2014

Related U.S. Application Data

(63) Continuation of application No. 12/930,873, filed on Jan. 18, 2011, now Pat. No. 8,594,410, which is a continuation-in-part of application No. 11/511,930, filed as application No. PCT/EP2006/061498 on Apr.

(Continued)

(30) Foreign Application Priority Data

Oct. 15, 2002  (DE) ................................. 102 48 013
Apr. 8, 2005   (DE) .......................... 10 2005 016 290

(51) Int. Cl.
*G06T 7/00*  (2006.01)
*G06K 9/62*  (2006.01)

(52) U.S. Cl.
CPC ............ *G06T 7/0014* (2013.01); *G06K 9/6253* (2013.01); *G06T 7/0012* (2013.01);

(Continued)

(58) Field of Classification Search
CPC ........... G06T 2207/30004; G06T 2207/30096; G06T 2207/30061; G01N 2800/00; G01N 2800/60
USPC .......... 382/132, 128, 130, 131, 155, 158, 181
See application file for complete search history.

(56) References Cited

U.S. PATENT DOCUMENTS 4,922,432 A    5/1990   Kobayashi et al. ........... 364/490
5,170,347 A   12/1992   Tuy et al. .................. 364/413.22

(Continued)

FOREIGN PATENT DOCUMENTS

DE        19908204 A1    10/1998
WO    WO 01/45033 A2     6/2001

OTHER PUBLICATIONS

Schaepe, Urbani, Leiderer and Athelogou, "Fraktal hierarchische, prozess- und objektbasierte Bildanalyse. Anwendung in der biomedizinischen Mikroskopie," Bildverarbeitung fuer die Medizin, Mar. 9, 2003 (XP002282616) pp. 206-210.

(Continued)

*Primary Examiner* — Michael A Newman
(74) *Attorney, Agent, or Firm* — Imperium Patent Works; Darien K. Wallace

(57) ABSTRACT

An image-based biomarker is generated using image features obtained through object-oriented image analysis of medical images. The values of a first subset of image features are measured and weighted. The weighted values of the image features are summed to calculate the magnitude of a first image-based biomarker. The magnitude of the biomarker for each patient is correlated with a clinical endpoint, such as a survival time, that was observed for the patient whose medical images were analyzed. The correlation is displayed on a graphical user interface as a scatter plot. A second subset of image features is selected that belong to a second image-based biomarker such that the magnitudes of the second image-based biomarker for the patients better correlate with the clinical endpoints observed for those patients. The second biomarker can then be used to predict the clinical endpoint of other patients whose clinical endpoints have not yet been observed.

20 Claims, 41 Drawing Sheets

Related U.S. Application Data 10, 2006, now Pat. No. 7,873,223, said application No. 11/511,930 is a continuation-in-part of application No. 10/687,477, filed on Oct. 15, 2003, now Pat. No. 7,146,380.

(60) Provisional application No. 61/459,180, filed on Dec. 8, 2010.

(52) U.S. Cl.
CPC ... *G01N2800/00* (2013.01); *G06T 2207/10116* (2013.01); *G06T 2207/30004* (2013.01); *G06T 2207/30061* (2013.01); *G06T 2207/30068* (2013.01)

(56) References Cited

U.S. PATENT DOCUMENTS

| | | | |
|---|---|---|---|
| 5,297,215 A | 3/1994 | Yamagishi | 382/6 |
| 5,331,554 A | 7/1994 | Graham | 364/419.08 |
| 5,383,472 A | 1/1995 | Devlin et al. | 128/771 |
| 5,537,485 A | 7/1996 | Nishikawa et al. | 382/130 |
| 5,579,393 A | 11/1996 | Conner et al. | 380/25 |
| 5,590,218 A | 12/1996 | Ornstein | 382/157 |
| 5,870,493 A | 2/1999 | Vogl et al. | 382/195 |
| 5,872,859 A | 2/1999 | Gur et al. | 382/128 |
| 5,966,701 A | 10/1999 | Kohda et al. | 706/20 |
| 5,983,210 A | 11/1999 | Imasaki et al. | 706/15 |
| 6,018,728 A | 1/2000 | Spence et al. | 706/20 |
| 6,058,206 A | 5/2000 | Kortge | 382/159 |
| 6,058,322 A | 5/2000 | Nishikawa et al. | 600/408 |
| 6,075,878 A | 6/2000 | Yoshida et al. | 382/132 |
| 6,075,879 A | 6/2000 | Roehrig et al. | 382/132 |
| 6,246,782 B1 | 6/2001 | Shapiro et al. | 382/128 |
| 6,282,305 B1 | 8/2001 | Huo et al. | 382/128 |
| 6,320,976 B1 | 11/2001 | Murthy et al. | 382/128 |
| 6,324,532 B1 | 11/2001 | Spence et al. | 706/27 |
| 6,389,305 B1 | 5/2002 | Deban et al. | 600/427 |
| 6,453,058 B1* | 9/2002 | Murthy | G06K 9/6211 382/128 |
| 6,574,357 B2* | 6/2003 | Wang | A61B 6/465 382/132 |
| 6,625,303 B1 | 9/2003 | Young et al. | 382/132 |
| 6,650,766 B1* | 11/2003 | Rogers | B25J 15/04 128/922 |
| 6,757,665 B1 | 6/2004 | Unsworth et al. | 706/15 |
| 6,763,128 B1 | 7/2004 | Rogers et al. | 382/132 |
| 6,778,705 B2 | 8/2004 | Gutta et al. | 382/224 |
| 6,801,645 B1 | 10/2004 | Collins et al. | 382/130 |
| 6,937,776 B2 | 8/2005 | Li et al. | 382/260 |
| 6,944,603 B2 | 9/2005 | Bergan et al. | 706/45 |
| 6,970,587 B1* | 11/2005 | Rogers | G06T 7/0012 128/922 |
| 7,437,004 B2 | 10/2008 | Baatz et al. | 382/224 |
| 7,533,406 B2 | 5/2009 | Ludvig et al. | 725/110 |
| 8,060,348 B2* | 11/2011 | Cline | G06K 9/0061 382/128 |
| 8,320,655 B2* | 11/2012 | Sarachan | G06K 9/00147 382/128 |
| 8,335,360 B2* | 12/2012 | Christiansen | G01N 33/5082 382/128 |
| 2001/0031920 A1 | 10/2001 | Kaufman et al. | 600/431 |
| 2002/0030811 A1 | 3/2002 | Schindler | 356/318 |
| 2002/0041328 A1 | 4/2002 | LeCompte et al. | 348/144 |
| 2002/0188436 A1 | 12/2002 | Schmidt et al. | 704/1 |
| 2002/0191823 A1 | 12/2002 | Wehrli et al. | 382/128 |
| 2003/0016869 A1 | 1/2003 | Laumeyer et al. | 382/190 |
| 2003/0035773 A1 | 2/2003 | Sofia Totterman | 424/9.1 |
| 2003/0223627 A1 | 12/2003 | Yoshida et al. | 382/128 |
| 2004/0148296 A1 | 7/2004 | Schaepe et al. | 707/100 |
| 2006/0063190 A1* | 3/2006 | Fischer | C12Q 1/6886 435/6.14 |
| 2006/0078926 A1* | 4/2006 | Marcelpoil | C12Q 1/6886 435/6.14 |
| 2006/0277073 A1 | 12/2006 | Heilbrunn et al. | 705/3 |
| 2007/0072250 A1* | 3/2007 | Kim | G01N 33/574 435/7.23 |
| 2007/0081702 A1 | 4/2007 | Porat et al. | 382/128 |
| 2007/0094168 A1* | 4/2007 | Ayala | G06N 3/105 706/15 |
| 2007/0237373 A1 | 10/2007 | Kiraly et al. | 382/128 |
| 2008/0008349 A1 | 1/2008 | Binnig et al. | 382/100 |
| 2008/0008367 A1 | 1/2008 | Franaszek et al. | 382/128 |
| 2009/0234627 A1* | 9/2009 | Yu | A61N 5/1031 703/11 |
| 2010/0086185 A1 | 4/2010 | Weiss | 382/131 |
| 2010/0177950 A1* | 7/2010 | Donovan | G06F 19/3437 382/133 |

OTHER PUBLICATIONS

Schaepe, Urbani, Leiderer and Athelogou, "Fraktal hierarchische, prozess- und objektbasierte Bildanalyse. Anwendung in der biomedizinischen Mikroskopie," Bildverarbeitung fuer die Medizin 2003, Informatik Aktuell, Dec. 31, 2003, (XP002440467); 3 pages.

Benz, Hofmann, Willhauck, Lingenfelder and Heynen, "Multi-resolution, object-oriented fuzzy analysis of remote sensing data for GIS-ready information," ISPRS Journal of Photography & Remote Sensing, vol. 58, No. 3-4, Dec. 16, 2003; (XP002440464); pp. 239-258.

Ruan, Bürkle and Dudeck, "An object oriented design for automated navigation of semantic networks inside a medical data dictionary," Artificial Intelligence in Medicine, vol. 18, No. 1, Jan. 31, 2000 (XP002440465); pp. 83-103.

Apte, Morgenstern and Hong, "AI at IBM Research," IEEE Intelligent Systems, vol. 15, No. 6, Dec. 31, 2000 (XP002440466); pp. 51-57.

Kailash et al., "A volume decomposition approach to machining feature extraction of casting and forging components," 2001, Computer-Aided Design, pp. 605-617.

Sormaz et al., "Intelligent Process Planning Implemented as an Integrated Module of CIM," Proceedings of ASME Design Engineering Technical Conferences, 1997 pp. 1-10.

Galper et al., "Computational Simulations of Biological Systems," 1994, Academic Press, Inc., Biocomputing: Informatics and Genome Projects, pp. 269-305.

Bacus et al., "Image Morphometric Nuclear Grading of Intraepithelial Neoplastic Lesions with Applications to Cancer Chemoprevention Trials," Cancer Epidemiol. Biomarkers Prev., vol. 8 (1999) pp. 1087-1094.

Buyse et al., "Biomarkers and surrogate end points—the challenge of statistical validation," Nat. Rev. Clin. Oncol., vol. 7 (2010) pp. 309-317.

Fan et al., "digeR: A Graphical User Interface R package for analyzing 2D DIGE data," Bioinformatics Advance Access (2009) pp. 1-3.

Etzioni et al., "Combining biomarkers to detect disease with application to prostate cancer," Biostatistics, vol. 4.4 (2003) pp. 523-538.

English translation of the international preliminary report on patentability in international application PCT/EP2006/061498, to which U.S. Appl. No. 11/511,930 claims priority (Oct. 18, 2007).

* cited by examiner

FIG. 4 CLASS NETWORK

SPECIFY A CLASS NETWORK

PROCESS HIERARCHY

SPECIFY A PROCESS HIERARCHY

SPECIFICATION MODE

EXECUTION MODE

PERFORM DATA ANALYSIS AND
GENERATE DATA NETWORK

EXECUTE PROCESS STEPS

GENERATE DOMAIN
OF PROCESS STEP

DATA NETWORK OF A
3-DIMENSIONAL OBJECT

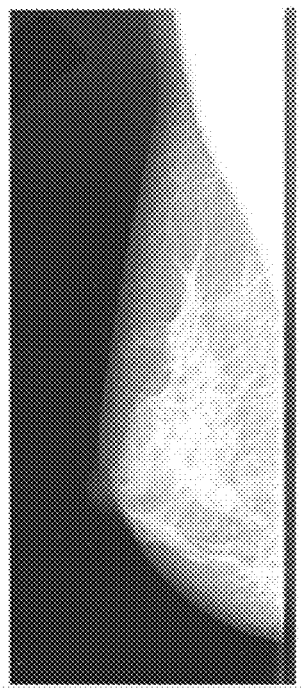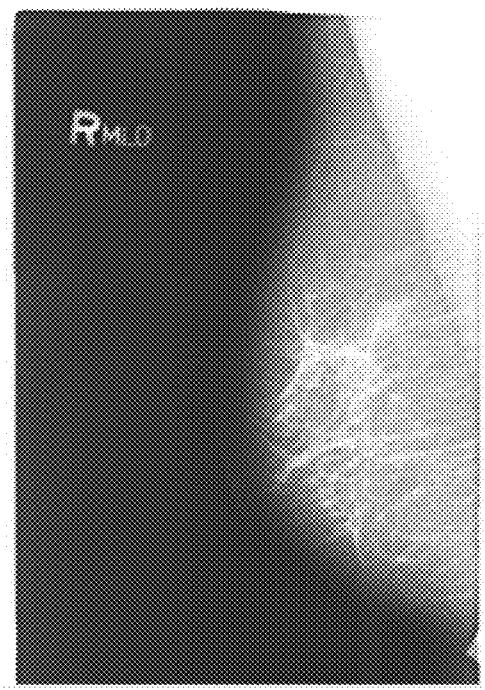
FIG. 20

FIG. 21

```xml
<?xml version="1.0" encoding="UTF-8" ?>
<eCog.Proc UserName="guenter" Company="Definiens AG" Copyright="" version="20050718"
    use-reproducable-poly="1" NumLvl="2" project-unit="1" engine-version="5.5.0" engine-
    build="534">
    <!-- Below are Image Layers -->
    <ImgLayers>
    <!-- Below are Thematic Layers -->
    <ThmLayers>
    <!-- Below are Map Levels -->
    <MapLvlProxyCntnr>
    <ParamValueSetCntnr />
    <!-- Below are Variables for Process Steps -->
    <ProcVrblCntnr>
    <!-- Below are the Classes of the Class Network; See e.g., FIG.4 -->
    <ClssHrchy EvalInvalid="1" MinProb="0.10000000000000001"
        NNSlope="0.20000000000000001" PrjctBaseUnit="1" NumGisChnl="1">
    <!-- Below are Samples for Training Cognition Network -->
    <Smpls>
    <CustProcAlgrList />
    <!-- Below are Process Steps of Process Hierarchy; See FIG.6 -->
    <ProcessList>
        <!-- Below is the Root Process Step of the Process Hierarchy; See 41 in FIG.6 -->
        <ProcBase Name="mamma-v002" bLoopChg="0" iMaxCycle="1" bExpand="1"
            bActive="1" bAutoName="0" sComment="">
    </ProcessList>
    <ExportedItems />
    <LensIds />
    <Behaviour>
        <DistCalc mode="CG" />
    </Behaviour>
</eCog.Proc>
```

```
<!-- Below is the Right Mediolateral Oblique Class; See FIG.4 -->
+ <Clss id="14" name="breast-r-mlo" flag="0" iMaskID="-1" termType="0"
    strUserName="guenter" tChngTime="1153164004" bShow="0" sComment="">        133
    <!-- Below is the Mamilla Class; See FIG.4 -->                              )
+ <Clss id="15" name="mamilla" flag="0" iMaskID="-1" termType="0" strUserName="guenter"
    tChngTime="1153165610" bShow="0" sComment="">
+ <Clss id="16" name="_marked" flag="0" iMaskID="-1" termType="0" strUserName="guenter"
134   tChngTime="1153209169" bShow="0" sComment="">
    <!-- Below is a Helper Class for training the Cognition Network; See FIG.4 -->
+ <Clss id="17" name="_helpers" flag="2" iMaskID="-1" termType="0" strUserName="guenter"
    tChngTime="1153209187" bShow="0" sComment="">
+ <Clss id="18" name="links" flag="2" iMaskID="-1" termType="0" strUserName="guenter"
    tChngTime="1153209745" bShow="0" sComment="">
+ <Clss id="19" name="link-symmetry" flag="0" iMaskID="-1" termType="0"
    strUserName="guenter" tChngTime="1153209749" bShow="0" sComment="">
+ <Clss id="20" name="link-views" flag="0" iMaskID="-1" termType="0" strUserName="guenter"
    tChngTime="1153209764" bShow="0" sComment="">
  </AllClss>
+ <AllProps>
+ <ChnlWghtBrght>
+ <AllSubClss>
+ <AllTerm>
  </ClssHrchy>
  <!-- Below are Samples for Training Cognition Network -->
- <Smpls>
+ <AllClss>
+ <AllProp>
  </Smpls>
  <CustProcAlgrList />
  <!-- Below are Process Steps of Process Hierarchy; See FIG.6 -->
- <ProcessList>
    <!-- Below is the Root Process Step of the Process Hierarchy; See 41 in FIG.6 -->
  - <ProcBase Name="mamma-v002" bLoopChg="0" iMaxCycle="1" bExpand="1" bActive="1"
      bAutoName="0" sComment="">
      <LensInfo tLensId="0" sPwd="" />
    + <Algorithm guid="A88A5775-CC39-4194-9A6A-A64872EE1F81">
    + <Domain>
      <!-- Below is the Process Step "Initialization" 44 in FIG.6 -->
    - <SubProc>
      + <ProcBase Name="initialization" bLoopChg="0" iMaxCycle="1" bExpand="1" bActive="1"
          bAutoName="0" sComment="">
          <!-- Below is the Process Step "Detect Breasts" 45 in FIG.6 -->
        - <ProcBase Name="detect breasts" bLoopChg="0" iMaxCycle="1" bExpand="1" bActive="1"
            bAutoName="0" sComment="">
            <LensInfo tLensId="0" sPwd="" />
            <!-- Below is the Algorithm 60 for Process Step "Detect Breasts" 45 in
            FIG.6 -->
          + <Algorithm guid="A88A5775-CC39-4194-9A6A-A64872EE1F81">
            <!-- Below is the Domain Specification 58 of Process Step "Detect
            Breasts" 45 in FIG.6 -->
          - <Domain>
            + <ProcDomain sThmLayer="" iNumMaxObj="0" iVersion="4">
            </Domain>
          - <SubProc>
```

FIG. 25B

```xml
<!-- Below is the Sub-Process Step "Segmentation" 50 in FIG.6 -->
- <ProcBase Name="segmentation" bLoopChg="0" iMaxCycle="1" bExpand="0"
    bActive="1" bAutoName="0" sComment="">
    <LensInfo tLensId="0" sPwd="" />
  + <Algorithm guid="A8BA5775-CC39-4194-9A6A-A64872EE1F81">
  + <Domain>
  + <SubProc>
  </ProcBase>
+ <ProcBase Name="at breasts: objects-mean = mean(Layer 1)" bLoopChg="0"
    iMaxCycle="1" bExpand="1" bActive="1" bAutoName="1" sComment="">
    <!-- Below is the Sub-Process Step "Classification" 51 in FIG.6 -->
- <ProcBase Name="classification" bLoopChg="0" iMaxCycle="1" bExpand="0"
    bActive="1" bAutoName="0" sComment="">
    <LensInfo tLensId="0" sPwd="" />
  + <Algorithm guid="A8BA5775-CC39-4194-9A6A-A64872EE1F81">
  + <Domain>
  - <SubProc>
      <!-- Below is the Sub-Process Step "Breast Area" 53 in FIG.6 -->
      - <ProcBase Name="breast-area-min = Number of pixels" bLoopChg="0"
          iMaxCycle="1" bExpand="1" bActive="1" bAutoName="1" sComment="">
          <LensInfo tLensId="0" sPwd="" />
          <!-- Below is the Algorithm 61 for Sub-Process Step "Breast
          Area" 53 in FIG.6 -->
        + <Algorithm guid="15EB03DD-5DE7-4f59-9CBD-60AA256ADFDE">
        + <Domain>
          <SubProc />
        </ProcBase>
      + <ProcBase Name="breast-area-min /= NUM_COLS" bLoopChg="0"
          iMaxCycle="1" bExpand="1" bActive="1" bAutoName="1" sComment="">
      + <ProcBase Name="breast-area-min /= NUM_ROWS" bLoopChg="0"
          iMaxCycle="1" bExpand="1" bActive="1" bAutoName="1" sComment="">
      + <ProcBase Name="breast-area-min /= 4" bLoopChg="0" iMaxCycle="1"
          bExpand="1" bActive="1" bAutoName="1" sComment="">
      + <ProcBase Name="with Mean Layer 1 Rqt; objects-mean at breasts:
          for all" bLoopChg="0" iMaxCycle="1" bExpand="0" bActive="1"
          bAutoName="1" sComment="">
    </SubProc>
  </ProcBase>
+ <ProcBase Name="breast at breasts: merge region" bLoopChg="0"
    iMaxCycle="1" bExpand="1" bActive="1" bAutoName="1" sComment="">
+ <ProcBase Name="breast at breasts: breast-lcc, breast-r-mlo, breast-rcc,
    breast-l-mlo *" bLoopChg="0" iMaxCycle="1" bExpand="1" bActive="1"
    bAutoName="1" sComment="">
  </SubProc>
</ProcBase>
<!-- Below is the Process Step "Detect Background" 46 in FIG.6 -->
+ <ProcBase Name="detect background" bLoopChg="0" iMaxCycle="1" bExpand="0"
    bActive="1" bAutoName="0" sComment="">
  <!-- Below is the Process Step "Detect Fragments" 47 in FIG.6 -->
- <ProcBase Name="detect fragments" bLoopChg="0" iMaxCycle="1" bExpand="0"
    bActive="1" bAutoName="0" sComment="">
    <LensInfo tLensId="0" sPwd="" />
  + <Algorithm guid="A8BA5775-CC39-4194-9A6A-A64872EE1F81">
  + <Domain>
  - <SubProc>
```

FIG. 25C

```
<!-- Below is the Sub-Process Step "Mamilla Segmentation" S4 in FIG.6
-->
- <ProcBase Name="prepare mamilla segmentation" bLoopChg="0" iMaxCycle="1"
    bExpand="0" bActive="1" bAutoName="0" sComment="">
    <LensInfo tLensId="0" sPwd="" />
 + <Algorithm guid="A8BA5775-CC39-4194-9A6A-A64872EE1F81">
 + <Domain>
 - <SubProc>
     <!-- Below is the Sub-Process Step "Detect Skin" S7 in FIG.6 -
     -->
   + <ProcBase Name="detect skin" bLoopChg="0" iMaxCycle="1" bExpand="0"
       bActive="1" bAutoName="0" sComment="">
   + <ProcBase Name="detect mamilla region (TODO: enhance this to
       handle 2 views)" bLoopChg="0" iMaxCycle="1" bExpand="0" bActive="1"
       bAutoName="0" sComment="">
   </SubProc>
  </ProcBase>
+ <ProcBase Name="segmentation" bLoopChg="0" iMaxCycle="1" bExpand="0"
    bActive="1" bAutoName="0" sComment="">
  <!-- Below is the Process Step "Link Mammillae" S5 in FIG.6 -->
- <ProcBase Name="link mamillae" bLoopChg="0" iMaxCycle="1" bExpand="1"
    bActive="1" bAutoName="0" sComment="">
    <LensInfo tLensId="0" sPwd="" />
 + <Algorithm guid="A8BA5775-CC39-4194-9A6A-A64872EE1F81">
 + <Domain>
 - <SubProc>
   - <ProcBase Name="mamilla with Existence of super objects breast-rcc
       (1) > 0 at fragments: for all" bLoopChg="0" iMaxCycle="1"
       bExpand="1" bActive="1" bAutoName="1" sComment="">
       <LensInfo tLensId="0" sPwd="" />
     - <Algorithm guid="A8BA5775-CC39-4194-9A6A-A64872EE1F81">
         <Params />
       </Algorithm>
     - <Domain>
       - <ProcDmnFtrLvl>
         - <ProcDomain sThmLayer="" iNumMaxObj="0" iVersion="4">
           - <mClssFltr eState="2" bUnclsfy="0" bUseDmnTxt="1">
             - <IClss>
  135 ─┤       - <DListInt>
                  <int value="15" />
                </DListInt>
             </IClss>
           </mClssFltr>
          + <TermThrsh eCmpr="3" eBaseUnit="0">
         </ProcDomain>
       + <MapLvlProxy strName="fragments" MapLvl="2">
       </ProcDmnFtrLvl>
     </Domain>
    + <SubProc>
   </ProcBase>
```

FIG. 25D

```
+ <ProcBase Name="mamilla with Existence of super objects breast-i-
    mlo (1) > 0 at fragments: for all" bLoopChg="0" iMaxCycle="1"
    bExpand="1" bActive="1" bAutoName="1" sComment="">
    </SubProc>
  </ProcBase>
  </SubProc>
</ProcBase>
<!-- Below is the Process Step "Helper Classes" 48 in FIG. 6 -->
- <ProcBase Name="helpers" bLoopChg="0" iMaxCycle="1" bExpand="1" bActive="0"
    bAutoName="0" sComment="">
    <LensInfo tLensId="0" sPwd="" />
  + <Algorithm guid="A8BA5775-CC39-4194-9A6A-A64872EE1F81">
  + <Domain>
  - <SubProc>
    + <ProcBase Name="class-storage" bLoopChg="0" iMaxCycle="1" bExpand="1"
        bActive="0" bAutoName="0" sComment="">
    + <ProcBase Name="at fragments: unlink all[from any if 0%
        <=weight<=100%]" bLoopChg="0" iMaxCycle="1" bExpand="1"
        bActive="1" bAutoName="1" sComment="">
    </SubProc>
  </ProcBase>
  </SubProc>
</ProcBase>
</ProcessList>
<ExportedItems />
<LensIds />
+ <Behaviour>
</eCog.Proc>
```

FIG. 25E

KEY TO FIG. 25

CONTEXT DRIVEN IMAGE MINING TO GENERATE IMAGE-BASED BIOMARKERS

CROSS REFERENCE TO RELATED APPLICATION

This application is a continuation of, and claims priority under 35 U.S.C. §120 from, nonprovisional U.S. patent application Ser. No. 12/930,873, filed on Jan. 18, 2011, now U.S. Pat. No. 8,594,410, which in turn is a continuation in part of, and claims priority under 35 U.S.C. §120 from, nonprovisional U.S. patent application Ser. No. 11/511,930 entitled "Cognition Integrator and Language," filed on Aug. 28, 2006, now U.S. Pat. No. 7,873,223. In addition, application Ser. No. 12/930,873 claims the benefit under 35 U.S.C. §119 of provisional application Ser. No. 61/459,180, entitled "Content Driven Image Mining to Generate Image-Based Biomarkers", filed Dec. 8, 2010. Application Ser. No. 11/511,930, in turn, claims priority under 35 U.S.C. §120 from PCT application PCT/EP2006/061498 filed on Apr. 10, 2006, which in turn is a continuation application of German Application No. DE 102005016290.8 filed on Apr. 8, 2005, in Germany. Application Ser. No. 11/511,930 also claims priority under 35 U.S.C. §120 from, nonprovisional U.S. patent application Ser. No. 10/687,477 entitled "Extracting Information from Input Data Using a Semantic Cognition Network," filed on Oct. 15, 2003, now U.S. Pat. No. 7,146,380. Application Ser. No. 10/687,477 in turn claims the benefit under 35 U.S.C. §119 from, German Application No. 102 48 013.3, filed on Oct. 15, 2002, in Germany. The subject matter of each of the foregoing documents is incorporated herein by reference.

TECHNICAL FIELD

The present invention relates generally to image analysis, and more specifically to a system for computer-aided diagnosis that develops and modifies biomarkers based on the image analysis results that best correlate to clinical endpoints.

REFERENCE TO ASCII TEXT FILE APPENDIX

This application includes an ASCII text file appendix containing source code to software that embodies the inventions described herein. The software code is algorithmic structure of a means for generating a custom image-based biomarker that identifies digital images of patients with similar medical conditions. The source code is in ASCII format. A portion of the disclosure of this patent document contains material that is subject to copyright protection. All the material on the ASCII text file appendix is hereby expressly incorporated by reference into the present application. The copyright owner of that material has no objection to the facsimile reproduction by anyone of the patent document or the patent disclosure, as it appears in the Patent and Trademark Office patent files or records, but otherwise reserves all copyright rights. The ASCII text file appendix includes two text files readable in the MS-Windows operating system. The first file is named "cellbiol-3d-v4", is 128 kilobytes large, was created on Aug. 25, 2006, and is an ASCII version of the XML representation shown in part in FIGS. 24-25. The second file is named "mamma-v002", is 202 kilobytes large, was created on Aug. 25, 2006, and is an ASCII version of the XML code that generates the visual representation of FIG. 21.

BACKGROUND

Systems for detecting and analyzing target patterns in digital imagery have a wide variety of uses. Such systems can be used to detect geographical objects, military targets or weather patterns from satellite images. Radar or sonar shadows of airplanes, ships, submarines and schools of fish can also be detected and analyzed. Much effort has been expended to develop systems for detecting and analyzing anatomical regions in radiological images. For example, systems for analyzing computed tomography (CT) images are used for the computer-aided detection (CAD) of cancerous regions in human lungs.

One of the more difficult tasks of detecting patterns in medical images involves detecting cancerous mass lesions and micro-calcifications in X-ray images of breasts (also called mammograms). Early detection of these cancerous regions in the breast increases the chance of survival of women with breast cancer. The X-ray images are digitized, and the pixel data is analyzed. Detecting cancerous regions in breasts is made more difficult, however, by the similar appearance of pixels associated with benign and malignant lesions and micro-calcifications.

Systems for computer-assisted interpretation of mammograms are now widely used to assist in the early detection of breast cancer. Such systems include ImageChecker by R2 Technologies of Sunnyvale, Calif.; Second Look by CADx Systems of Beavercreek, Ohio and MammoReader by iCAD of Hudson, N.H. These systems are designed to provide very high detection rates of cancerous regions at the expense of "detecting" a significant number of regions that are not cancerous. As the probability threshold of missing a cancerous region is lowered, the rate of incorrectly designating cancerous regions increases. Thus, although current systems have achieved a high degree of sensitivity, there remains a tradeoff between the probability threshold for detected objects and the false positive detection rate. Systems employing computer-aided detection (CAD) of early breast cancer can, therefore, be improved by decreasing the false positive detection rate while maintaining the detection of nearly all cancerous regions.

Current CAD schemes for analyzing mammograms to detect breast cancer involve rules-based selection of abnormal regions. The rules are based on pixel filtering and thresholding and the dimensions and orientation of the target region. For example, pixel data from a mammogram is filtered according to brightness or intensity, and pixels with a similar brightness are associated together as an object. A gradient histogram is used to indicate the statistical distribution of brightness among all pixels of the mammogram. The histogram is then used to define thresholds for the brightness of pixels that are associated together. In addition to filtering and thresholding, the distance of one pixel from another pixel may be used to determine whether pixels are associated together. For example, the spatial orientation and the ratio of the dimensions of an area of brightness may be used to determine whether the area is cancerous. Once the CAD scheme has been developed, however, the process of detecting abnormal regions is static. Although the threshold and filtering variables and the target dimensions can be adjusted, the process in which the rules are applied does not change once the CAD scheme begins analyzing a particular digital image.

An improved CAD scheme is sought for locating specified image structures in a digital image that decreases the false positive detection rate while detecting substantially all of the target objects in the digital image. Such an improved CAD scheme is desired in which the process itself adapts to the characteristics of the digital image in which the target objects are located. Moreover, such an improved CAD scheme would detect an object in a digital image by employing processes in addition to associating pixels with an object based on filtering and thresholding pixels and on the dimensions of the object.

SUMMARY

A Cognition Program performs computer-aided detection (CAD) of target objects found in data tables. In one aspect, the data tables include text data as well as pixel values that make up digital images. At run time, the Cognition Program links similar pixel values to objects (nodes) of a data network.

In a specification mode, a user of the Cognition Program uses a novel scripting language to specify classes of a class network and process steps of a process hierarchy. The classes describe what the user expects to find in the digital images. The process hierarchy describes how the digital images are to be analyzed in order to find a target object. Each process step includes a domain specification and an algorithm. The domain specifies the classes whose associated objects will be operated upon by the algorithm in an execution mode at run time. The user also specifies types of links that are to connect objects of the data network, process steps and classes to each other. In addition, the user specifies link types for links between process steps and classes and between classes and objects. A link between two nodes describes the relationship between the two nodes.

The Cognition Program acquires table data values that include the pixel values of the digital images, as well as metadata relating to the digital images, such as the text data. In one example, the digital images are the left and right side views and left and right top views of a mammogram of a patient who is suspected of having breast cancer, and the metadata is information relating to the patient. The Cognition Program integrates the information of the four digital images and the metadata.

In the execution mode, the Cognition Program generates the data network in which pixel values are linked to objects, and objects are categorized as belonging to specific classes. Moreover, the Cognition Program generates a computer-implemented network structure that includes the data network, the process hierarchy and the class network. In the computer-implemented network structure, the process steps, classes and objects are linked to each other in a manner that enables the Cognition Program to detect a target object in the digital images that is defined by a class. For example, an algorithm of a process step may be linked to an item of metadata, or a domain specification of a process step may be linked to an object of the data network. The Cognition Program and novel scripting language can also be used to analyze satellite images to detect specific ships in a harbor.

In another aspect, the data network is generated from many data tables, each containing a digital image. By generating the data network from digital images obtained from many parallel planar slices of a three-dimensional data set of a physical object, the Cognition Program detects three-dimensional target regions in the physical object.

In yet another aspect, the table data values acquired by the Cognition Program are obtained from a first group of parallel planar scans of a three-dimensional physical object taken at one time and from a second group of parallel planar scans of the three-dimensional physical object taken at a different time. Generating the computer-implemented network structure enables the Cognition Program to depict movement of the three-dimensional physical object.

In another embodiment, the Cognition Program generates image-based biomarkers that predict clinical endpoints of patients. Data mining techniques are combined with image analysis to achieve context-driven image mining. An image-based biomarker is a predetermined set of image features weighted and combined in a predetermined manner to provide an indication of a clinical endpoint, such as a survival time or a disease recurrence probability.

In one method, an image-based biomarker is generated that better correlates with the clinical endpoint. The image-based biomarker is generated using image features obtained through object-oriented image analysis of medical images. The values of a first subset of image features are measured. Each of the values is then weighted. The magnitude of the first image-based biomarker is calculated by summing the weighted values of all of the image features. The magnitude of the biomarker for each patient is correlated with a clinical endpoint that was observed for the patient whose medical images were analyzed. How the first image-based biomarker correlates with the clinical endpoint observed for each of the patients is displayed on a graphical user interface as a scatter plot.

A second subset of image features is then selected that belong to a second image-based biomarker such that the magnitudes of the second image-based biomarker better correlate with the clinical endpoints observed for the patients. The second biomarker can then be used to predict the clinical endpoint of other patients whose clinical endpoints have not yet been observed.

In another method, an additional image-based biomarker is generated that better correlates with a subgroup of outlier points representing patients whose clinical endpoints do not correlate well with the baseline image-based biomarker. Pixel values of medical images of a group of patients are first acquired. Objects of a data network for each of the medical images are generated by linking selected pixel values to selected objects according to a class network and a process hierarchy. The objects are measured to obtain a value for each of a plurality of image features. A first subset of the image features is selected that belong to a first image-based biomarker. The first image-based biomarker is correlated for each of the patients with a clinical endpoint observed for that patient. How the first image-based biomarker correlates with the clinical endpoint observed for each of the patients is displayed on a graphical user interface, for example in a scatter plot. A subgroup of the patients is identified for which the first image-based biomarker correlates poorly with the clinical endpoints observed for the patients in the subgroup. For example, the subgroup includes the points of the scatter plot that are farthest away from a linear regression line through the middle of the largest group of points.

A second subset of the image features is then selected that belongs to a second image-based biomarker that better correlates with the clinical endpoints observed for the patients in the subgroup. The second image-based biomarker can then be used to predict the clinical endpoint of patients whose clinical endpoints have not yet been observed and for whom the first image-based biomarker results in a magnitude that falls outside a predefined base range.

Other embodiments and advantages are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

FIG. 20 is a screenshot output by the Cognition Program comparing two mammograms that have been chosen because of their similarities.

FIG. 21 is a screenshot of a process hierarchy used by another embodiment of the computer-implemented network structure of FIG. 1 to analyze individual cells in a cell assay.

FIG. 24 is a listing of high-level lines of XML code corresponding to a Cognition Language script that implements a class network and a process hierarchy for analyzing mammograms.

FIGS. 25A-E show more lines of the XML code of FIG. 24.

DETAILED DESCRIPTION

Reference will now be made in detail to some embodiments of the invention, examples of which are illustrated in the accompanying drawings.

Figure 1:
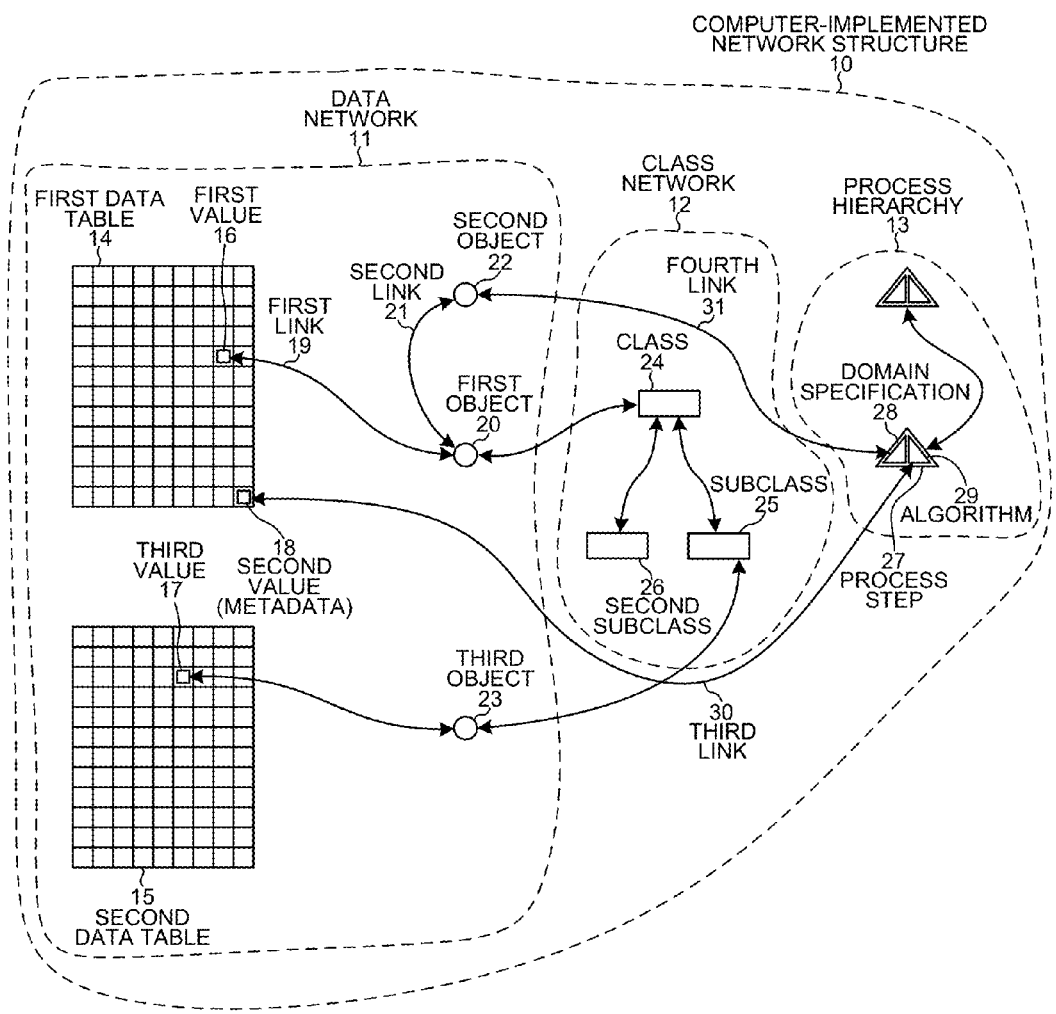
FIG. 1 is a simplified schematic diagram of a computer-implemented network structure that includes a data network, a class network and a process hierarchy.

FIG. 1 is a simplified diagram of a computer-implemented network structure 10 used to locate information of interest from among table data values. The network structure 10 includes a data network 11, a class network 12 and a process hierarchy 13. In the example of FIG. 1, data network 11 includes a first data table 14 and a second data table 15. The table data values in data tables 14-15 are in the form of both numbers and text.

In one embodiment, some of the table data values describe a medical patient, while other table data values are digital pixel values from a medical image of the patient. The patient is suspected of having breast cancer, and the medical image is a mammogram. Thus, some of the table data values are floating-point values representing the spectral intensity of individual pixels of the digitized mammogram. The other table data values are items of metadata relating to the mammogram, such as patient information relevant to whether the patient might have breast cancer. Examples of such information include the patient's gender, age, weight, height, blood values, prescribed medications, number of children, the family history of ailments, whether the patient breast-fed her children, and whether the patient smoked or used drugs. In FIG. 1, a first value 16 and a third value 17 are spectral intensity values from the mammogram, whereas second value 18 is an item of metadata, such as the weight of the patient.

In this embodiment, network structure 10 is used for the detection of early breast cancer by identifying target regions on images of breasts. The visual inspection of mammograms is time consuming and labor intensive. Because of the low prevalence of target objects in the many mammograms read by clinical doctors and radiologists, tedium can cause the doctor or radiologist to overlook a target object when it is present. Network structure 10 and the associated computer program that generates network structure 10 help the doctor and radiologist to avoid overlooking any cancerous regions in the mammograms they are inspecting. The associated computer program is called the Cognition Program.

Figure 2:
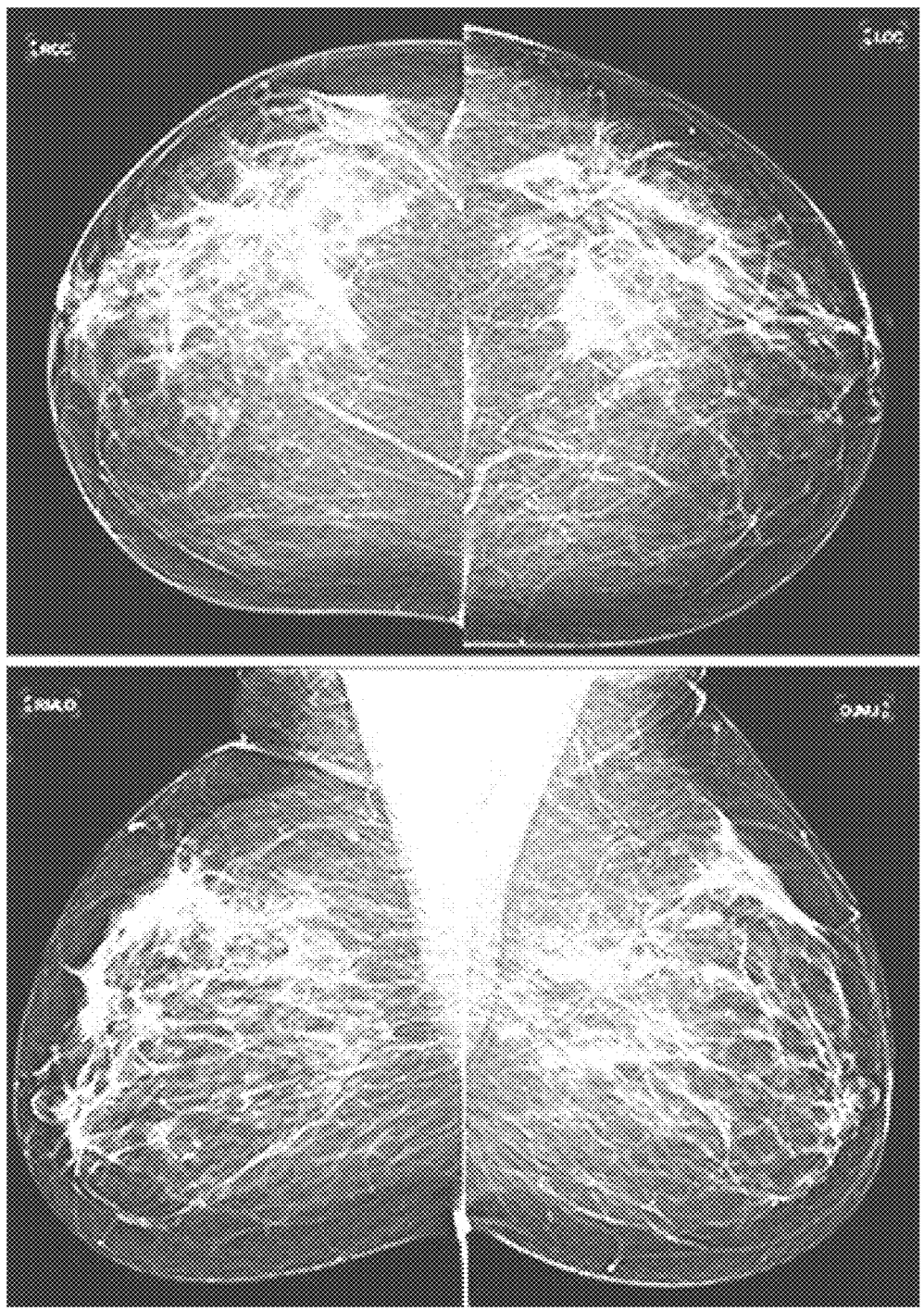
FIG. 2 is a digital image including the right and left craniocaudal views and the right and left mediolateral oblique views of a mammogram.

FIG. 2 is an example of an image that is analyzed by network structure 10 and the Cognition Program. The upper portion of the image shows a top craniocaudal (CC) view of a right and a left breast. The lower portion of the image shows a side mediolateral oblique (MLO) view of the same right and left breasts. Thus, first data table 14 includes the pixel data of the craniocaudal (CC) view plus items of metadata, and second data table 15 includes the pixel data of the mediolateral oblique (MLO) view. In other embodiments, second data table 15 also includes metadata relating to the patient. Network structure 10 is used to identify and mark target regions on FIG. 2 that are likely to contain cancerous mass lesions and micro-calcifications.

Returning to FIG. 1, data network 11 also includes objects and links. In this example, first value 16 is linked by a first link 19 to a first object 20. First object 20 is linked by a second link 21 to a second object 22. Data network 11 also includes a third object 23 that is linked to the third data value 17.

Class network 12 includes a class 24, a subclass 25 and a second subclass 26. Class 24 is linked to subclass 25 and to second subclass 26. In addition, class 24 of class network 12 is linked to first object 20 of data network 11. And subclass 25 is linked to third object 23. Process hierarchy 13 includes a process step 27. Process step 27 in turn includes a domain specification 28 and an algorithm 29. Algorithm 29 is linked by a third link 30 to the second value 18 of first data table 14. Domain specification 28 is linked by a fourth link 31 to the second object 22. Thus, an algorithm of a process step in process hierarchy 13 is linked to metadata in data network 11, and a domain specification of a process step in process hierarchy 13 is linked to an object in data network 11.

Figure 3:
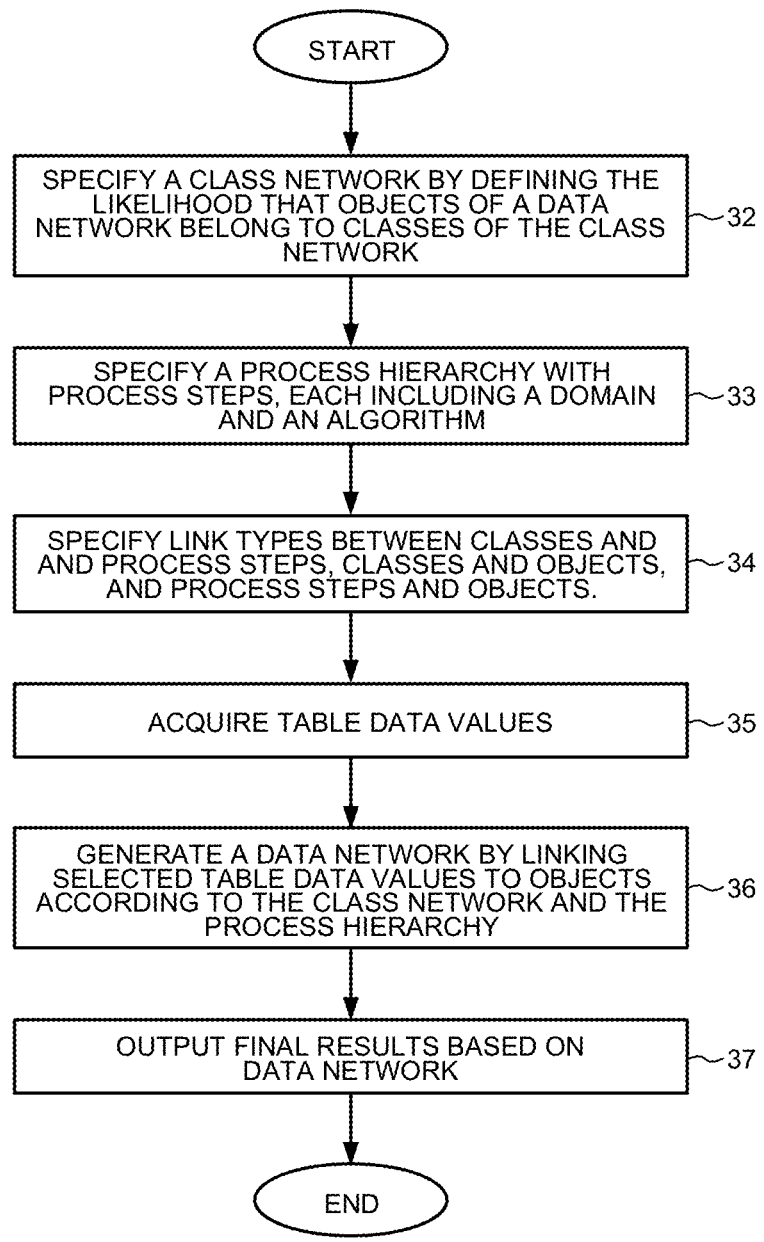
FIG. 3 is a flowchart of steps for performing computer-aided detection of target regions in digital images using the computer-implemented network structure of FIG. 1.

FIG. 3 is a flowchart illustrating steps 32-37 of a method by which network structure 10 and the Cognition Program together perform computer-aided detection (CAD) of target regions in digital images that depict cancerous mass lesions and micro-calcifications in human breasts. In other embodiments described below, network structure 10 is used to detect other objects. The steps of FIG. 3 will now be described in relation to the operation of network structure 10 of FIG. 1 and the Cognition Program.

In first step 32, a user of the Cognition Program specifies class network 12 by defining the likelihood that objects of data network 11 will belong to each particular class of class network 12. The user of the Cognition Program is, for example, a research doctor who is applying his expert knowledge to train the Cognition Program in a specification mode. In addition to the research doctor, clinical doctors then also use the Cognition Program in an execution mode.

Figure 4:
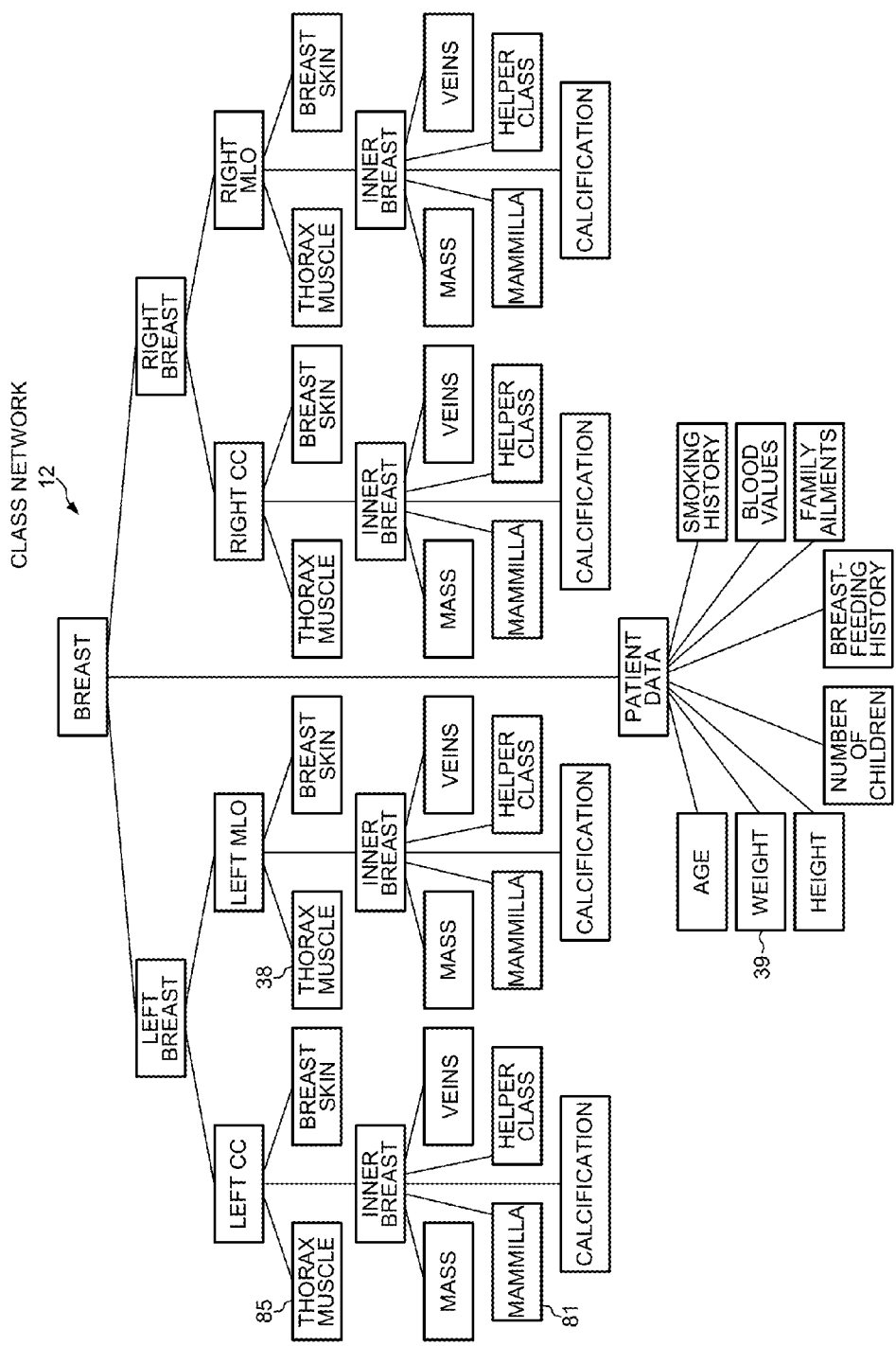
FIG. 4 is a diagram showing the class network of FIG. 1 in more detail.

FIG. 4 shows class network 12 of FIG. 1 in more detail. Class network 12 includes classes linked to subclasses that describe what the user expects to find in the digital images included in first data table 14 and second data table 15. Thus, in this example, the classes and subclasses of FIG. 4 describe what the user expects to see in the images of FIG. 2. The user starts by giving each class a name. In this example, the user has specified a left breast and a right breast, corresponding to the left and right sides of the mammogram of FIG. 2. For the left breast, for example, the user has specified a craniocaudal (CC) view and a mediolateral oblique (MLO) view, corresponding to the top and bottom portions of the mammogram of FIG. 2, respectively. For the left MLO view, for example, the user has specified classes for the thorax muscle 38, the breast skin and the inner breast. The thorax muscle corresponds to the white triangle in the upper right corner of the left MLO view in FIG. 2. The user has also specified subclasses for the "inner breast" subclass, including subclasses named breast mass, mammilla, micro-calcification, helper class and veins. The user specifies a helper class to categorize parts of the digital image for which the user does not know the contents.

The user also specifies categories of metadata. In this example, class network 12 includes a class for patient data and subclasses specifying the types of patient data. The user has specified subclasses for the patient's age, weight 39, height, number of children, whether the patient breast-fed her children, the patient's family history of ailments, the patient's blood values, and whether the patient smoked.

Each class may have an associated membership function that defines the probability that an object of data network 11 will belong to the particular class. The membership functions do not define whether an individual pixel value belongs to a class. Rather, each object is a group of pixels linked to the object, and the user specifies the membership function by defining the properties that the object must have to belong to the class. Examples of such properties include the area, shape, color and texture of the object. The area of an object may be determined, for example, by the number of pixels linked to the object. An item of metadata may also be a variable in a membership function. For example, the area of an object that belongs to the breast mass may be larger if the age and weight of the patient are over certain thresholds.

Figure 5:
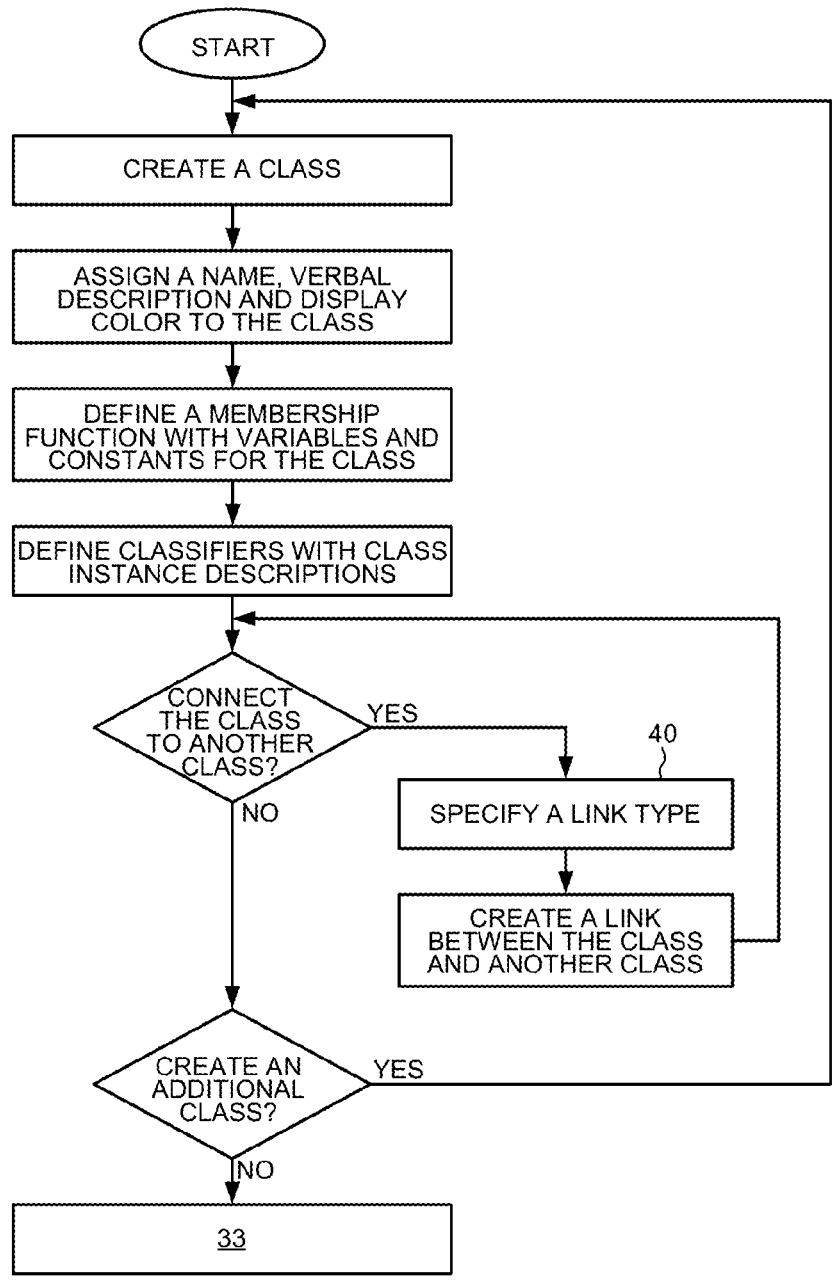
FIG. 5 is a flowchart showing the substeps of the first step of FIG. 3 for specifying the class network of FIG. 1.

FIG. 5 is a flowchart that illustrates the substeps of step 32 of FIG. 3 in more detail. In a substep 40, a link type for a link between two classes or subclasses is specified. Links that are not specified in substep 40 can also be specified later in step 34 of FIG. 3.

In step 33 of FIG. 3, the user specifies process hierarchy 13 of FIG. 1. The user specifies not only the individual process steps, but also the order in which the process steps are to be executed in the execution mode of the Cognition Program. Thus, each process hierarchy has a root process step linked to other process steps. The process steps in turn may be linked to substeps.

Figure 6:
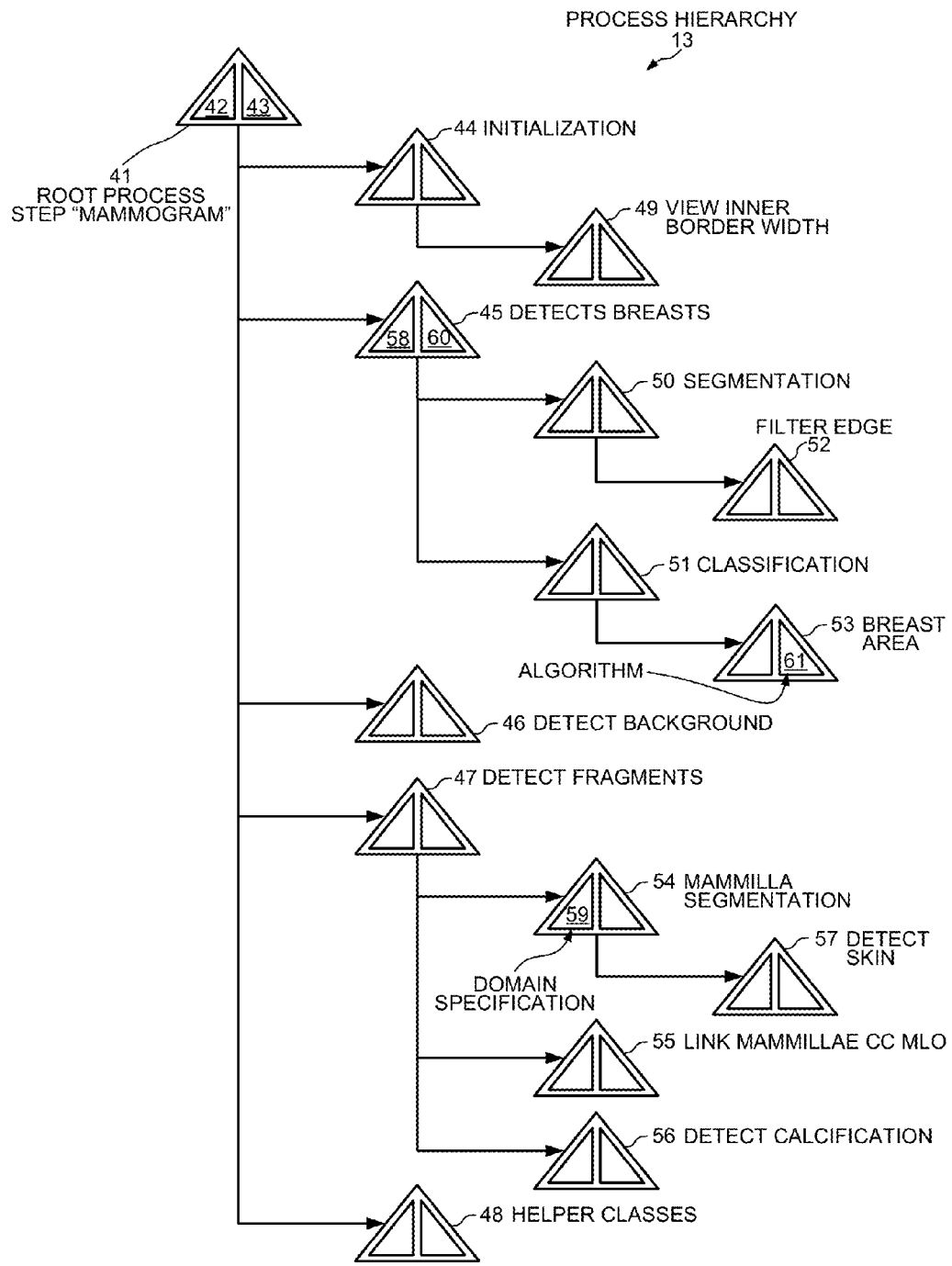
FIG. 6 is a diagram showing the process hierarchy of FIG. 1 in more detail.

FIG. 6 shows process hierarchy 13 of FIG. 1 in more detail. Process hierarchy 13 includes a root process step 41 named "Mammogram" with a domain specification 42 and an algorithm 43. In this example, the user has specified five process steps 44-48 linked in a specific order to root process step 41. The first process step 44 "Initialization" has a sub-process step 49 named "View Inner Border Width". The second process step 45 "Detect Breasts" has two sub-process steps 50-51, each with its own substep. Substep 50 "Segmentation" has a substep 52 named "Filter Edge". Substep 51 "Classification" has a substep 53 named "Breast Area". The third process step 47 "Detect Fragments" has three sub-process steps 54-56. Substep 54 "Mammilla Segmentation" has a substep 57 named "Detect Skin".

For each process step or sub-process step, the user has the option of specifying a domain and an algorithm. FIG. 6 shows that the user has specified a domain 58 for the process step 45 and a domain 59 for the sub-process step 54. The domain specifies classes that define the objects of data network 11 upon which the algorithm is to operate at run time in the execution mode. FIG. 6 also shows that the user has specified an algorithm 60 for the process step 45 and an algorithm 61 for the sub-process step 53.

Figure 7:
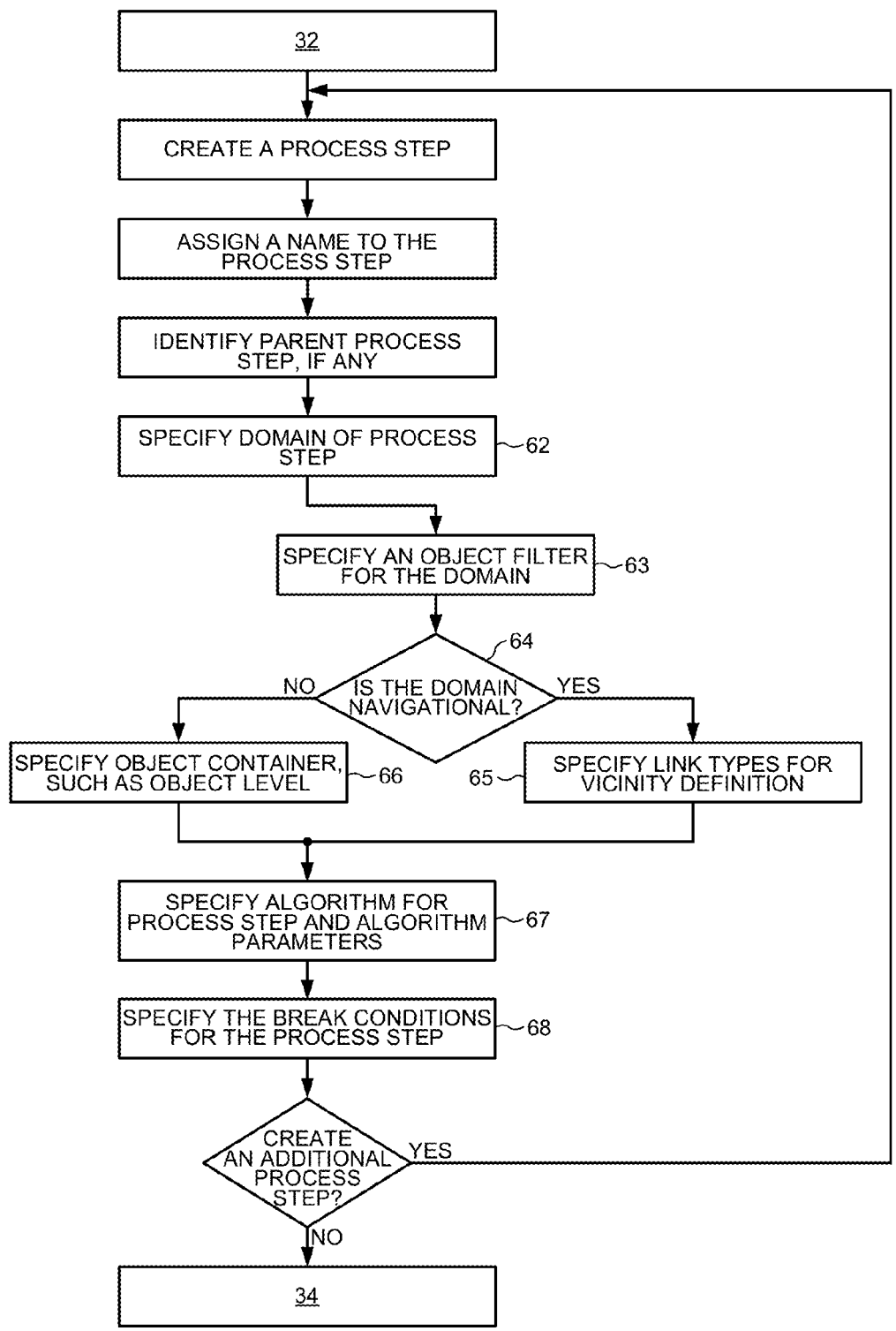
FIG. 7 is a flowchart showing the substeps of the second step of FIG. 3 for specifying the process hierarchy of FIG. 1.

FIG. 7 is a flowchart that illustrates the substeps of step 33 of FIG. 3 in more detail. In a substep 62, the user specifies the domain of the process step that the user has created. In a substep 63, the user specifies an object filter for the domain. For example, from the objects within the domain, the object filter passes to the algorithm all of those objects that are linked to fewer than ten pixel values. In a decision substep 64, the Cognition Program queries the user as to whether the domain is navigational. The user is queried by a dialogue in a pop-up window. The domain is navigational when the objects to be operated upon are defined based on how they are linked to other objects. For example, a domain may include only those subobjects that are linked by a certain type of link to a parent objects. If the domain is navigational, in a substep 65 the user specifies the link types that define the vicinity of the parent object. If the domain is not navigational, in a substep 66 the user specifies an object container for the objects that are to be operated upon by the algorithm of the process step. For example, the object container can be all of the objects at a specified object level. The level of objects linked directly to table data values is referred to as object level zero. Objects linked directly to objects in object level zero are considered to be in object level one, and so forth.

In a substep 67 of step 33 of FIG. 3, the user specifies the algorithm that will operate on the objects specified in the domain. The user can choose preformulated algorithms from a database of algorithms accessed by the Cognition Program. For example, some algorithms are used for the segmentation of objects. Other algorithms are used for computation, such as for statistical calculations or to calculate the area of pixels linked to an object.

Figure 8:
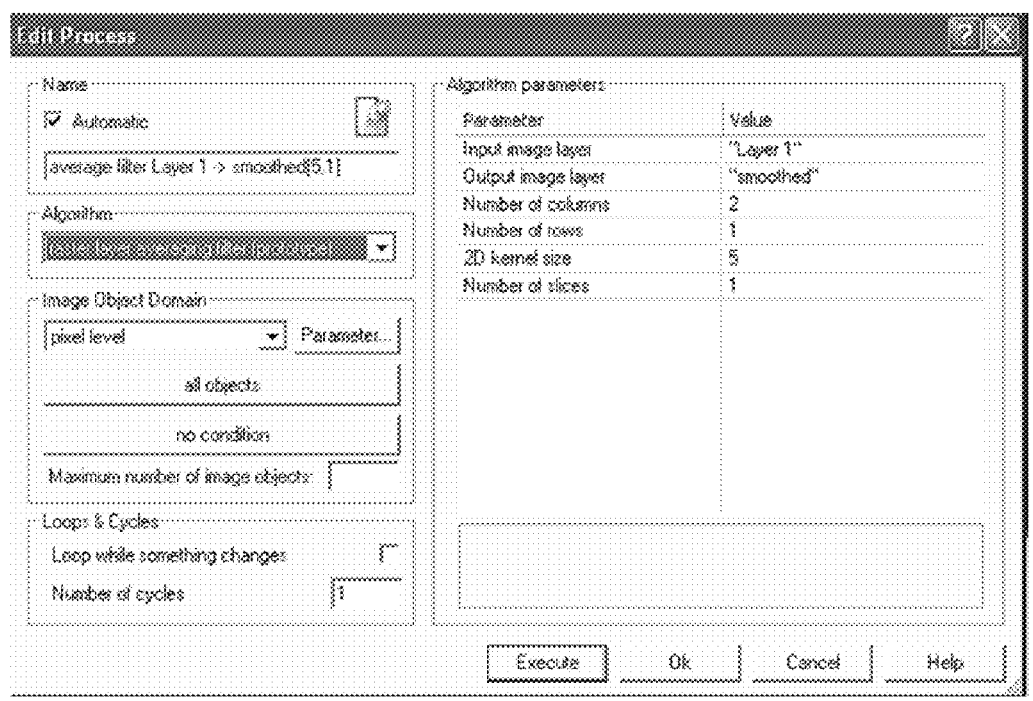
FIG. 8 is a screenshot of a pop-up window generated by a Cognition Program to assist in specifying an algorithm in a step of FIG. 7.

FIG. 8 shows a screenshot of a pop-up window generated by the Cognition Program to assist the user to specify the algorithm as described in substep 67.

In a substep 68, the user specifies a break condition at which the algorithm stops operating on objects. For example, the algorithm may be iterative and operate on a group of objects a predetermined number of times, as defined by the break condition.

In step 34 of FIG. 3, the user then specifies various types of links. In network structure 10, links can be between objects, between classes, and between process steps (collectively referred to here as nodes). In addition, there can be links between a class and an object, between a class and a process step, between a process step and an object, between a process step and table data, and between an object and table data. The links between a class and an object, between a process step and an object, and between an object and table data exit in network structure 10 only at run time during the execution mode of the Cognition Program. The user then uses the link types to define the relationship between the nodes of the class network and process hierarchy that the user specifies in the specification mode. In addition, the user uses the link types to define the relationship between the objects of the data network and the other nodes of network structure 10 that are to be generated at run time.

Figure 9:
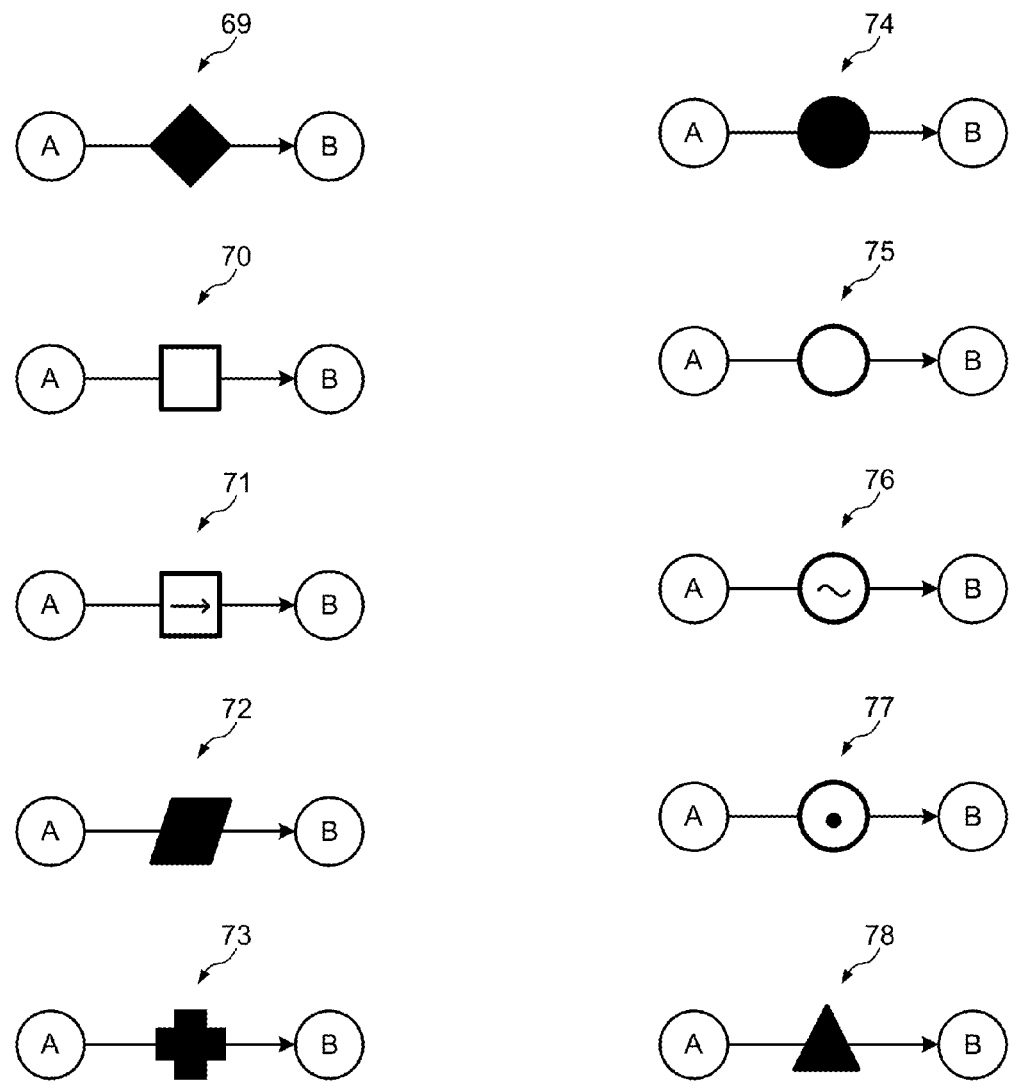
FIG. 9 is a diagram showing representations of various types of links in the computer-implemented network structure of FIG. 1.

FIG. 9 shows representations of various types of links 69-78 in network structure 10. The links describe the relation between the objects, classes and process steps. The most elementary types of links are either (i) exchange-relation links or (ii) relation links. Exchange-relation links describe an abstract, material or communicative exchange between nodes. Relation links, on the other hand, describe the relationship between nodes depending on relational contents. Where information is structured hierarchically, links are further subdivided into two groups. The first group links nodes at different hierarchy levels. The second group links nodes at the same hierarchy level.

Link 69 represents an exchange-relation link that connects nodes at different hierarchy levels. Link 69 represents the relationship between a larger, super-ordinated node A and a smaller, subordinated node B. Thus, link 69 represents a change in scale of information and denotes "B is part of A". Links 70-72 are exchange-relation links that connect nodes in the same hierarchy levels. These links do not represent a change in scale of information and denote "B is an output quantity of A". For example, the link 72 denotes "B is an attribute of A".

Link 73 represents a relation link that connects nodes at different hierarchy levels and thus performs a scale change. Link 73 denotes "B in general is A". Links 74-77 represent relation links that connect nodes in same hierarchy level. Link 75 denotes "A is locally adjacent to B"; link 76 denotes "A is similar to B"; and link 77 denotes "A is followed by B".

Link 78 represents a link that connects nodes that are capable of carrying out certain operations on other nodes and links. For example, a node connected to link 78 can generate new nodes or links and can also delete a node or a link. Link 78 denotes "B is function of A". For additional information on types of links in a semantic network structure, see U.S. patent application Ser. No. 11/414,000 entitled "Situation Dependent Operation of a Semantic Network Machine," filed on Apr. 28, 2006, which is incorporated herein by reference.

Although in the embodiment of FIG. 3 the link types are specified in step 34 after the class network and the process hierarchy are specified, in other embodiments the link types are specified before the class network and the process hierarchy are specified.

Figure 10:
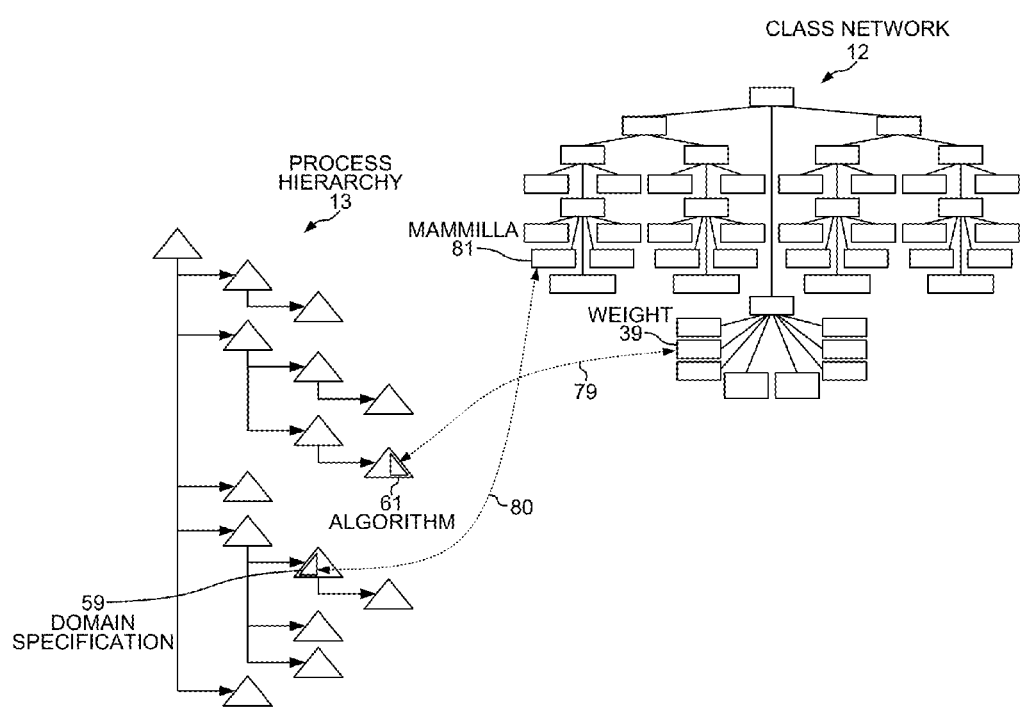
FIG. 10 is a simplified schematic diagram of the computer-implemented network structure of FIG. 1 after the class network and process hierarchy have been specified in the specification mode.

FIG. 10 illustrates the condition of computer-implemented network structure 10 in the specification mode after the user has specified class network 12 in step 32, process hierarchy 13 in step 33, and the link types in step 34. In this example, in the specification mode the user has specified a link 79 between algorithm 61 and subclass 39 (Weight) of class network 12. The user specifies link 79 by specifying that algorithm 61 determines the area of the objects that belong to the class Breast Mass depending on the weight of the patient. In the specification mode, the user has also specified a link 80 between domain specification 59 and a subclass 81 (Mammilla) of class network 12. The user specifies link 80 by specifying that domain 59 includes the objects that are determined in the execution mode to belong to subclass 81.

In step 35 of FIG. 3, the Cognition Program acquires the values of first data table 14 and second data table 15. In this example, the pixel values of the images of FIG. 2 are generated by an imaging device, such as an X-ray mammography device. In other embodiments, the imaging device is a computed tomography (CT), an ultrasound imaging device, or a magnetic resonance imaging (MRI) device. The imaging device includes an image digitizer that converts the X-ray image into a digital image. In other embodiments, physical mammographic x-ray film is sent through a film digitizer to obtain the pixel values of the data tables. In yet other embodiments, the radiological images are produced directly in digital format. The digital pixel values of the data tables indicate the grey levels (brightness) in the space domain of the images of FIG. 2. Metadata values are also acquired in step 35. In this example, some of the metadata is in text format, such as the identity of medication prescribed for the patient. Other metadata, such as the patient's weight, is in the form of a digital number.

In step 36 of FIG. 3, the Cognition Program runs in the execution mode and generates data network 11 by selectively linking table data values to objects according to the class network and the process hierarchy. While the classes of class network 12 describe what the user expects to find in the table data values, the objects reflect what the Cognition Program actually finds in the table data values. At run time in the execution mode, the Cognition Program executes the process steps as specified in process hierarchy 13. Each object is generated by linking to the object pixel values having similar characteristics, such as brightness. Thresholds of brightness of pixels that are associated together can be obtained from a gradient histogram of the pixel values in the digital image. The objects are then linked together into classes according to the membership functions of the classes. Thus, classes are linked to objects at run time. In addition, classes and process steps are linked to table data at run time.

Figure 11:
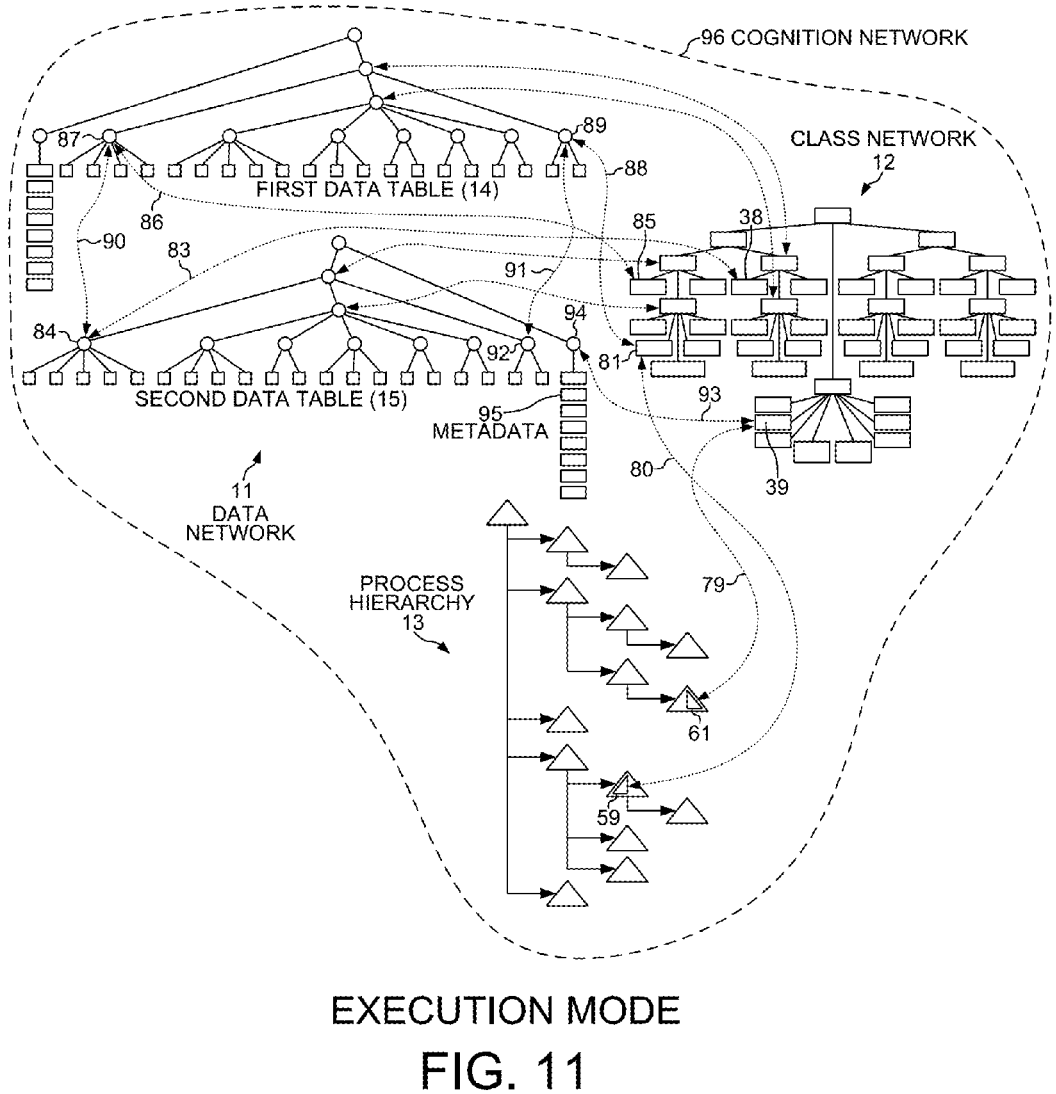
FIG. 11 is a simplified schematic diagram of the computer-implemented network structure of FIG. 1 after the data network has been generated in the execution mode.

FIG. 11 illustrates the condition of computer-implemented network structure 10 in the execution mode after the Cognition Program has generated data network 11. Various classes of class network 12 have been linked to objects in data network 11 that belong to the classes. For example, the class 38 specifying the thorax muscle in left MLO view is linked by a link 83 to an object 84 that links pixel values of the digital image of second data table 15. A class 85 specifying the thorax muscle in left CC view is linked by a link 86 to an object 87 that is linked to pixel values of the digital image of first data table 14. Similarly, subclass 81 (Mammilla) is linked by a link 88 to an object 89 that is linked to pixel values from the left CC view.

In addition, FIG. 11 shows that while the Cognition Program is running, links are also generated between classes, process steps, objects and table data. For example, object 84 representing pixel values showing the thorax muscle in the left MLO view is linked by a link 90 to object 87 representing pixel values showing the same thorax muscle in left CC view. Similarly, object 89 representing pixel values showing the mammilla in the left CC view is linked by a link 91 to an object 92 that is linked to pixel values showing the mammilla in the left MLO view.

Moreover, algorithms are linked to table data values. For example, algorithm 61 is linked by link 79 to class 39 (Weight) in the specification mode. In the execution mode, class 39 is linked by a link 93 to an object 94 for patient metadata. Thereafter in the execution mode, algorithm 61 is linked to an item of metadata 95 that contains a value representing the patient's weight. Network structure 10 is shown in FIG. 11 as a cognition network 96 when links are present between classes, process steps, objects and table data at run time in the execution mode.

Figure 12:
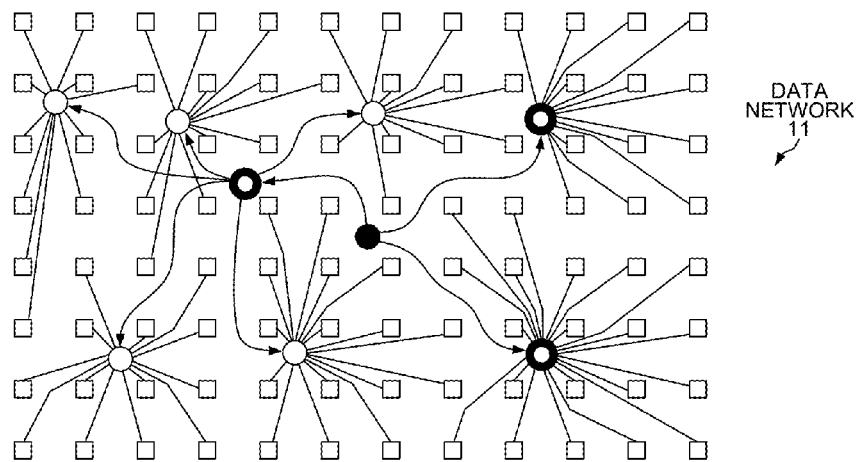
FIG. 12 is a simplified diagram of a data network in which pixel values are linked to objects.

FIG. 12 illustrates objects that have been linked to table data values having similar characteristics. In addition, objects are linked to other objects according to the membership functions that define the classes. The table data values of FIG. 12 are arranged to illustrate that they are pixel values of a digital image. For example, one factor of a membership function is the area occupied by the pixels that make up the object. In one example, the area is calculated as being proportional to the number of pixel values linked to the object.

Figure 13:
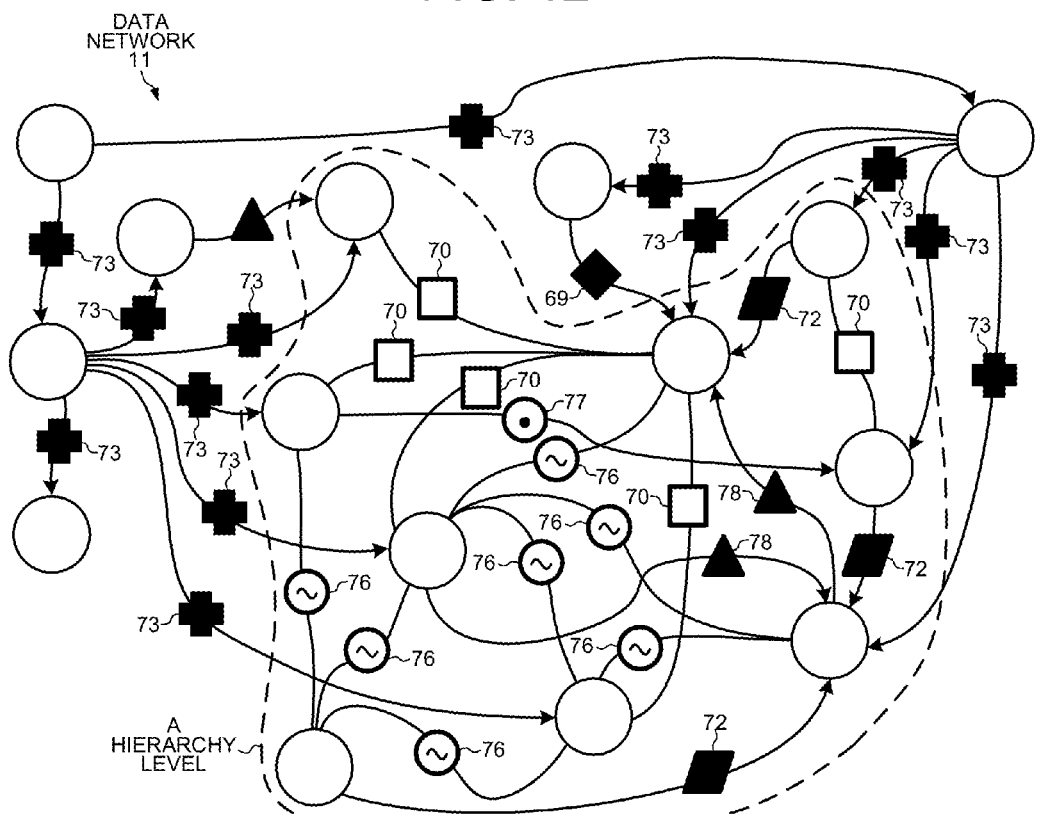
FIG. 13 is a simplified diagram of a data network in which objects are linked to other objects by various types of links.

FIG. 13 illustrates objects linked to other objects in data network 11. The objects are linked by the link types shown in FIG. 9. In the execution mode, an object that belongs to a class is linked to another object that belongs to another class when the two classes are linked together in class network 12.

Figure 14:
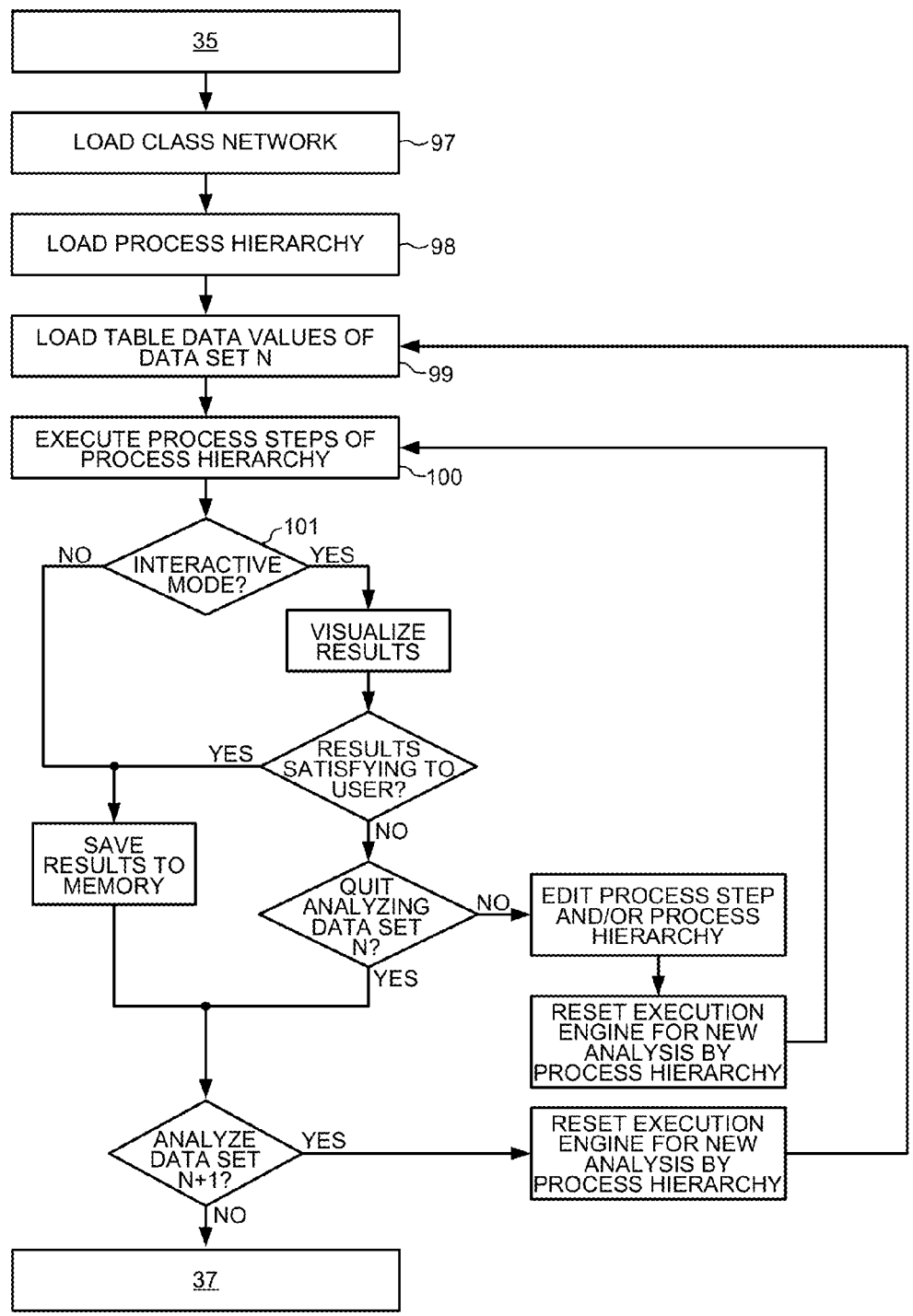
FIG. 14 is a flowchart showing the substeps of the fifth step of FIG. 3 for generating the data network of FIG. 1.

FIG. 14 is a flowchart that illustrates the substeps of step 36 of FIG. 3 in more detail. In a substep 97, the class network that is specified in step 32 of FIG. 3 is loaded into a script execution engine of the Cognition Program. In a substep 98, the process hierarchy that is specified in step 33 of FIG. 3 is loaded into the execution engine. In a substep 99, a data set N of the table data values acquired in step 35 of FIG. 3 is loaded into the execution engine.

In a substep 100 of step 36 of FIG. 3, the process steps specified in step 33 of FIG. 3 are executed on the data set N. In substep 101, the user has the option to run the Cognition Program in an interactive mode. In the interactive mode, the results of the computer-aided detection are displayed to the user, such as a research doctor. If the user is not satisfied with the results, the user can edit the classes of class network 12 or the process steps of process hierarchy 13 and immediately re-execute the process steps on the data set N. The user can edit the process steps using the graphical user interface and the script editor of the Cognition Program.

Figure 15:
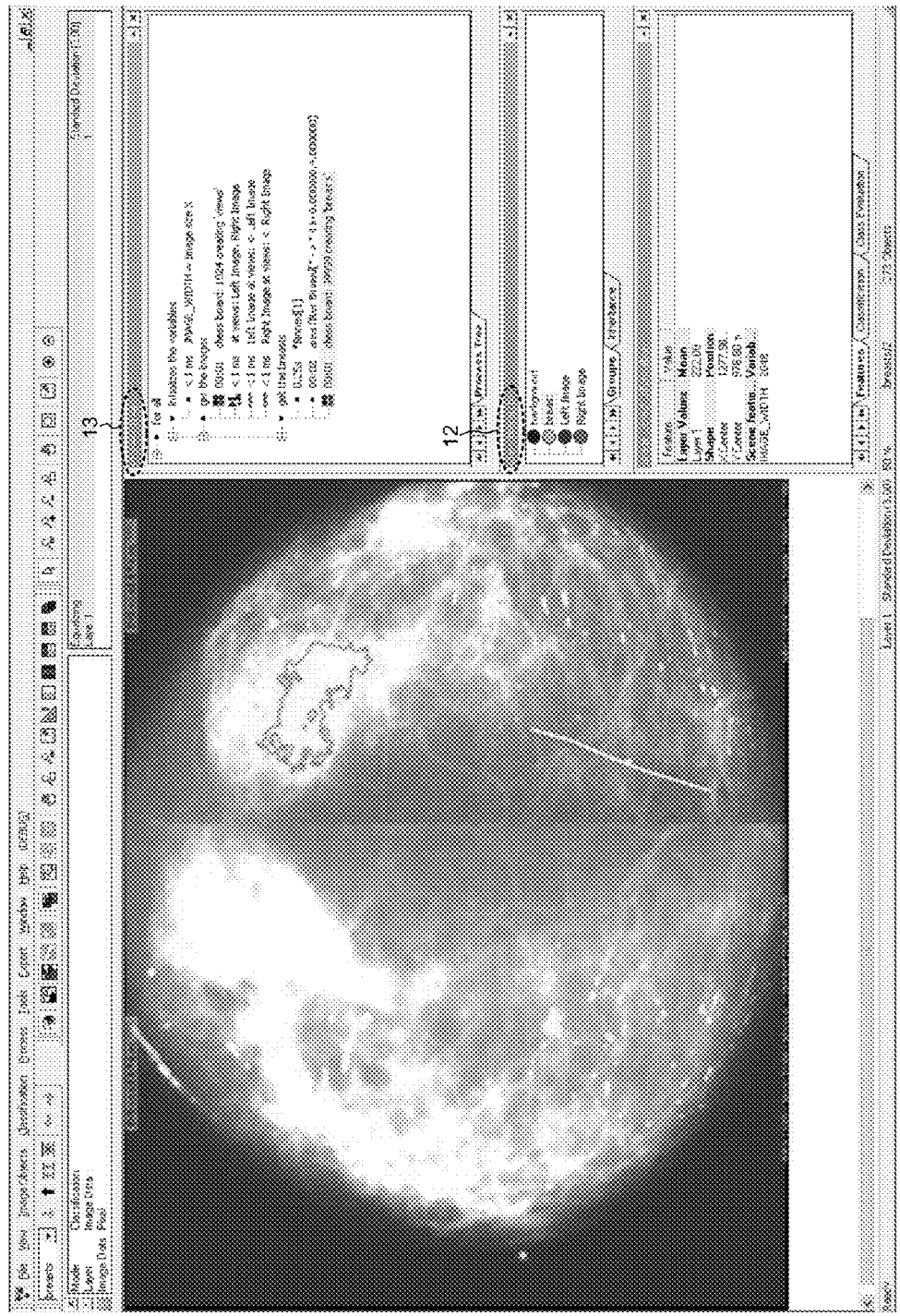
FIG. 15 is a screenshot of a graphical user interface generated by the Cognition Program to assist in the editing of the class network and process hierarchy of FIG. 1.

FIG. 15 is a screenshot of one view of the graphical user interface generated by a view module of the Cognition Program. The screenshot includes a window containing a digital image of the right MLO view of a breast with a target region outlined. The user can edit the class network 12 or the process hierarchy 13 using the windows on the right of the screenshot so that the target region recognized by the particular process step being edited is satisfactory. For example, by right mouse clicking on a process step in the upper right window, a pop-up window appears with a dialogue asking the user whether he wishes to add a sub-process step or append a process step below the clicked process step. The user is then asked to choose a domain and an algorithm for the new process step. Existing process steps can also be edited.

The user can also add or edit classes using the middle right window. A class is also added by right mouse clicking and responding to the queries in the pop-up window. The user is asked to name the new class and enter properties of objects that belong to the class, such as color, area, asymmetry, density and the angles along the border of the object. Thus, the Cognition Program can also analyze color digital images. For example, the user defines an "asymmetry function" as part of a membership function for objects belonging to a class. The asymmetry function describes the shape of the pixels that make up an object by approximating an ellipse. For example, the user can use the asymmetry function to classify objects that have shapes indicative of micro-calcifications. The numerator of the asymmetry function describes the long axis of the ellipse, and the denominator describes the short axis. A pixel shape that approximates a circle has an asymmetry value of one. An elongated pixel shape has an asymmetry value much greater than one. The user can also define a density function to classify objects that have shapes indicative of micro-calcifications. The density function is the square root of the area of the pixels divided by the length of the border around the pixels that comprise the object.

Because class network 12 and process hierarchy 13 are specified using a Cognition Language (CL) based on the XML script language, class network 12 and process hierarchy 13 can be edited without recompiling the Cognition Program. Thus, the user can input a new membership function of a new class at run time that defines whether the objects of data network 11 will belong to the new class, and the process steps can be performed immediately on the newly generated data network 11 without recompiling the program instructions of the Cognition Program. The XML-based Cognition Language and the graphical user interface allow the user to more quickly "train" cognition network 96 to recognize cancerous mass lesions and micro-calcifications in mammograms or to recognize any other desired pattern. The ability to edit the class network 12 and process hierarchy 13 at run time differentiates the Cognition Program from conventional CAD schemes that cannot change the process of applying rules once the CAD scheme begins analyzing a particular digital image. After the user of the Cognition Program determines that the results of the pattern recognition performed on data set N are satisfactory, the process steps are executed on the next data set N+1.

The Cognition Program would typically not be run in the interactive mode when the user is a clinical doctor who is analyzing a new patient's mammogram instead of a research doctor. A clinical doctor would use the Cognition Program with a class network and a process hierarchy that have already been trained by the research doctor. In that case, all of the process steps of process hierarchy 13 would be executed on all of the data sets, and the results would be saved for displaying as the final results in step 37 of FIG. 3.

Figure 16:
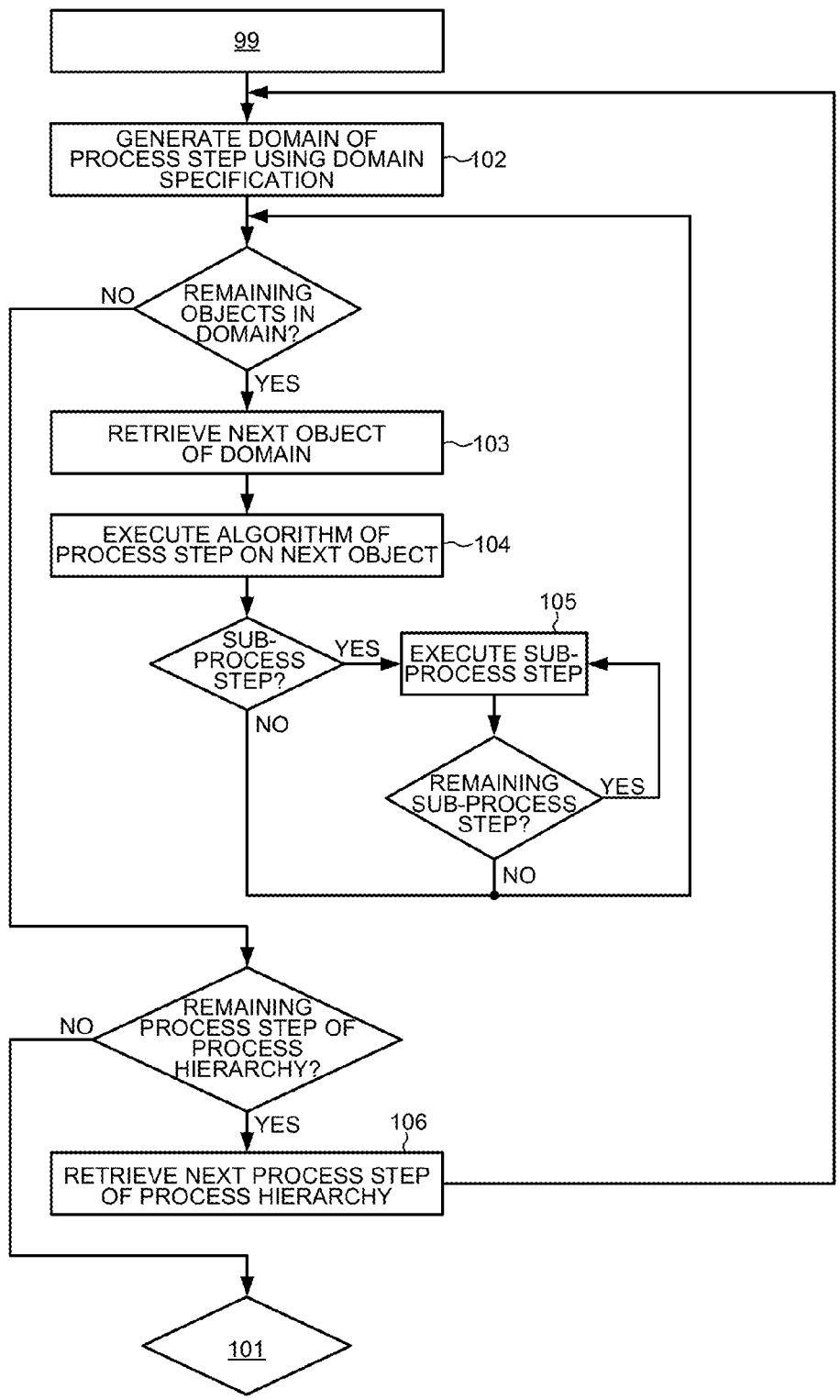
FIG. 16 is a flowchart showing the substeps of a step of FIG. 14 for executing the process steps of the process hierarchy of FIG. 1.

FIG. 16 is a flowchart that illustrates in yet more detail additional substeps of substep 100 of FIG. 14. FIG. 16 illustrates the process by which each process step of process hierarchy 13 operates on objects specified by the domain. In a substep 102, the domain that was specified in substeps 62-65 of FIG. 7 is generated. In a substep 103, the execution engine retrieves the next object of the domain that is to be operated upon. In a substep 104, the execution engine executes the algorithm of the process step on the retrieved object. In a substep 105, the execution engine executes the algorithm of any sub-process steps on the retrieved object. In a substep 106, the execution engine retrieves the next process step of the process hierarchy so that substeps 102-105 can be repeated for the domains and the algorithms of the next process step and sub-process steps, if any.

Figure 17:
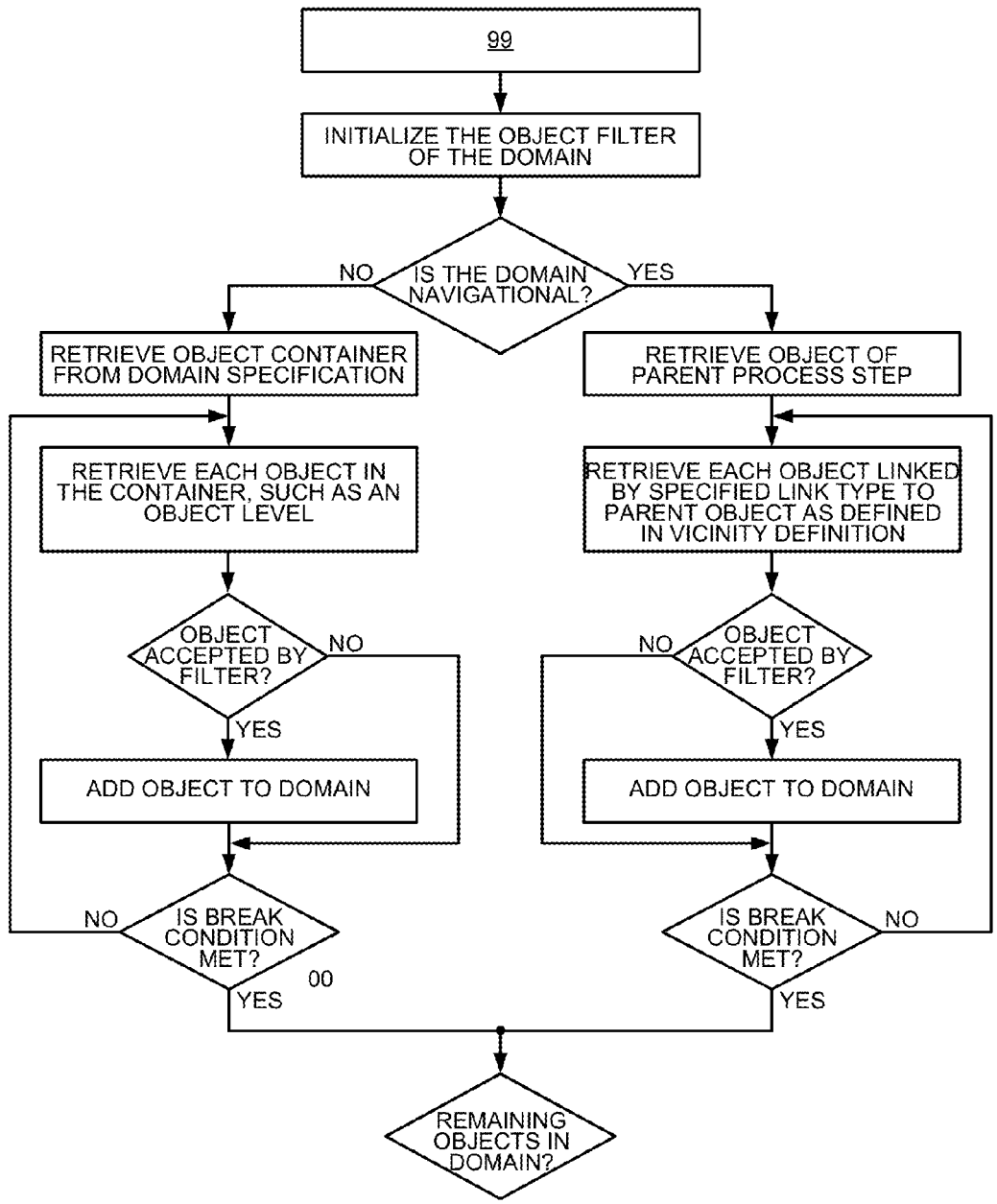
FIG. 17 is a flowchart showing the substeps of a step of FIG. 16 for generating a domain specified in a process step.

FIG. 17 is a flowchart that illustrates in yet more detail additional substeps of substep 102 of FIG. 16. FIG. 17 illustrates the process by which the domain that was specified in substeps 62-65 of FIG. 7 is generated at run time.

In step 37 of FIG. 3, the Cognition Program outputs the final results of the computer-aided detection based on the cognition network 96 that was generated using class network 12 and process hierarchy 13.

Figure 18:
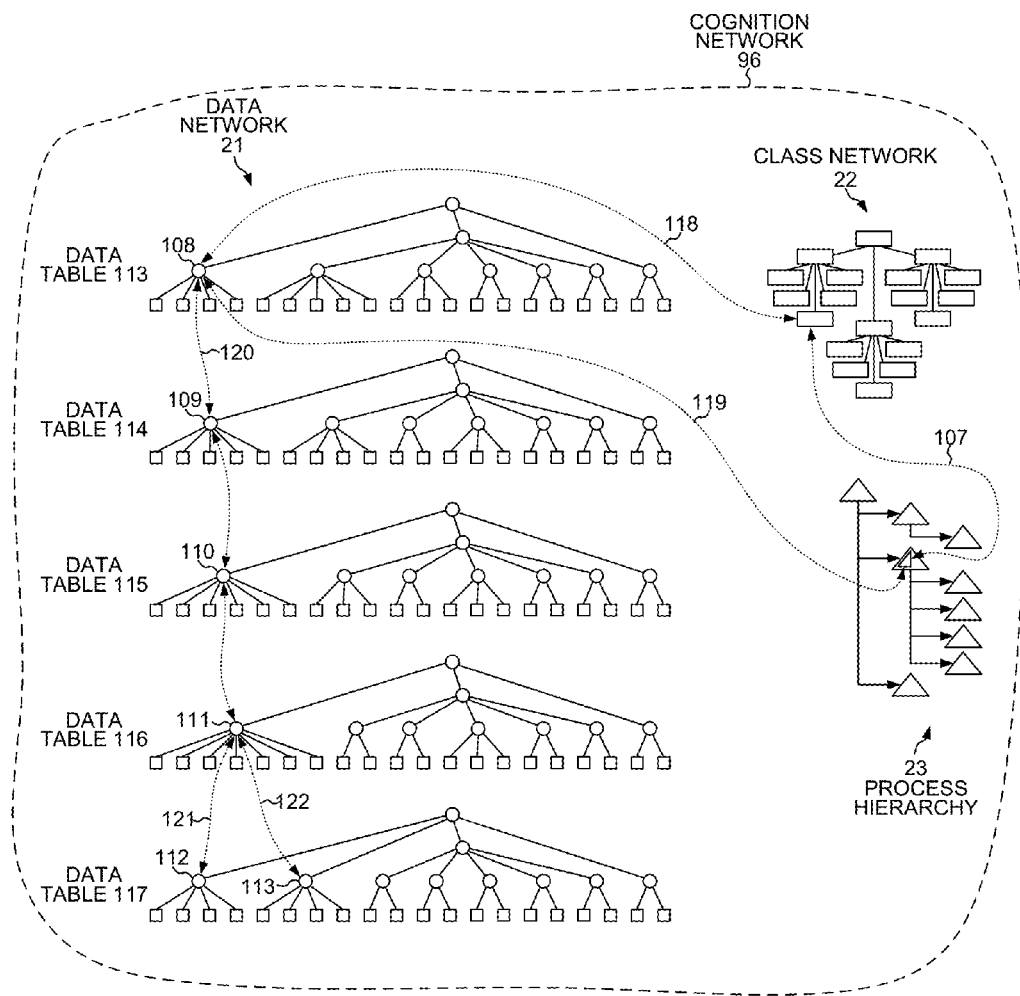
FIG. 18 is a simplified schematic diagram of a cognition network when the data network has been generated from many digital images, such as from many slices of a 3-dimensional object.

FIG. 18 shows cognition network 96 of FIG. 11 when data network 11 has been generated from many data tables, each containing a digital image. By generating data network 11 from digital images obtained from many parallel planar slices of a three-dimensional data set of a physical object, the Cognition Program detects three-dimensional target regions in the physical object. For example, the slices are extracted from a three-dimensional data set of a human breast, and the 3-dimensional target region is a cancerous mass lesion. In another embodiment, parallel planar scans are taken of a human brain, and the 3-dimensional target region is the medulla or ventricle of the brain.

FIG. 18 illustrates that in the specification mode a domain specification is linked by a link 107 to a class. In the execution mode, the Cognition Program acquires table data values comprising the many digital images that are slices of a three-dimensional data set. The Cognition Program then applies the membership function of the class to the values of each of the digital images and determines that various objects generated from the many digital images belong to the class. For example, the Cognition Program determines that each of objects 108-112 from digital images in data tables 113-117, respectively, belongs to the class. The class is then linked to each of the objects 108-112. For example, a link 118 links the class to object 108, which in turn is linked to pixel values from a first digital image in data table 113. At run time, the domain specification is then also linked to the objects that belong on the class specified in the domain specification. For example, a link 119 links the domain specification to the object 108 while the Cognition Program is running. This allows the algorithm of the process step to operate on all of the objects that comprise the 3-dimensional object. Finally, each of the objects 108-112 that are generated from the many digital images and that belong to the class are linked to each other in data network 11. For example, object 108, which is linked to pixel values from the first digital image, is linked by a link 120 to object 109, which is linked to pixel values from the second digital image.

Figure 19:
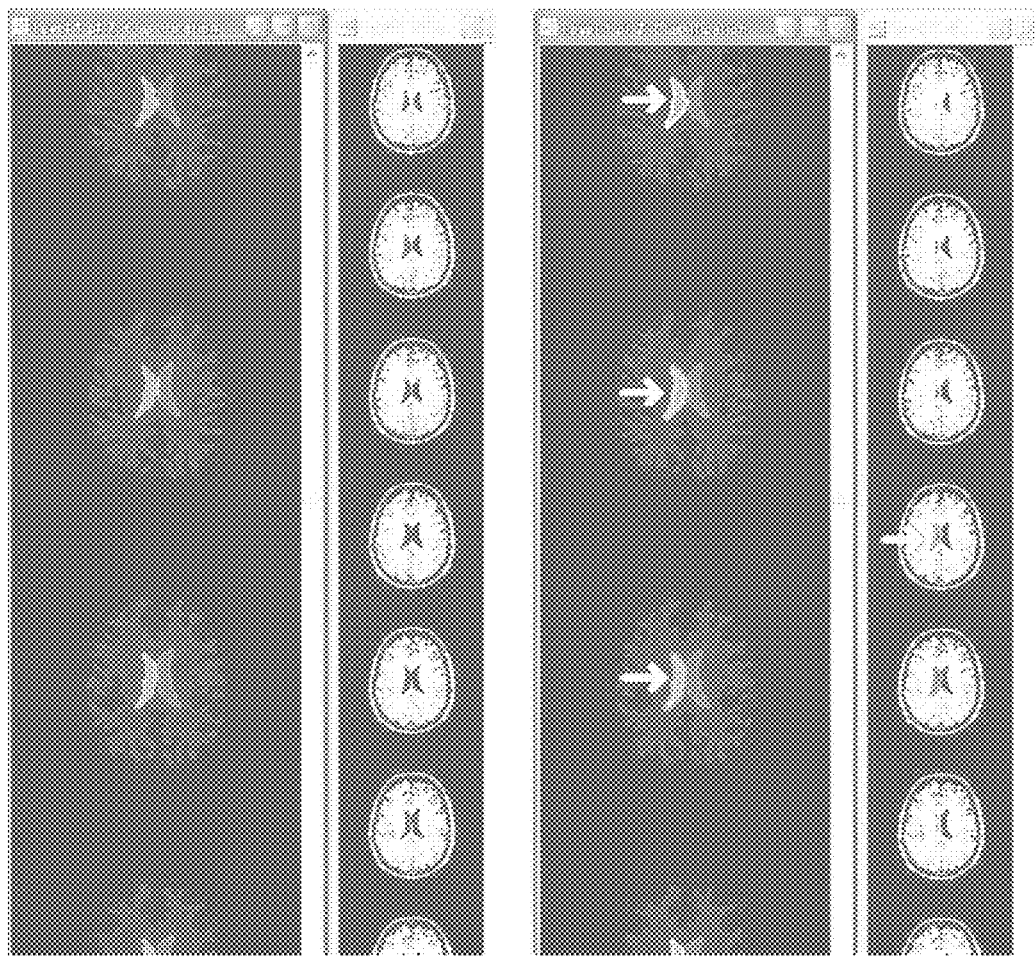
FIG. 19 is a screenshot showing images of parallel planar scans of a human brain.

FIG. 19 shows images of parallel planar scans of a human brain. The Cognition Program has detected a 3-dimensional object (a portion of a ventricle or of the medulla oblongata) by linking objects in adjacent scans that belong to the same class. The objects in adjacent scans that belong to the same class are displayed with the same color in the output of step 37 of FIG. 3.

Returning to FIG. 18, the Cognition Program has linked an object generated from one parallel planar slice to two objects in an adjacent parallel planar slice. Object 111 that is generated from the fourth digital image is linked to two objects of the same class generated from the fifth digital image. Object 111 is linked by a link 121 to object 112 and by a link 122 to a second object 113 generated from the fifth digital image. In this way, the Cognition Program is able to detect 3-dimensional objects such as blood vessels that fork into multiple portions in adjacent slices.

Linking objects in multiple scans can also be used to track movement over time. Instead of the scans representing adjacent physical planes of an object, multiples scans are analyzed that are acquired at different times. For example, the objects 108-112 and 113 belong to the class representing a cell. Digital images are taken of the cell at different time intervals. Movement can be tracked by linking objects of the same class that are obtained from digital images taken in adjacent time intervals. Over the four time intervals at which the digital images of data tables 113-116 are taken, the cell described by the class linked to objects 108-111 grows from four pixels to seven pixels. Then after the fifth time interval, the cell divides into object 112 with four pixels and object 113 with four pixels.

In another embodiment, the Cognition Program acquires the multiple digital images from a video movie instead of from multiple scans. The video movie depicts movement of an animal or a vehicle, such as a worm, a fish, a bacterium, a cell, a person, a motor vehicle, a boat, or an airplane. The Cognition Program can be used to detect a moving animal or vehicle from among multiple moving objects. For example, the Cognition Program can be used to detect and follow a specific car as that car moves in traffic in a video movie.

FIG. 20 is a screenshot of the final output results of step 37 of FIG. 3 in yet another embodiment of the Cognition Program. In the embodiment of FIG. 20, cognition network 96 has been generated using four digital image views of mammograms from hundreds of patients. Objects in different mammograms that belong to the same class are linked. In addition, similar characteristics of the metadata of patient information are also linked. In this way, the mammogram of a new patient can be compared with the most similar mammogram of a prior patient whose diagnosis was known to be valid. In this application, the Cognition Program acts as a "Cognition Integrator" by integrating four digital image views as well as patient information from each of hundreds of patients into one cognition network.

Figure 21:
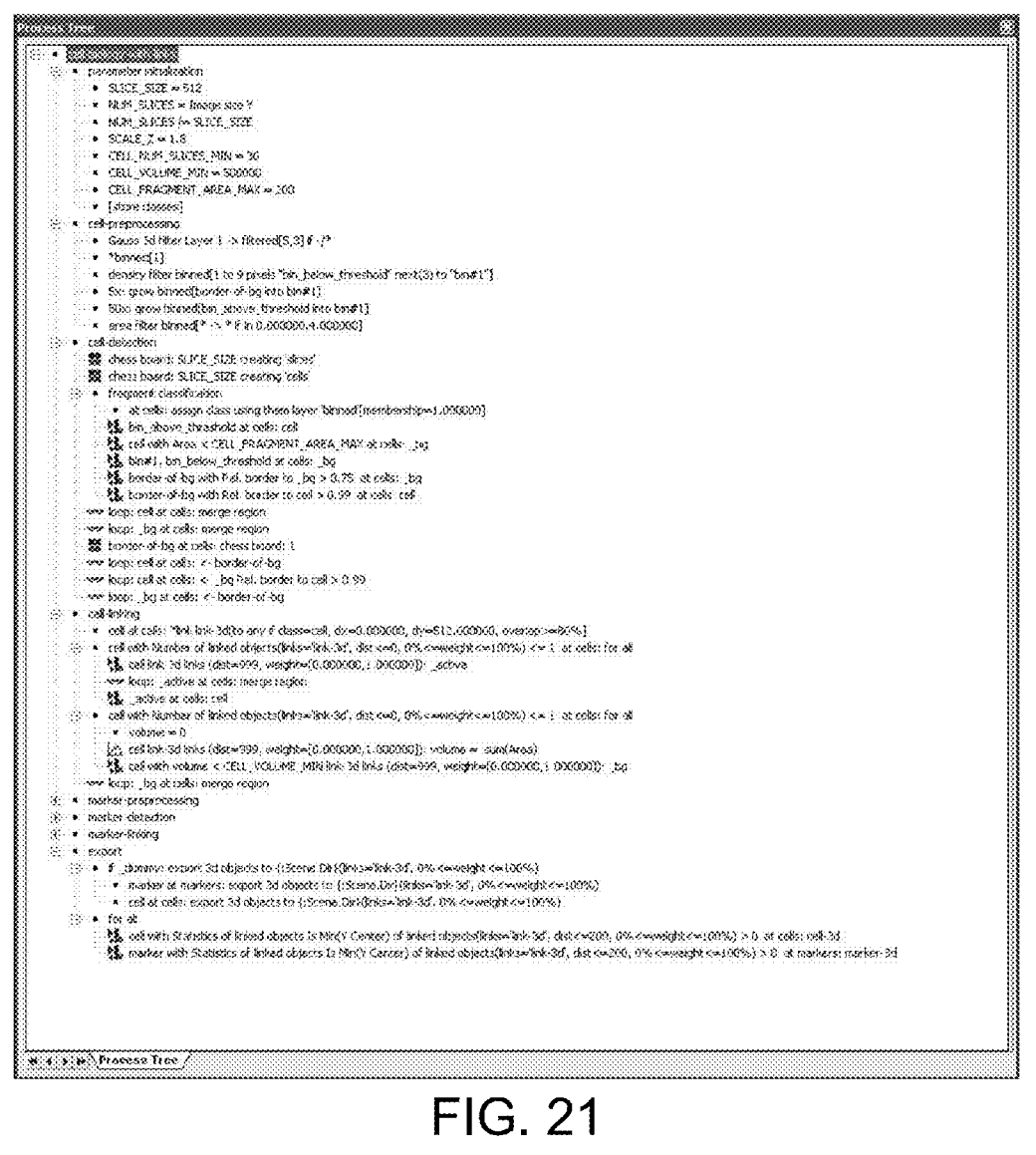

FIG. 21 is a screenshot of a process hierarchy in another embodiment of cognition network 96 that analyzes individual cells in a cell assay. Three-dimensional properties of the cells are analyzed using one hundred scans at different depths of an individual cell using a confocal microscope. During the "training" process when the Cognition Program is run in the interactive mode as described by the substeps of FIG. 14, the process hierarchy of FIG. 21 is presented to the user in the upper right window of FIG. 15.

Figure 22:
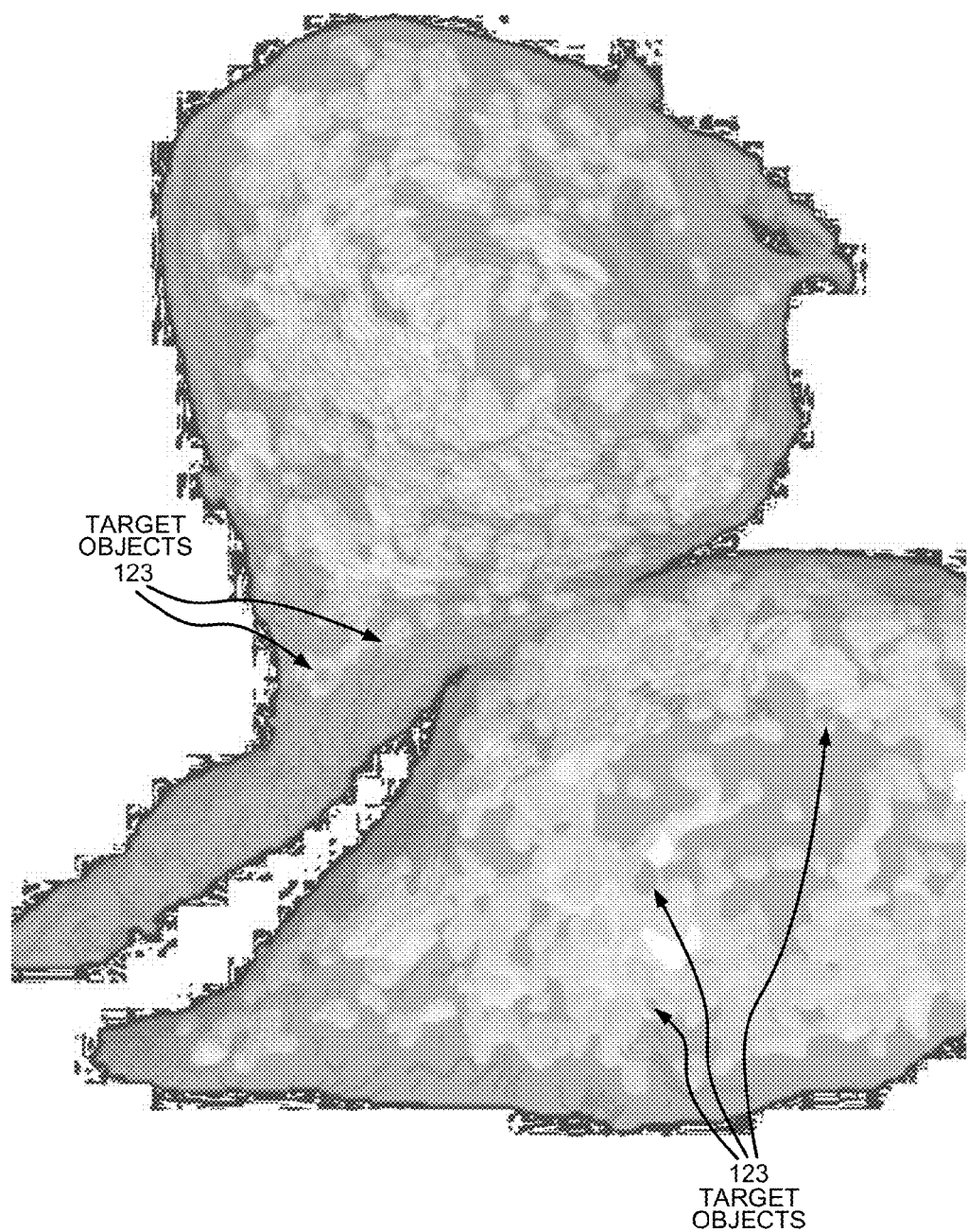
FIG. 22 is a 3-dimensional diagram of a dividing cell output in the last step of FIG. 3 with marked target objects.

FIG. 22 shows the output of step 37 of FIG. 3 as presented to the user on the graphical user interface for the embodiment of FIG. 21. A 3-dimensional dividing cell from a cell assay is depicted in FIG. 22. In the image of FIG. 22, target objects 123 that belong to the same class are displayed with the same color. In this example, target objects 123 are marked proteins. The Cognition Program compared the mean volume of the marked proteins to the volume of surrounding cytoplasm.

In yet another embodiment, cognition network 96 analyzes cells that are aggregated in tissue. Table data values are acquired in step 35 of FIG. 3 from images of cell tissue in multiple wells of a tissue micro array. The Cognition Program is used to look for morphological changes in the cells. The Cognition Program is used to detect motion in the cell tissue by analyzing multiple images taken of the same well after successive time intervals. The Cognition Program determines how long it takes for the cells of the tissue to stop dividing when a specified dosage of a drug is placed in the well.

Figure 23:
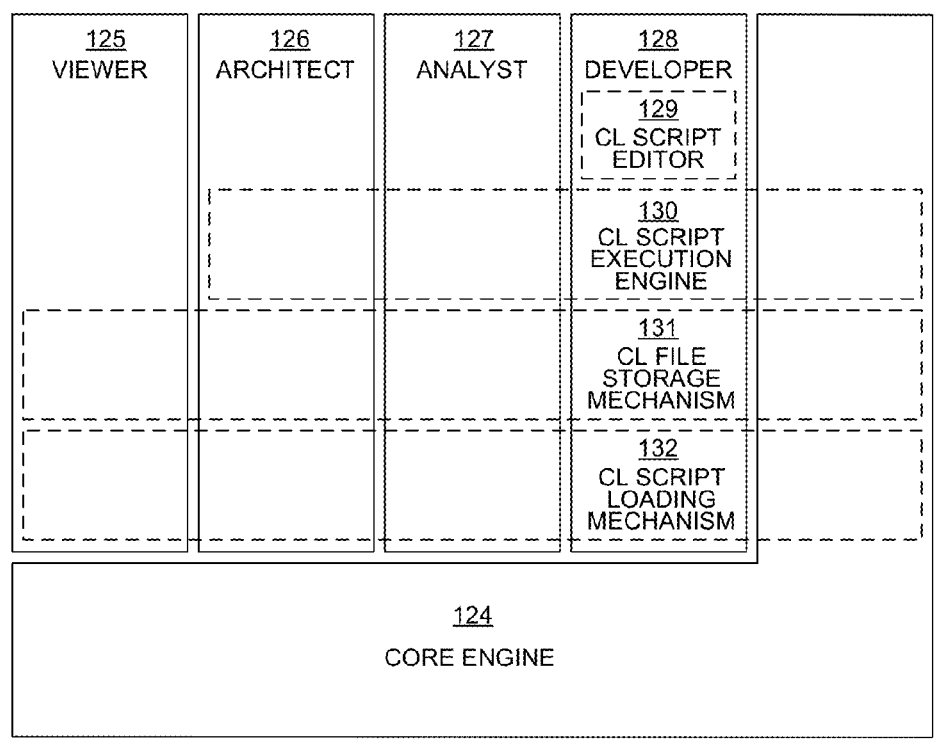
FIG. 23 is a diagram of the structure of the modules and script functionalities of the Cognition Program.

FIG. 23 is a diagram of the structure of the Cognition Program. In one embodiment, the Cognition Program consists of five modules: a core engine 124, a viewer module 125, an architect module 126, an analyst module 127, and a developer module 128. Each of the five modules is written in the programming language C++. Viewer module 125, architect module 126, analyst module 127 and developer module 128 all run on core engine 124. Architect module 126 is used to enter the required parameters requested by pre-specified class networks and process hierarchies. Then cognition networks are generated by executing the pre-specified class networks and process hierarchies on analyst module 127. Analyst module 127 analyzes data sets using the class networks and process hierarchies generated using architect module 126. Developer module 128 incorporates all of the functionality of architect module 126 and analyst module 127.

A user may create his own scripts in a novel Cognition Language (CL) by specifying a class network and a process hierarchy using a CL script editor 129 in developer module 128. CL script editor 129 presents a visual representation of the Cognition Language and allows the user to create and modify CL scripts using standard Microsoft Windows, user-interface elements, such as drag and drop, tree controls, and list boxes etc. Although developer module 128 executes the CL scripts that specify the class network and process hierarchy, the CL scripts are stored only as XML code. The CL scripts are stored in C++ data structures in memory of the computer that implements computer-implemented network structure 10.

A CL script execution engine 130 is present in developer module 128, core engine 124, architect module 126 and analyst module 127. At run time, CL script execution engine 130 translates CL scripts into a series of C++ function calls and then executes the calls. Thus, execution engine 130 interprets the CL scripts at run time. After a CL script has been executed, a CL file storage mechanism 131 translates the CL data structures to XML and saves the XML code to a file or database. Before the Cognition Program can run a CL script, a CL script loading mechanism 132 recreates the CL data structures from the stored XML files. Both the storage mechanism 131 and the loading mechanism 132 are present in all of core engine 124, viewer module 125, architect module 126, analyst module 127, and developer module 128.

FIG. 24 is a listing of high-level lines of XML code that corresponds to a CL script that implements a class network and a process hierarchy for analyzing mammograms. The CL script was created and edited using a graphical user interface similar to the one shown in FIG. 15. All of the lines of the XML code are present in an XML file entitled mamma-v002.dcp.xml and contained in the CD Appendix.

FIGS. 25A-E show more lines of the XML code of FIG. 24. The XML description of selected classes of FIG. 4 and process steps of FIG. 6 are identified by XML comments in FIGS. 25A-E. For example, FIG. 25B shows an XML description 133 of the class Mammilla 81 of FIG. 4. The class "Mammilla" is identified with the class ID of "15". In addition, FIG. 25B shows an XML description 134 of a Helper class of FIG. 4. The Helper class is a temporary class and generates intermediate objects at run time. The intermediate objects are reclassified as the Cognition Program iteratively performs the process steps to optimize the categorization of objects into the remainder of the specified classes. Thus, performing the process steps of the process hierarchy is an adaptive process that is repeated and optimized on same digital image.

FIG. 25D shows an XML description 135 of the domain specification of a sub-process step of the sub-process step 55 (Link Mammillae) of FIG. 6. The class ID "15" for the class "Mammilla" is listed under the list of classes <lClss> of the domain specification. The class ID in the domain specification generates a link between the domain specification and the class at run time. At run time, links are also generated from the domain specification of the sub-process step to the actual objects of the data network that are determined to belong to the class "Mammilla".

Figure 26:
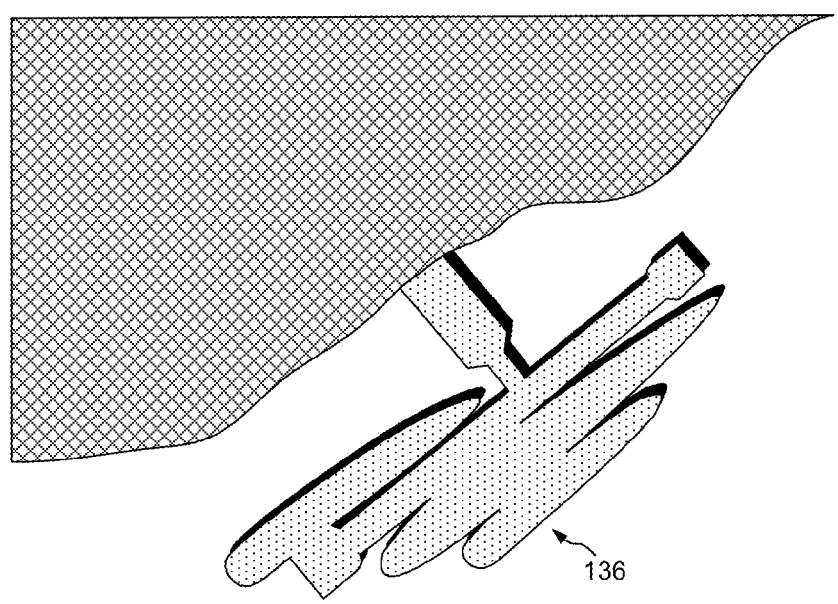
FIG. 26 is a representation of a satellite image from which the Cognition Program generates a cognition network in order to detect ships in a harbor.

FIG. 26 shows a digital image from which the Cognition Program generates a cognition network in order to detect target objects in another application. FIG. 26 is a satellite image of a harbor in which various ships are anchored. The table data values acquired in step 35 of FIG. 3 also include metadata relating to the ships. For example, the metadata includes the names of ships and their sizes, the shapes of their bows and sterns, and the distances between their bows and sterns.

The shape that is being analyzed does not show discrete ships. Each ship may not appear as a discrete object because the satellite taking the image is not directly over the harbor. Shadows from the sun also merge the outlines of the ships. Therefore, the ships and the harbor platform appear as a single form 136. In the execution mode, the single form 136 is broken apart and categorized into objects that belong to helper classes. Then the objects are merged together and categorized into other objects that belong to classes that relate to ship characteristics. For example, there is a class that corresponds to the stern shape of a particular ship. Finally, the objects are merged together and categorized into parent objects that belong to classes that correspond to individual ships.

In other embodiments, a cognition network generated by the Cognition Program is used to detect other military images, such as tanks, missile launchers, and airplanes. In addition, the Cognition Program can be used to detect roads, buildings and rivers for making maps. The digital images used as the input data can be taken from airborne sensors, such as cameras in airplanes or in balloons.

Cognition Language and Program

Automated electronic data processing has existed since there have been computers. The more complex the tasks have become, the more challenging the computer programs have become and the greater the demands are for the programmers to produce programs that run without errors. To allow the programmer to devise increasingly complex programs at all, more and more powerful computer languages had to be developed. One line of code in Java, a modern programming language, for example, is substantially more powerful than one line in machine language.

In spite of the breakneck speed of the development of programming languages, today even simple intelligent tasks can still not be performed by computers if the complexity of the task exceeds a certain mass. In fact, this critical mass is rather modest, compared to the complexity that the human mind can handle. If the relationships are simple but the data set is large, the computer is indeed superior to humans. If the relationships are complex, however, the computer generally fails at a very low level.

Complex relationships exist above all in cases where the information is formulated primarily implicitly, that is where the information can be evaluated correctly only with the help of complex knowledge. Examples of such implicit information are complex tables, text, graphs, images, films or other data types. All these cases require knowledge or even expert knowledge to allow a correct interpretation of the contents. The images on our retina and also the digital images of a camera are in the form of pixel fields. The meaningful objects in the images, which are what makes the images interesting in the first place, do not exist a priori in the images. Rather, they form only after interpretation in our brain. This process is called interpretation or cognition.

Consequently, it is desirable to produce a computer-implemented method for the automated knowledge-based production of user-relevant data, by means of which implicit information can be extracted efficiently from heterogeneous data by interpretation. Such a computer-implemented method permits (i) auto-programming and training, (ii) the automated segmentation, analysis and interpretation of complex multi-dimensional images and the possibility of a meaningful visualization of the contents of multi-dimensional images, (iii) the automated interpretation of complex table contents with automated segmentation and grouping of the contents and thus the recognition of important relationships, (iv) the automated interpretation, analysis, and indexing of complex text documents, (v) the preparation of highly complex "business intelligence" software, and (vi) the automated meaning-driven intelligence data integration and analysis of multimodal heterogeneous data (a holistic interpretation of data).

A network structure is disclosed that permits the automatic interpretation of contents in complex data by means of a computer-implemented procedure. The computer-implemented network structure enables the automatic interpretation of tables, images, texts and networks. Also disclosed is a software tool that allows the preparation of complex interpretations. A novel computer language is described for the interpretation of complex contents in data, such as tables and other structures. The internal structure of the novel computer language is based in principle on the properties of the human thought structure.

The correct interpretation of contents in data presupposes knowledge. In conventional computer programs, this knowledge is introduced implicitly by the programmer into the program in the form of algorithms. The problem with this conventional approach is that the knowledge may be distributed over the entire program, and, as a rule, it cannot be clearly located in the program. In conventional computer programs, knowledge and processes are interwoven. In very complex programs, it has become almost impossible to untangle the two at a later time. As a result, modifications of the program become difficult or entirely impossible. However, in the case of complex relationships, a perfectly running program can in fact not be achieved, and it is desirable continuously to improve the programs over weeks, months, years, and even decades. The greatest problem here is so-called transferability. Even if the problem-free running of a program has been successfully tested using a large number of data sets, problems that have not yet been addressed almost always occur with new data sets. This situation has to do with the immense number of different situations in complex relationships.

At the beginning of the existence of computers, software and hardware were also interwoven. Being able to separate the two was a great achievement, as it allowed both to be improved independently of each other. The Cognition Language analogously allows challenging and complex programs to be written, while dealing separately with the knowledge and the processes in a simple and convenient manner.

Today, neural and semantic networks represent a known method that claims to work in that direction. The knowledge is represented by the structure of the semantic network, and a computer program uses this knowledge to process the data structure. However, semantic networks should not be considered to be higher computer languages. Rather, they are simulation tools with very limited application possibilities. A computer language, even if it is unable to process all the solution with optimal elegance, should at least be capable of solving, in principle, any problem. New processes in semantic networks have to be written in a conventional computer language. In the Cognition Language (CL), several fundamental processes are predefined and implemented in a conventional computer language. However, these processes are so generic that new processes can be prepared from these generic building blocks. It is only for the purpose of continuing to improve the ease and elegance of the program writing that new generic CL building blocks, which are written in a conventional language, also continue to be added. Several other aspects, such as the concepts of domains and of navigation by subsets, are also lacking from neural and semantic networks.

The Cognition Language possesses the following properties, which enable CL to solve high-level tasks. CL is a subject-specific "high-level" language. CL is modular; CL modules (CL objects) are combined to form a program. There are input objects and CL objects. More specific CL objects are knowledge objects and flow objects. More specific input objects are input data and objects generated therefrom. Knowledge objects and flow objects can be combined into knowledge, hierarchies and flow hierarchies. Finally, the possibility of linking all the objects leads to a hierarchical network—the finished program.

The Cognition Program transforms weakly structured input data into a hierarchical network of relevant input objects. This transformation occurs via a large number of intermediate steps, in which intermediate objects, which in the end are not relevant, are generated. These intermediate objects gradually develop into relevant intermediate objects. Fundamental, general and subject-specific, knowledge is incorporated fixedly in the language. Fundamental knowledge characterizes the structure of the CL language, and the specific knowledge characterizes the special, concrete, predefined building blocks (the base modules or CL objects). Any number of CL objects can be chosen, individually given parameters and variables, and assembled by hierarchical linking into a complete program. The program flow and the results can be visualized, and thus their quality can be checked.

The CL language is structured as follows. Application-based "world knowledge" (WK) and program flows can be formulated separately. The WK and the flows can be constructed as hierarchical network structures from knowledge objects or from flow objects. Together, the WK hierarchy and the flow hierarchy constitute the program. Subsets of all the shapes of objects (domains) can be selected directly or indirectly, either manually or by means of processes. Domains are used for the local execution of processes and other algorithms. Domains can be a part of a program flow or a part of a knowledge object. An indirect selection occurs by a sequential, hierarchical selection by navigation along partially predefined or selected links. Domains can be transformed by means of processes or manually into objects by segmentation of the input, the knowledge, and the flows. Such objects are objects with higher hierarchical rank. Processes can be applied locally to domains. Flows and WK can intervene mutually on each other and modify each other mutually. Relations between partial regions of WK in the flows, as well as in the data, can be formulated and computed automatically.

The WK consists of knowledge objects, such as concepts (classes), linking concepts, concept links, labels, object descriptions (expressions), and local and global variables. The flow hierarchy (or process hierarchy) consists of computations, conditions, different types of classification and segmentation processes (the processes) and object property computations (features), as well as of a formula editor for features and variables. All objects can be linked to each other manually or by processes. Different data sets can be loaded and they themselves or their components can be linked to each other by processes. Different analysis results can be loaded, and they themselves or their components can be linked to each other by processes. Different knowledge hierarchies can be loaded, and they themselves or their components can be linked to each other. A linked, simultaneous analysis and interpretation of different or heterogeneous tables and other types of data, such as, texts, numbers, vectors, spectra, images and presentation documents, can be preformed.

All objects and links can be deleted by processes or manually. The linking of input objects with knowledge objects corresponds to a classification; the linking with a label corresponds to a labeling; and the linking with a local variable corresponds to an attribute assignment. Not only input objects, but also knowledge objects and flow objects, can be classified. The results can be exported in the form of hierarchical object networks or in the form of tables and diagrams. Tables, partial sets thereof and other data objects can be generated and deleted, or modified. For example, a new column can be added, and columns can be multiplied with each other.

Subsets of a table can be inserted via processes into other tables. Repeated program flows (loops in process steps) can be formulated. Sub-process steps can be formulated. A flow can, as a function of a condition, interrupt a loop and proceed to other flows in any position in the process hierarchy. General data, particularly names and contents of concepts and more specifically also names and contents of rows or columns of table data, can be extracted from knowledge objects via variables and inserted or used in other concepts or in flows. The names of the rows or columns of tables can be extracted via variables, and inserted and used in concepts or flows or other tables. Linked objects can be considered hierarchically higher-ranked objects that possess properties and that in turn can be linked to form hierarchically higher objects.

The Cognition Program allows the process hierarchy (program flow) as well as the results to be visualized. All structure elements can be represented graphically. The flow of the problems can be represented because it is possible to represent the evolution of the knowledge or data object. The representation of the objects can occur in the form of (transparent) coloring, which corresponds to their classification, their label or the value of a feature or an attribute. The contour of the object and its position can also be represented. The similarity of objects or another form of their membership can be represented, for example, by identical coloring.

Complex data, particularly tables, images and texts, can be analyzed and interpreted automatically using CL. CL has a structure that provides support, and makes possible in the first place, the preparation of highly complex solutions from the cognition area. In contrast to conventional methods, an evolution of objects up to a hierarchical network structure of these objects is generated automatically and stepwise from the data sets. In the process, this object structure consists only partially of predefined data blocks of the data. By taking into account abstract knowledge, the objects are rather generated based on sense criteria and not on formal criteria. As a result, it becomes possible automatically to extract sense and meaning from the data sets, such as, for example, tables. CL allows the rapid and convenient preparation of such programs with the help of the described structure elements, which are adjusted to each other.

The automatic analyses can be used by the user as a complement to his own interpretation, to help in the decision making process. The user can drastically reduce the time required for an analysis and considerably increase its quality. The table and other data here can contain heterogeneous contents, so that very different types of information for an overall evaluation can be contributed automatically to an overall interpretation.

The special structure of CL allows the automatic processing of the data. CL has three essential components: (i) the input data plus the input objects generated therefrom, (ii) the program control, and (iii) abstract and concrete knowledge about data contents, program control and knowledge. It may seem curious that a program contains knowledge about itself. However, it is only in this manner that intelligent performances similar to those of a human become possible in the first place.

The input data themselves are part of the input data, as are the objects generated procedurally from them and their links to each other. The program control represents and describes the dynamics of the program, which, once started, performs computations and structure modifications. In the simplest case, the program control structures the input data into a new form, using the abstract knowledge. In the process, subsets of the input data are determined, defined as objects with properties, and linked both to each other and also to the knowledge. In many cases, the objects are also provided with attributes by the program control.

In the general case, on the other hand, during the flow of the program control, not only the input data, but also the knowledge and the program control itself are restructured. That is, overall the program structure modifies itself as a function of input. The modification of the entire program structure becomes necessary precisely when all three components, knowledge, data and program control, have to adapt to each other to guarantee a sensible program flow. This circumstance exists, for example, when new knowledge and new processes have to be generated automatically from the data, that is when it is impossible to predefine every possible situation in the input data in the form of a concrete program structure and knowledge structure. Instead, they are first generated via program control steps. In this manner, (i) a program can be adjusted even more flexibly to input data, and (ii) a self optimizing program (knowledge plus program control) can thus be prepared that optimizes itself only on the basis of a training data set, and that is then set fixedly in this optimized form and allowed to run with other new data sets.

A novel programming language allows the rapid and uncomplicated programming of the procedure described above. This object-based language includes three fundamental types of objects: input objects of the data network, flow objects of the process hierarchy and knowledge objects of the class network. Flow objects can be associated with mathematical expressions. In addition, there are objects that are subordinated to these three objects.

Types of flow objects of the process hierarchy include structuring processes (called processes), selection processes (called domains) that determine the subsets of the entire object set, and variables. Processes generate, delete and modify objects and links in the entire program structure. Domains generate, modify and delete partial sets of the entire program structure. The processes are linked with domains and are then active only on the subsets of the domains. Global and local variables are used to extract data, such as strings, numbers, vectors, curves and tables, at certain places of the data network, the class network and the process hierarchy of the program structure. The extracted data is then used at other places or stored for later use by linking to objects.

The structure of the Cognition Language models an evolutionary process of cognition and interpretation. The data network, the program flow of the process hierarchy and the knowledge of the class network adapt successively to each other. In an automatic learning process, the structures of the knowledge and of the program flow adapt to each other and can then be reused with new input data sets. An interpretation process detects the "data object of interest", which is generated in the execution mode by linking the original objects to hierarchically higher objects.

The structure of the Cognition Program promotes the learning and interpretation processes by automatically segmenting the input data sets into hierarchical networks. The hierarchical networks are linked automatically with knowledge objects from the class network and with other objects to form a holistic cognition network. The linking of the cognition network changes dynamically during the program flow. The Cognition Program allows a navigational procedure in the multimodal network of objects for finding partial networks, subsets of the cognition network. This allows classification and segmentation processes to run locally on these partial networks. The Cognition Program also allows inter- and intra-network communication with the corresponding processes using variables.

During the execution mode, the Cognition Program automatically prepares links between objects and thereby generates hierarchically higher ranked objects. The Cognition Program provides the hierarchically higher ranked objects with characteristics, classifies them, and then links them again at a still higher level to other objects. The hierarchically higher ranked objects are used for rapidly finding target objects. The Cognition Program first finds more easily findable starting objects and thereby more rapidly reaches hard-to-find objects via established links. Detecting hard-to-find target objects is faster using links in a hierarchical data network than using a process-based procedure such as indexing. The links of the data network are not predetermined in a fixed manner. Rather, the links are formed based on the structures actually present in the given data sets. Thus, the Cognition Program automatically creates and deletes links between the subsets of the data network that are generated from heterogeneous, multimodal data.

The creation and deletion of the links of the data network are performed using a network navigational procedure that is capable of functioning in a multimodal manner. The links that are created automatically in the cognition network are first defined by the user navigationally along different objects and links. In addition, these new links and also the generation of new objects again generate new navigational paths. In this manner, the cognition network grows, while at the same time also being partially taken apart again. This process of building up and tearing down links is similar to the development of the human brain. In this process, both the existence or nonexistence of nodes and links, as well as the existence or nonexistence of lateral branches of a navigational path determine whether the path continues or is interrupted. A part of a navigational path can also consist of mathematically or logically linked conditions, nodes and edges of the cognition network. For example, some of the links contain mathematical operations, such as "and", "or", addition, subtraction, multiplication and division. At the end the navigational path, or even at an intermediate step of the navigational path, segmentation processes can be performed. The segmentation processes are applied to objects at some point along the navigational path or to subsets of objects determined from that point on the navigational path.

If the path is interrupted because a condition of a process step is not satisfied, then the subset for all subsequent process steps is set equal to the empty set. If the navigational path is continued up to the place of the process step, the subset of objects located by the process step of the navigational path is considered the "subset of interest" for the connected segmentation process of the domain of the process step. Subsequent process steps and sub-process steps are then applied to this subset of interest. Segmentation process steps generate and/or delete objects, links, and the groups of objects that are specified by domains. Segmentation process steps operate on objects, links, the objects of a domain, the segmentation process steps themselves, local and global variables, classes, labels, and objects generated from the data sets by combining their elements. The links that are operated upon include both the predefined links that are specified as part of the process hierarchy, as well as the links generated by the segmentation process steps. For example, where the input data sets are image objects, the predefined links include links to the direct geometric neighborhoods in the form of neighborhood lists or geometric hierarchical links. Both pre-specified and automatically generated links can be applied to other links, classes, objects, processes steps, and attributes and characteristics of nodes. Where the input data sets include image objects and metadata, process-driven links can be applied to heterogeneous objects. Thus, objects of a domain can be linked in an uncomplicated, automated manner with the objects of another domain or even with domains of a different type. An example of a segmentation process step that links objects of domains is: "link the object of the starting subset of objects of the navigational path with the objects of the final subset of objects of the navigational path."

By generating links and domains in this manner and by navigating through heterogeneous objects, table data entries, image objects and text objects located in very different places in the cognition network can be linked together. These heterogeneous objects can even be automatically linked to each other at run time in an abstract manner that is independent of the input table data. Links that have been defined in the training phase of a cognition network can be used again later for navigating through the cognition network and for defining and generating new domains and links.

Groups of linked objects can be characterized as objects having characteristics and can be linked as a group to other objects at a higher hierarchical level. In this manner, it is possible to combine objects representing two-dimensional layered images by linking objects in different layered images to form three-dimensional objects having properties such as volume. In addition, non-adjacent objects within a single image that have a relationship to each other can also be linked. For example, the object comprising the elements of a dotted line can be assigned a characteristic, such as length. Such higher-ranked objects can then also be linked to classes, local variables, text data and other table data. Even non-adjacent table values can be linked to form higher-ranked objects with characteristics. A table data value may acquire a special meaning as a result of connections to other table data values.

Within the Cognition Program, communication takes place through links and through variables. Expressions are small mathematical partial networks that are assigned a name and are linked by their name to any place in the Cognition Program. Links specified using a formula editor can be established between all the mechanisms of the cognition network, such as user-specified class descriptions, process steps, sub-process steps, domains, algorithms, threshold values, characteristics, and all of the possible mathematical and logical operations, such as addition, subtraction, multiplication, division, log, exp, sin, not-and and not-or. Using the formula editor, the user assigns a name to each expression and can reuse the expression at any place in the Cognition Program. The user can also assign names to subroutines of process steps (partial program flows) and can use the subroutines as customized algorithms. In addition to linking a class to a process step, the user can also embed a customized algorithm within a class specification. This allows the user to specify a class in more detail than by generating a cognition function by mathematical linking. By embedding a customized algorithm in a class specification, the user can write a subprogram in Cognition Language for the computation of a complex characteristic of the class.

Embedding a customized algorithm in a class specification represents a "higher cognition function" that is not programmed in C++ but rather in Cognition Language. Expressions can be formulated independently and used at different places. Generating an expression using the formula editor and thereby embedding an algorithm in a class also allows the user more clearly to separate program flow from knowledge by avoiding a link between an algorithm of a process step and a class. Yet communication between program flow and knowledge can nevertheless be independently improved. In some applications, it is advantageous to split a class description into several expressions. In an image analysis application, for example, a class description can be split into an expression with a shape description of the object and another expression with a color description. It may also be advantageous to specify only partial aspects of a class description at different places in the Cognition Program.

The separation of program flow and knowledge is particularly helpful when the Cognition Program is being trained to be adapted to a new type of input data set but for an existing application. In this situation, a professional Cognition Language programmer would change as little as possible to the process steps of the program flow and primarily adapt the expressions in the classes to the new type of input data set. Then a user of the Cognition Program solution, that is a non-Cognition Language programmer, would be in a position further to adapt the Cognition Program solution merely by optimizing the expressions to the new data sets without having to understand the program flow. Changing the expressions is simpler than changing the program flow. But because the expressions are used when a process step operates on a class, the user has indirectly modified the program flow without having noticed it at all.

The Cognition Language includes arithmetic/logic expressions and procedural expressions. Expressions have unique names. Arithmetic/logic expressions are formulated as formulas and include "ClassDescriptions", "CustArth Features" and thresholds. These expressions allow the definition of rules, their logical linking, as well as mathematical operations, such addition, subtraction, multiplication, division, log, exp, and sin. Procedural expressions are formulated in the process language and include "CustAlg" and "CustRelationalFeatures".

Arithmetic/logic expressions can be used as features or fuzzy conditions. A feature is computed as a property of an object. Features include "ImageO", "returns double", link, class, and process step. Fuzzy conditions include thresholds, which are simple special cases of a fuzzy condition. Procedural expressions can be used as features, algorithms, domains process step and fuzzy conditions. An example of an algorithm that is a procedural expression is an algorithm that modifies the network structure by generating, modifying or deleting objects, links or attributes. A feature that is a procedural expression computes a characteristic of an object, such as "ImageO", "returns double", link, class, and process step. A domain that is a procedural expression describes a set of objects on the basis of the network structure, taking into consideration a current processing state. A threshold is an example of a fuzzy condition that is a procedural expression.

A domain specification includes a description of a local or global network structure, as well as an expression, such as a fuzzy condition. A local network structure includes current objects, neighbors, super-objects and sub-objects. A global network structure includes all the objects, all the classes as well as the image object level A class can store an arbitrary number of named expressions. Classes can have predefined names. Classes are used to classify the current class description of objects. Classes can perform a segmentation process on the objects or a generalization process on the objects.

The Cognition Program can perform class centric development. For example, class centric development can be performed on all objects at the image object level that exhibit a membership to the expression "nuclei.classify>0.2: assign nuclei". Class expressions can be addressed via "class_name"."expression_name". Class expressions can initialize placeholder expressions. In addition, class centric development can be performed on all objects at the image object level that are assigned to the expression "nuclei: apply nuclei.generalize".

A second type of program-internal communication occurs by means of variables. The variables can be understood to be containers that take information from program objects and links and make the information available to other program objects and links. The information can also be stored in the other program objects and links. In the case of storage, the variables are local variables or object variables. Where the information is made available to the other program objects and links, the variables are global variables or scene variables.

Global variables primarily have the task of program-internal communication. Local variables, on the other hand, primarily store a result once the result has been determined, linked with objects of the cognition network, and made available for later communication. The storage of results in objects or links can have several purposes. On the one hand, the computational effort required to compute a result can be very large, and the result may be needed at several places of the program flow. If the values are stored locally, the computation need be carried out only once, and the values can always be retrieved again. On the other hand, it may be the case that a new computation of the results at a later time in the program flow is no longer possible. Because the entire program object network is dynamic and relationships and objects of the cognition network change continuously, the results of computations will also change. However, old results can be important, for example, if the evolutionary history of an object is used as a foundation of a segmentation decision.

Global variables are used most effectively with corresponding segmentation processes when the contents and values of the global variables can be extracted, used or stored. Therefore, global variables should be capable of receiving all the relevant data in the program network. Accordingly, the extraction, use and storage of global variables should be such that these actions can also be formulated as segmentation processes. For example, access to the class network must be possible in order to allow changes in the class network to flow automatically in the process hierarchy. In text analysis, it must be possible to write the names of the classes (or the concepts in the ontology) as a string into a variable and to compare this string with the text contents, or the words, of the text input data.

This procedure contains two types of process steps: "write class name as a string in a variable" and "compare in the form of a condition" the content of the variables with text objects. Examples of the condition are "equals" and "fuzzy comparison". At first glance, this procedure does not seem to make sense because one could in fact use the class name directly in the program flow, without having to involve the class network. However, this presupposes that the Cognition Language programmer knows all the entries of the class network, including future ones. Requiring the Cognition Language programmer to know all entries in the class network, however, is undesirable. As already mentioned above, the class network can change at run time. In that case, one would not want to have to look at all the corresponding places in the process steps of the process hierarchy to change all the corresponding entries of the class network there as well. The Cognition Program allows this to take place automatically. The updating of the entries of the class network in the process hierarchy is implemented via navigation and domains in the following manner, as explained using the example of a text.

Just as one can process only certain objects in the input data selectively over the domain without knowing precisely which ones occur very concretely in a concrete analysis, or which ones can only be formed by segmentation process, one can also find and process unknown classes, processes, domains, expressions or variables via the described navigation. For input objects, one frequently uses navigation through classes and expressions. All input objects that are linked to a certain class and satisfy certain conditions represent the domains and are processed further. Thus, the navigation here proceeds from classes via classification links to the input objects. One can also proceed similarly for classes if one navigates from more abstract classes to more concrete classes.

For example, if at a place in the process hierarchy for analyzing a text that refers to proteins from a cell biological point of view, protein names should be interpreted automatically. Then one should also be able in the program to handle the abbreviations of the proteins. These abbreviations typically consist of only three letters and thus are very ambiguous. It is possible now to look up all the abbreviations in the input text, without knowing them in advance. The abbreviations only have to be linked in the class network with other and finally more abstract classes. Then, the navigation and thus the definition of the domains can be carried out via these links. Thus, if the abbreviations that occur in the input text are also mentioned in the ontology and connected, then one can reach this partial set of words in the text. For example, an abbreviation may be connection via hierarchical links to the class and the concept "protein", and one can reach the abbreviation as a domain, by navigation "to all the proteins," followed by the hierarchical link "is special," and with the condition "number letters <4,". Then, via the segmentation process, one can establish the classification link between the class "protein abbreviations" and the protein abbreviations that occur in the input text. After the initial steps, many of the links may be incorrect because abbreviations of other terms are also linked. Later, however, other processes can be used for correction.

Various types of process steps are used for generating classification links. A classification link can be generated by a fixedly installed "string match" process if the class name agrees with the name in the text. Or a variable can be provided with the name of the concepts as "values", and the abbreviations can be provided with a label under the condition "value of the variable=word string." This labeling is a forced classification because the abbreviations can now be found again very rapidly via the links that have been established with the labels. For example, labeling with the name "abbreviation of proteins" functions like an index. An example of a simple formulation of the domains is: go to class "abbreviation of proteins" in the class network and then via classification or labeling links with the input objects. Those program flows that are established specifically for abbreviations can all run in this domain, which can be found very rapidly due to this quasi indexing procedure.

In this context, the variables need not to be only numbers or strings. When training a program and also during the normal program flow, it is appropriate and more convenient also to allow tables, vectors, variable sets, and even data blocks, such as images or texts, to be the contents of variables. This permits the program-internal communication of these data. A set of variables, like all variables, has a name and constitutes a set of variables plus their values.

In this sense, a representative image or a pattern outline of an object to be found in an image can represent a local variable in the class network (the knowledge hierarchy). If needed, this variable can be retrieved by navigation, transported to certain image objects, and used there for a segmentation process. An example of such a segmentation process is classification by determining the best scaling and rotational variations of coverage. The same applies to tables or texts or other data, such as, DNA codes. Table examples, text examples and a DNA code example can be used as a sample and compared with a concrete input object that has already been segmented. This segmentation process step of comparison is then usually not merely simple matching, rather it is a match that allows for distortions.

During the automatic or semiautomatic training of the Cognition Program, the desired final results are communicated in any form to the program. By a hierarchical annotation, a user can establish which type of objects are to be found. This can also occur interactively, where the user then applies certain processes with varying parameters to a data set. The user may manually label objects. After the user specifies which objects are to be found, the desired objects are generated. The automatically found, correct, objects can also be labeled by the user. The program can then automatically extract parameters from these labeled objects and carry out new process steps with these parameters. The new process steps, in turn, lead to objects that also can be labeled. Finally, at the end of this action, a parameter set is available that represents an optimized process hierarchy as determined by the optimal agreement with the labeled objects (best overall classification of all the objects). In these parameters, segmentation and flow parameters (also classification) can be contained for all the objects. As a result, it can also be established which expressions, classes and process blocks should be active, and in which sequence. It should be noted that the cognition network contains characteristics for all the objects. Thus, for an auto-learning Cognition Program, segmentation processes or blocks must be classifiable based on characteristics, such as process run time.

In some case, a large number of parameters must be trained because a plurality of objects are to be found, as opposed to just one type of object (one class). Consequently, if the number of the parameters is immense, it makes sense to structure variables with their values hierarchically in the form of groups having their own names. Parameter sets, however, are more than hierarchically structured variables because different parameter sets may contain the same variables with different values. Such a parameter set is an n-dimensional vector with a number n of values with freely selectable dimensions (represented by the names of the variables). If a parameter set is activated, the values of the set are automatically written into the associated variables. This means that at different places of the program flow different parameter sets can be active. These different parameter sets may have the same variables with different values.

The contents of table data can be automatically interpreted using knowledge-driven segmentation. In the case of a table calculation, the Cognition Program automatically generates non-predefined sense objects and sense relationships between subsets of the data. The objects and links that are generated automatically can be written in the class network, a knowledge structure. Sense objects can also be objects whose sole function is to be intermediate objects that permit the segmentation of the actual objects. The type of the objects that are to be segmented can thus automatically be formulated in an abstract manner in the form of a hierarchical knowledge network (the class network) separately from the remaining process flow (the process hierarchy). Thus, the table calculation performed by the Cognition Program differs dramatically from conventional table calculations.

Automatically generated links are used for classifying and rapidly locating sense objects to be processed. A sense object can be a non-predefined segment of a row or a column. In addition, a sense object can be merely an abstract object that is described by the class network and defined by the process hierarchy and that consists of hierarchically linked rows or columns or segments thereof. In a multimodal approach, such a sense object consists of multimodal parts, such as an image, a text and table segments.

The already existing cognition network is required for this purpose. In addition, special, table-specific structures are also needed. These special structures include optional transformations of tables into images with thematic planes. The special structure are able to process tables in the same cognition network as the images. This simplifies the data integration and the operating ease because most functions are needed only once for both applications.

Transferring sense objects from one data table into a new data table makes the processing of table data more user friendly. For example, sense objects can be transferred from images generated from data table plus thematic levels. The following segmentation process steps can be used: (i) "generate empty table with row length x and column length y", (ii) "define sense object Y (table subset) as sense table Z", (iii) "write sense table in local variable LV", (iv) "fill empty table with contents of LA", and (v) "write contents of LA into empty data table in positions x, y". Therefore, variables are also able to contain tables, in addition to numbers and letter strings. It is also possible, although more cumbersome, to transfer each entry using domain navigation of the sense object to the desired place in the empty data table. In that case, it is sufficient to have string and number contents of variables.

In table calculations, as in image analysis, conventional processes, such as averaging or edge filters, are also used by the Cognition Program. Multiplication of rows and columns with each other, or general mathematical operations applied to rows and columns, as well as resorting of rows and columns, are available as segmenting process steps.

It is possible to structure tables hierarchically via domains and navigation. For navigating, the following types of formulations are possible: "go to the column with a name XYZ and with a characteristics expression column length=10 and column average<100, from there go to the left adjacent column, from there along the hierarchical link 'is a part of' to the super-object and from there along all the links 'has parts' to all the sub-objects." This subset of the table, which is located at the end of the navigation, represents the domain on which a segmenting process step named "find the table entry in the domain with the maximum value" can occur.

The classification of sense objects formulates classes from sense objects with expressions as contents (or classes linked with expressions). The Cognition Program can formulate the following expression: "sense object ABC has, as sub-objects, the objects which are classified as KLM and those classified as NOP with the characteristic D of the KLM object <5 and the characteristic E of the NOP objects >100." Fuzzy characteristics can also be formulated.

By linking two-dimensional object, the Cognition Program automatically segments, analyzes and interprets complex three- and multi-dimensional images. In addition to the usual three-dimensional segmentation processes, the Cognition Program can segment into layers and classify a four-dimensional image comprises of a three-dimensional image that changes over time. The Cognition Program then generates three- and four-dimensional objects by linking two-dimensional objects. This process is evolutionary and involves switching back and forth from the analysis of two-, three- and four-dimensional objects. The layered structures can be represented as an image with different tiles, or as a number of images that are sorted or labeled based on their geometric, four-dimensional, position. Characteristics are defined that automatically link two-dimensional objects to form three- and four-dimensional objects. Examples of such characteristics are the volume or the velocity of an object.

The intelligent segmentation of multi-dimensional images provides the ability to visualize the image contents in multi-dimensional images. The different objects of interest can be represented in different colors in three and four dimensions. The less interesting objects can be represented transparently as desired.

The Cognition Program performs automatic data integration by linked, simultaneous analysis and interpretation of different or heterogeneous table data and other types of data, such as, texts, numbers, vectors, spectra, images and presentation documents. The Cognition Program even analyzes structures internal to the Cognition Language, such as concepts and program flows. Diagrams are generates for visualizing the results of the Cognition Program.

The Cognition Language is a new computer language for preparing auto-learning programs. As already mentioned above, the input data can be annotated and the training results (learning results) can be stored in the form of tables or parameter sets. No other specifications of the Cognition Program are needed to store the training results, exception is the case of extremely complex parameter sets. If the number of the parameters to be tested is very large, it is no longer possible to run through all the combination possibilities in a reasonable time. In that case, the Cognition Program uses evolutionary and genetic algorithms.

The Cognition Language has the following properties:

1) The language is expanded to include global variables, which can transport, with the help of appropriate process steps, information of different types (such as strings, vectors, tables) between and within the class network (the world knowledge), the process hierarchy and the input data. Thus global variables can transport information between all objects of the cognition network.

2) The language can segment and classify process steps and classes.

3) The language can generate links between all of the objects of the cognition network in a process-driven manner.

4) The language processes linked objects as hierarchically higher ranked objects that possess properties. The higher ranked object in turn can be linked to hierarchically higher objects.

5) The language allows the Cognition Network to specify a domain as a subset of the class network or a subset of the process hierarchy, taking into consideration links generated by the Cognition Program.

6) The language can operate on heterogeneous tables of all types, including tables with business intelligence. The operations that can be performed on the heterogeneous tables include subject-specific processes and computations based on object characteristics.

7) The language can process n-dimensional images and tables due to the possibility of loading several images or tables and linking them and their objects procedurally. In addition, an image can be loaded as a table.

8) The language provides the Cognition Program with the ability to load and process multimodal data by multimodal navigation and domains. Thus, the Cognition Language has the ability to exclude very heterogeneous subsets from multimodal data by multimodal navigation. Segmentation process steps can raise multimodal domains to the level of objects, and the latter can be further segmented and classified with multimodal expressions and characteristics.

The cognition language makes it possible to prepare software solutions for the interpretation of complex data sets. It is constructed specifically for problems that do not have unique solutions. An example of a unique solution is the sum of a column in a table, or finding the largest numerical value in the table (which may be represented in one or more entries). All the computers in this world, unless they are defective, will reach the same result for the same table. However, in cases where the number of the calculation operations required for a unique result becomes unmanageably large, new solution paths have to be taken. The question "what is the optimal move in a given situation of a chess game?" is answered differently by different computers. Considering that no computer can calculate all the possible chess moves, the answer depends on how many moves the computer can calculate in advance within an acceptable time and the strategies with which it is equipped. In this context, it is often even impossible to prove which strategy is unequivocally the better one. An even more dramatically sharpened situation exists in the case of cognition problems. The content of a complex table will probably be interpreted in a hundred different ways by a hundred different people, and conventional computer programs can only provide a very primitive interpretation.

Another example of an incalculable problem is the number of the possibilities of combining pixels of an large digital image to form various objects. The number of possible combinations is so large that no computer can produce all the possible objects and examine their properties. Thus, except for trivially small digital images, no computer can find the uniquely "best" set of objects for an image. This inability to calculate the optimal solution applies particularly to cases where the meaning of number blocks (or image objects) can be defined only by way of the relationships with other number blocks (or image objects). In such cases, the number of combination possibilities explodes to an immeasurable scale. Thus, it is the complexity of the task that is responsible for the difference between a table calculation and a table interpretation.

Nature has developed a strategy for such incomputable situations—the evolution in small steps through primitive life forms to more complex life forms. The Cognition Language offers a language that, in a natural manner, allows evolution in small steps from primitive interpretation blocks within data structures to more sophisticated ones. In this procedure, individual process steps are applied to the interpretation blocks. Different interpretations (even if they are still primitive) require different process steps.

In this context, a primitive interpretation block can be a single number of a table if that number differs drastically from the other numbers. However, this number is a component of a larger unit, for example, a column. Thus, the entire column may be of special significance and therefore also require special processing. However, it may also be necessary that other columns, which are in a special relationship with the former column, also need to be subjected to special (possibly different) processing.

The concepts, labels, and domains of the Cognition Language allow local processing and the stepwise development from the simple to the more sophisticated. The separation of knowledge in the class network from the processes in the process hierarchy increases the orderly arrangement of the program and it simplifies the programming and its optimization, as well as the search for errors.

Tables and digital images have a similar structure. Both consist of an n-dimensional ordered field of numerical values. In images, besides pixels, the image objects play decisive roles. In tables there are, besides the numbers, above all rows and columns. Image objects are typically difficult to extract, while the rows and columns, on the other hand, are given. However, the rows and columns are far from being the only interesting objects in tables. A column or a row can contain unidentified sub-objects. For example, in the monthly sales of a company, there may be an abrupt change in the numerical values. This can have been triggered by an event, which may or may not appear explicitly in the table (for example, a marketing activity). In any case, there is a time before and a time after the event such that the column can be subdivided into two sub-objects, one with a higher average value and one with a lower average value. It may make perfect sense for the interpretation of a table to process these sub-objects, and to establish a relationship between them and other objects (the marketing activities). Taking into account the sales of the previous years may also make sense. Thus, the result is a multiple-scale segmentation problem that is similar to that encountered in image analysis, although in this example it has only one dimension.

For images, depending on the dimension of the image, n-dimensional neighborhoods play a large role. This is of little significance for tables, although tables may have some significance especially if the rows and columns can be sorted by different criteria. Sorting modifies the table and, in analogy to image analysis, can be considered a special pixel filter.

Then it may make sense to segment two-dimensional objects, for example, areas in which the profits, sales, marketing activities and other sectors are simultaneously at a high level. In practice, two- or three-dimensional table problems, similar to those encountered with images, however, occur without sorting. For example no sorting is required if a parameter of a measurement value increases or decreases in small increments in a row and another parameter also decreases or increases in relatively homogeneous increments in the columns. However, this will normally not be the case, and immediate neighborhood in tables will typically be of significance only in the one-dimensional case. Nevertheless, there are higher ranked objects whose entries can be distributed over the entire table. Therefore, it is important to be able automatically to interlink data objects if together they constitute a sense object after an automatic classification analysis.

This can be considered a possibility for multi-dimensional segmentation of objects. In this case, one could establish a link between the temporal segments with high marketing activity with the temporal segments with high sales and the temporal segments with high profits. This network could be transformed into a hierarchically higher object and linked in the world knowledge with the class "marketing success". This classification can occur automatically by having the class marketing success satisfy certain object descriptions (expressions). Expressions are based on object property computations (features) and they can consist of fuzzy descriptions or simple conditions, such as the ratio of marketing cost to profit increase in the case of an abrupt change of less than 0.01. A class can result from the logical linking of many expressions. The comparison of the expression logics with the concrete objects yields a classification probability that, in the mentioned example, describes the magnitude of the success. In this manner, all the marketing successes (for example, since the formation of the company) with a classification probability of more than 0.5 can be found by segmenting and subsequently classifying objects. The objects can in turn again be linked to each other and form an object on an even higher level. The individual marketing successes can be compared to each other and again set in a relationship with other higher objects to find additional correlations.

The advantages of using domains can also be explained in this example. The objects "marketing successes" were not present in the original data; they were generated for the first time by the Cognition Program. Now they can be used as domains. Domains lead the process steps to the correct places within the data network. In our example, the domain description would be as follows: "go to all the marketing successes (class description of the domains) with a classification probability of more than 0.7 (condition for great successes) in the period after Jan. 1, 2000 (2nd condition, date of foundation of company), and allow the process to be active." The process step can include the computation of a number, for example, the variance of the ratio of the marketing cost to company sales. Here it is assumed that it is possible to establish, in the program, formulas that are based on features and variables (formula editor). As a result, one obtains a measure of whether there is a linear link between the marketing cost and the company sales.

A process hierarchy that performs the above-mentioned process is as follows. A first process step has the domain: go to all the marketing successes (with the corresponding conditions). The first process step has no process activity. A second process step (a sub-process step) has the domain: go to the sub-object marketing cost. The second process step has the process activity (algorithm): write the value of the features "total marketing cost" into the global variable "marketing cost". A third process step has the domain: go to the sub-object sales; and the process activity: write the value of the feature "total sales" into the global variable "sales". A fourth process step has no domain specification and the following process activity: apply division to the global variables "marketing cost" and "sales" and write the result into the global variable "ratio". A fifth process step has the domain: go to the super-object (marketing success); and the process activity: write global variable "ratio" into the local variable "marketing cost/sales". The sixth process step, which is not a sub-process step of the first process step, has the domain: go to all the marketing successes as before. The sixth process step has the process activity: calculate the statistical value of the standard deviation of the local variable "marketing cost/sales" and write the result into a global or local variable with an appropriate name.

Returning to FIG. 19, which shows magnetic resonance images of a human head, two columns of six slices and two columns of an enlarged segmentation result of three images can be seen. The enlarged slices include the segmentation result and show the left and right ventricles and the white brain substance. In the column of six slices, the left ventricle sections can be linked to each other, and the total volume of the left ventricle can be determined. The linking can be visualized by clicking on a single section of the object with a computer mouse. Then, all the objects that are linked to the former object can also be labeled automatically at the same time. In this manner, one can verify whether the linking has worked as desired. A similar implementation can also be carried out for other data, such as texts or tables.

The Cognition Program also allows the calculation of table data. To perform a table calculation, a row segment is clicked, and those segments linked with this segment are also selected automatically. A hierarchically higher ranked object can then be visualized on the user interface. Geometrically higher ranked objects can be represented with color coding. For example, by clicking on a brown field, the entire brown field is labeled. The brown field is then available as an object for domain navigation. It is also possible to have the numbers be represented directly.

In the context of the process hierarchy, the question of operational flow control (run time environment) may also be important. In this regard, a number of alternatives or additions are provided. The Cognition Program allows iterative processing of heterogeneous mass data from heterogeneous data sources for extracting user-specific, relevant information such as parameters and diagrams). The processing assigns data to objects and generates, deletes and links objects and subsets of objects. The processing also restricts the application of processing instructions to certain dynamically generated object sets (domains). The objects and processing instructions can be represented graphically or textually, and they can be edited by the user.

Image-Based Biomarkers

In another embodiment, the Cognition Program (CNL) is used to generate biomarkers that predict a clinical endpoint of a patient. Data mining techniques are combined with image analysis to achieve context-driven image mining. Data mining steps are incorporated into the software tool that performs the image analysis. An image-based biomarker is a predetermined set of image analysis features weighted and combined in a predetermined manner to provide an indication of a clinical endpoint. Examples of clinical endpoints include a patient's overall survival time (OS), the disease free survival time (DFS), the probability that a treatment, therapy or drug will be successful or effective, the probability of getting a specific disease, the disease recurrence probability, the patient's disposition to having a heart attack or stroke, or the patient's life expectancy.

A computer language, such as Definiens' Cognition Program (CNL), is the foundation of the tool that processes images (image analysis) and additionally tables (data mining). For example, the software tool generates more accurate Kaplan-Meier curves of disease-free survival times (DFS). In a first processing round, data mining results are produced from the image analysis results. Certain items of the data mining results (e.g., a point in a scatter plot or a marker in a Kaplan-Meier curve) are classified as being outlier data that does not represent a good correlation between the data mining result and an observed clinical endpoint, such as the disease-free survival time (DFS). The Cognition Program automatically triggers new image analysis algorithms depending on the classification of the outlier items in the data mining result. Those new image analysis algorithms range from applying completely new segmentation and classification algorithms to simply modifying or extending the features that are exported into the table. In both cases, the table of output data is modified and thus results in a modified data mining output. The data mining output then leads to an automatic restructuring of the table in a way that different parts of the table are exposed to different data mining algorithms (or the same algorithms with different parameters). In this way, the software tool automatically optimizes data mining results.

Image analysis has one main goal: to end with a number, score or diagnosis. Achieving a segmentation of an image and a classification of the segments is a prerequisite for obtaining the number, score or diagnosis as opposed to the ultimate goal. There are two different use cases for image analysis.

Type 1.

In the first type of image analysis, an individual case is important. The analyzed images relate to a single individual (e.g., patient, mouse, specific cell culture, or specific zebra fish culture). The individual case is evaluated, perhaps also in combination with other data, resulting in a score or a diagnosis. The result can be information represented by a table. Those results can be incorporated into a decision support system, such as a clinical decision support system, a drug development support system, or a translational research support system. The goal of this first type of image analysis is to learn something about the individual case.

Type 2.

In the second type of image analysis, a collection of cases is important. The analyzed images relate to a large number of individuals. The individual results are less important than the collective content of the images. The results of the image analyses (individual scores or tables) are combined into one table called a meta-table. In most cases, additional data are also incorporated into this meta-table. The additional data can be a wide variety of data about the individuals (e.g. patients, mice, specific cell cultures, specific fish cultures) to which the images relate. For example, the meta data can include a patient's age and weight, family history, known diseases and intolerances, DNA profile, blood values, whether the patient smokes and whether the patient breast fed her babies.

For both types of image analysis, the additional step of data mining follows. The Cognition Program searches for patterns and correlations in the comprehensive data set (table of type 1 or 2). For additional details on searching for patterns and correlations relating to type 1 tables, see U.S. Patent Application Publication 2011/0268331 entitled "Image-Based Patient Profiles," which is incorporated herein by reference. There are different forms for visualizing patterns and correlations. The image analysis disclosed herein involves the alternation of classification and segmentation. A specific classification triggers a specific segmentation algorithm. This means that the classification of the analysis result is used as a hint for triggering a new analysis. In this manner, the quality of the analysis is optimized in an iterative manner. After the image analysis comes to an end, several features of image objects are exported into tables. Those features are generally of a statistical nature. After the application of data mining algorithms, data mining results are produced. Within those results, hints are again generated as to which new additional data mining algorithms should be applied, or which new structures of the table should be implemented, or which new image analysis algorithms should be applied (perhaps only to certain types of images), or which new image features should be exported into the table. A large number of image features are exported into the table, and the data mining procedure selects the relevant ones. There is, however, a computational problem as the possible combinations of new features quickly become too large to calculate. Whenever the number of permutations gets too large, it is advantageous to collect hints for limiting the permutations. Collecting the hints is called "context driven analysis," which heretofore has been applied only to image analysis and now is also being applied to data mining of the results of the image analysis, which we call "Image Mining." Thus, Image Mining is the unification of image analysis and data mining, and the software tool performs context-driven image mining.

The Cognition Program performs "context-driven image mining" by combining image analysis and data mining in a unified form such that the individual results of the data mining are classified, or parts of the data tables are classified and structured. Those classifications are then used to perform modified and additional image analysis, as well as modified and additional data mining with the results of the image analysis.

Figure 27:
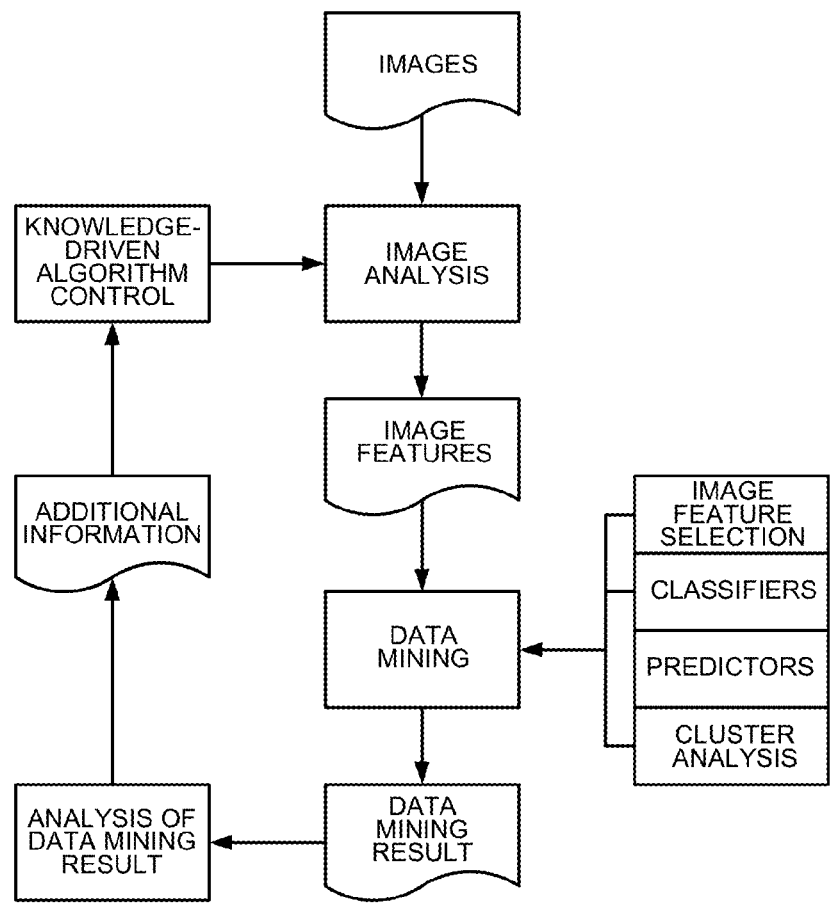
FIG. 27 is a diagram of a feedback loop that feeds image analysis results back into the image analysis steps to refine the image analysis.

FIG. 27 shows a feedback loop in which image analysis and the results of the analysis are fed back by knowledge-driven algorithms into the image analysis step to refine the image analysis. In each subsequent iteration of the loop, image analysis can extract additional image parameters and continue processing the image. Subsequent processing can look for new structures that were not analyzed during the first run. In subsequent steps, the analysis algorithms may be applied only to a portion of the image. Algorithms of the Cognition Program control the iteration loop and can use knowledge-driven and local adaptive processing based on hierarchical semantic networks. The control algorithms stop the iteration loop when predetermined conditions are met, such as a threshold being reached or after a certain number of iterations.

In one example of the iterative feedback-loop processing, object-based image analysis first generated high-level objects and low-level objects. For example, the low-level objects include nuclei, lumina, cell membranes and cytoplasm. The high-level objects include glands, necrotic areas, tumor regions and epithelia tissue. High-level objects are made up of low-level objects. For example, glomeruli are organelles made up of nuclei, lumina and other cellular structures. Each of the objects has a multitude of properties (so-called "image features") that can be measured and evaluated for data mining purposes.

A number of predefined image features are extracted from each of a plurality of medical images. Due to the multitude of image features associated with the multitude of image objects, the image features used for image-based data mining ("image mining") are limited upfront so that the available processing resources can perform the required calculations of the iterative feedback-loop processing. Nevertheless, the number of features used in the feedback-loop processing can be larger than if the calculations for the image mining were performed in a straight shot without the feedback loop.

Consider a simple exemplary image analysis performed in a linear flow compared to being performed with the novel iterative feedback-loop processing. Even a simple medical analysis results in a multitude of image features. For example, five high-level objects (tumor, stroma, necrotic areas, inflammations) are analyzed on five hundred images of tissue with tumor structures. For each high-level object, three lower-level objects (nuclei, lumina, other cell compartments) are analyzed, each having eight different subtypes. This simple case covers only a small number of the typical parameters that are considered by a pathologist investigating breast cancer tissue. And complex clinical studies can involve thousands of patients with several images per patients. In the simple case, four measurements are made per low-level object such as area, staining intensities of two stains and shape distribution parameter. Eight measurements are made per high-level object, and four additional measurements characterize subtypes of objects. Consequently, the simple case requires twelve basic image features, thirty-two image features for the objects and sixteen image features for the subtypes of objects. These sixty image features already pose a significant challenge to one-shot processing of the data mining algorithms. But if objects are eliminated from the model, then image parameters based on these neighboring objects will be zero and will lead to poor results.

The novel iterative feedback-loop processing method, however, starts with simple high-level image analysis that is significantly faster than a robust analysis performed all at once. In this way, first subset of image features are extracted from each image. The data mining algorithms then evaluate the image analysis results and group the images based on the results. In a second iterative processing step, the images are analyzed based on their image features. For example, those regions of the images are analyzed more intensively that have features indicating tumor cells or inflammation. If data mining of the results of the first iteration showed two types of results, then the images are separated for two groups of patients. Specialized image analysis algorithms are performed on each group of images and need not be performed on all of the images. Segmentation and classification tasks are split up into subprocesses that must process a smaller number of model parameters using a more consistent set of variables from a smaller portion of the images.

In one embodiment, an image-based biomarker is developed that correlates the data mining results of the image analysis to a clinical endpoint. The magnitude of the biomarker indicates how best to draw a conclusion from the image analysis results. The biomarker is based on feature vectors that describe regions of interest in medical images of a patient, as well as meta data properties. As indicated above, meta data properties comprise the patient's age, sex, family history, blood values, or genetic profile, and results from prior examinations. The feature vectors describe objects of data network 11 and can be defined as Euclidian vectors within cognition network 96. For this embodiment based on the analysis of medical images, the feature vectors are denoted as "image features." Thus, the image features describe various properties of classified objects in the medical images. Examples of image features include: average size of the nucleus of a cancer cell, the staining intensity of a membrane compared to the cytoplasm, the percentage of inflammation of a class of cells, the density of tumor cells and the number of epithelial cell layers.

Figure 28:
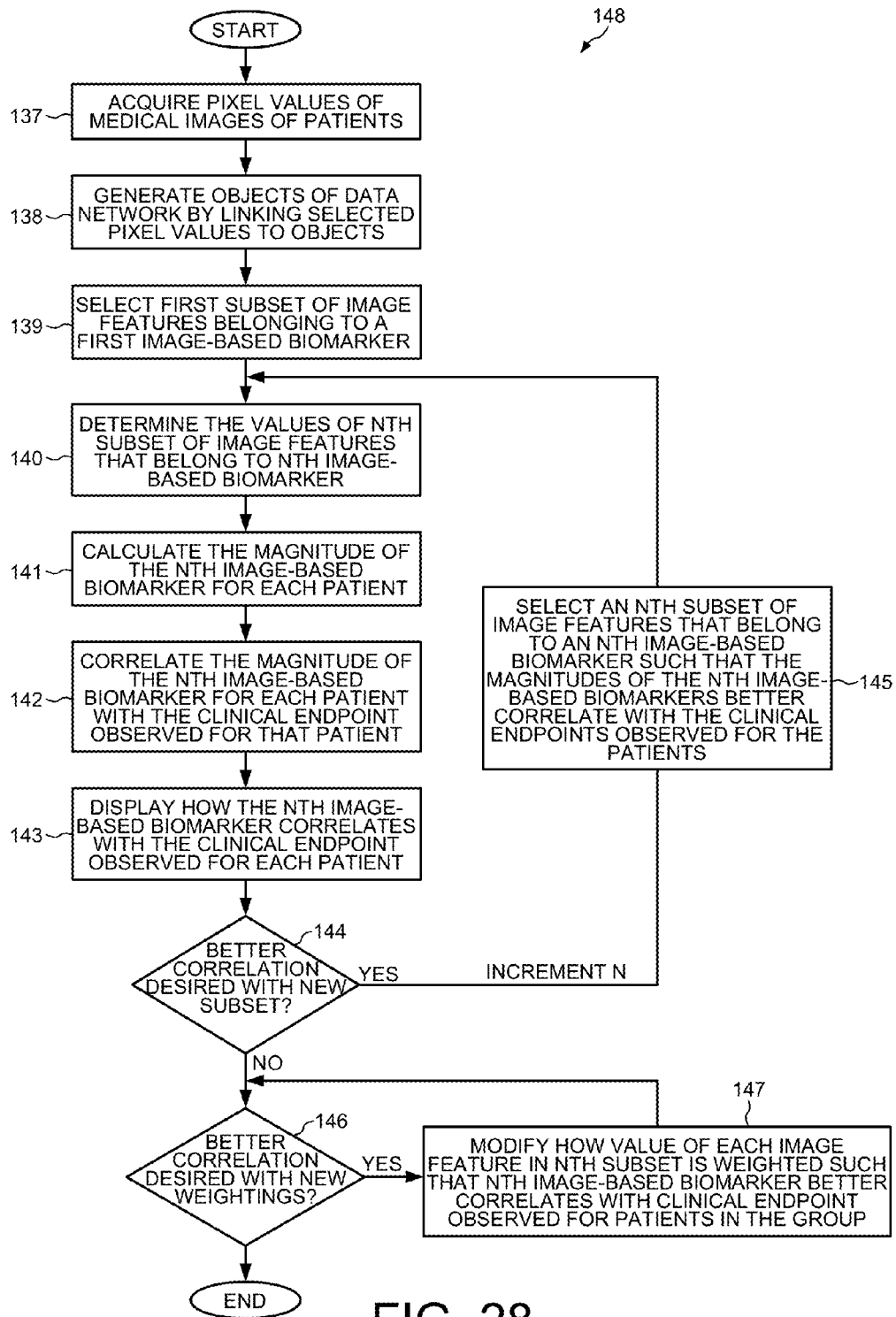
FIG. 28 is a flowchart of steps for analyzing medical images of patients to generate an image-based biomarker.

FIG. 28 is a flowchart illustrating steps 137-147 of a method 148 for analyzing medical images of patients to generate an image-based biomarker whose magnitude correlates to a clinical endpoint that was observed for the patients whose medical images were analyzed. The image-based biomarker can be used to predict the clinical endpoint of other patients whose clinical endpoints have not yet been observed. The steps of method 148 are described in relation to the images and screenshots depicted in FIGS. 28-34.

In a first step 137, pixel values are acquired from medical images of a group of patients. In one example, images were acquired from three hundred ninety biopsy tissue cores taken from one hundred thirty-two patients with esophagogastric cancer. The biopsy tissue was stained for the protein called human epidermal growth factor receptor 2 (HER2/neu) using antibody clones. The HER2 protein promotes the growth of cancer cells. Immunohistochemistry (IHC) was performed to determine HER2/neu protein expression. Method 148 is thus used to generate an image-based biomarker that correlates to the disease free survival time (DFS) and the overall survival time (OS) of patients with a high risk factor for acquiring HER2-positive esophagogastric cancer. In about one of every five cancers, the cancer cells make an excess of HER2 due to a gene mutation. HER2-positive cancer tends to be more aggressive than other types of cancer. However, treatments that specifically target HER2 are very effective, including trastuzumab (Herceptin) and lapatinib (Tykerb).

Figure 29:
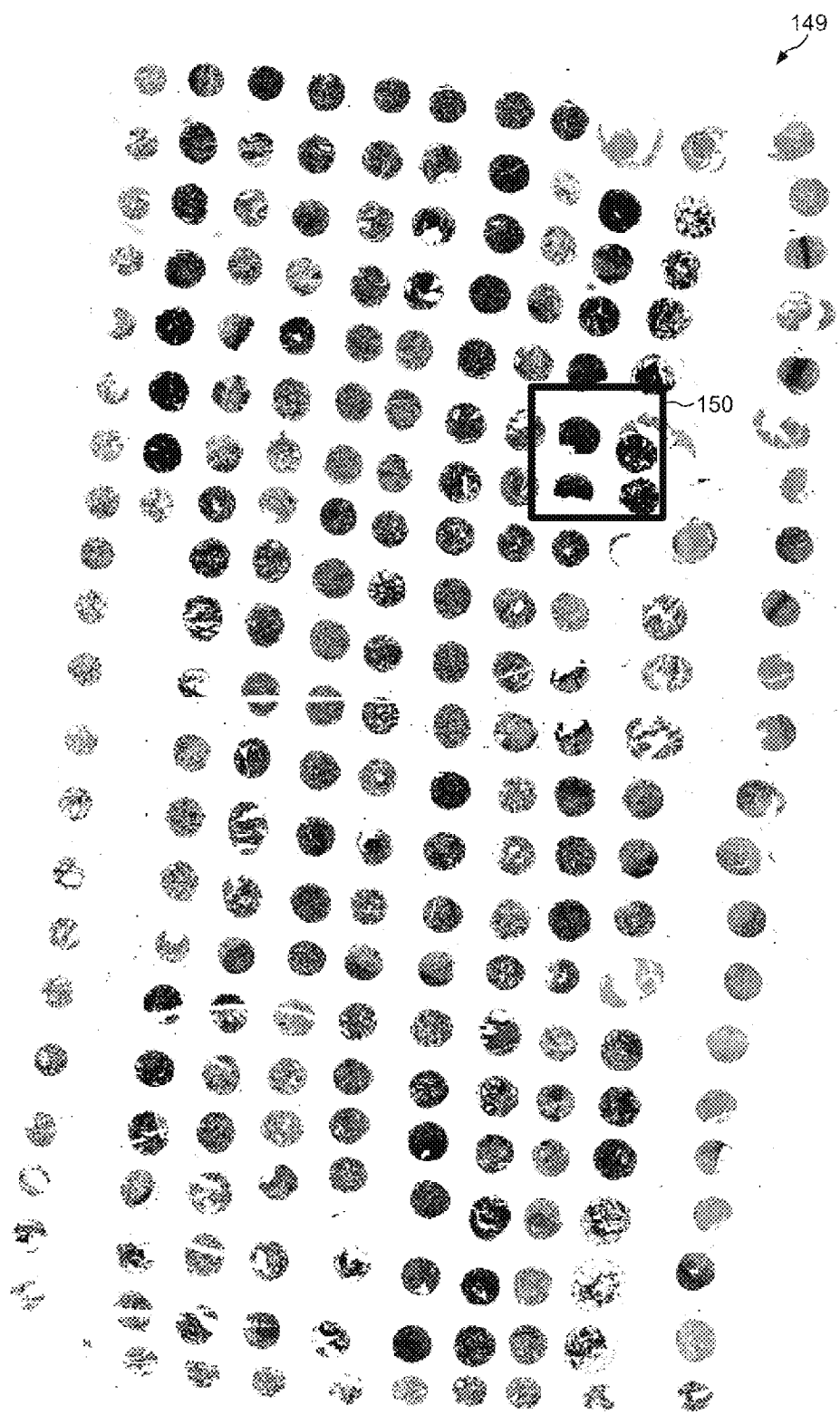
FIG. 29 shows a tissue micro array from which the medical images for the method of FIG. 28 are acquired.

FIG. 29 shows one of three tissue micro arrays on which the three hundred ninety biopsy tissue cores were placed. Tissue micro array 149 includes two hundred twenty-seven biopsy tissue cores taken from some of the one hundred thirty-two esophagogastric cancer patients. The tissue cores in box 150 are shown in more detail in FIG. 31. To compare the performance of method 148 with clinical endpoints estimated by a pathologist, a pathologist scored each biopsy tissue core as 0, 1+, 2+, or 3+. A score of 0 or 1+ is negative for the presence of the HER2 protein. A score of 2+ is weakly positive (using IHC), and 3+ is positive.

In step 138, objects of data network 11 are generated for each of the medical images by linking selected pixel values to selected objects according to class network 12 and process hierarchy 13. For example, objects are generated for all of the cells and cell parts in cancerous regions of interest in the tissue on the tissue micro arrays.

Figure 30:
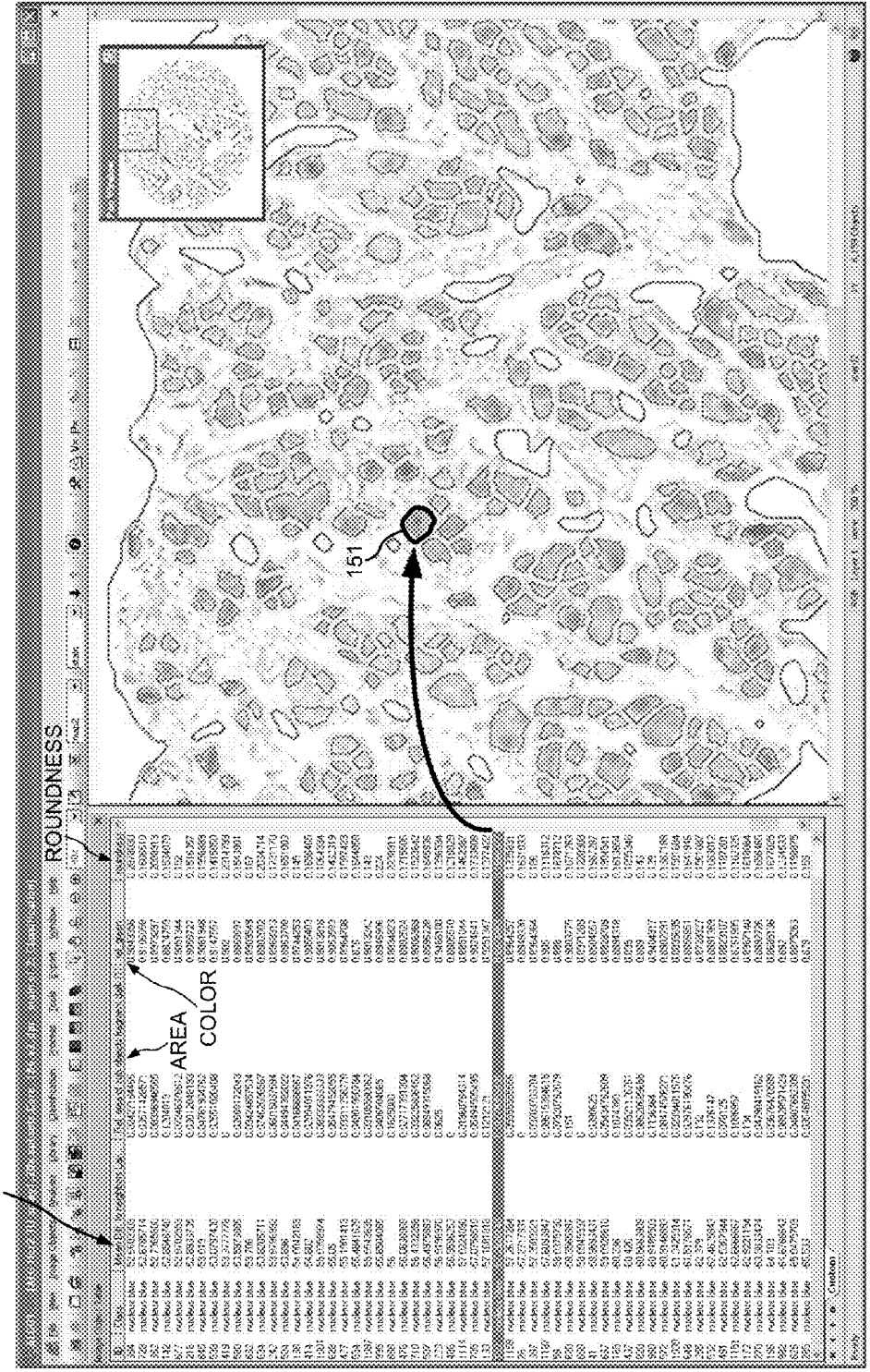
FIG. 30 is a screenshot showing objects generated from one part of the medical images of FIG. 29.

FIG. 30 is a screenshot generated by the Cognition Program showing the objects generated in just one part of the digital image of one biopsy tissue core. On the left is a table listing four of the many image features of the objects that are segmented in the digital image on the right side of the graphical user interface. The table lists the values of the four image features: (i) mean difference of area to that of neighbor nucleus, (ii) area of nucleus, (iii) color of nucleus, and (iv) roundness of nucleus. An object 151 is highlighted in the digital image on the right side of the screenshot. Object 151 represents a nucleus in the biopsy tissue. The values of the four image features for object 151 are highlighted in the list on the left side of the screenshot. The highlighted values of the four image features for object 151 are: −57.25, 0.01779, 0.897 and 0.1596.

Figure 31:
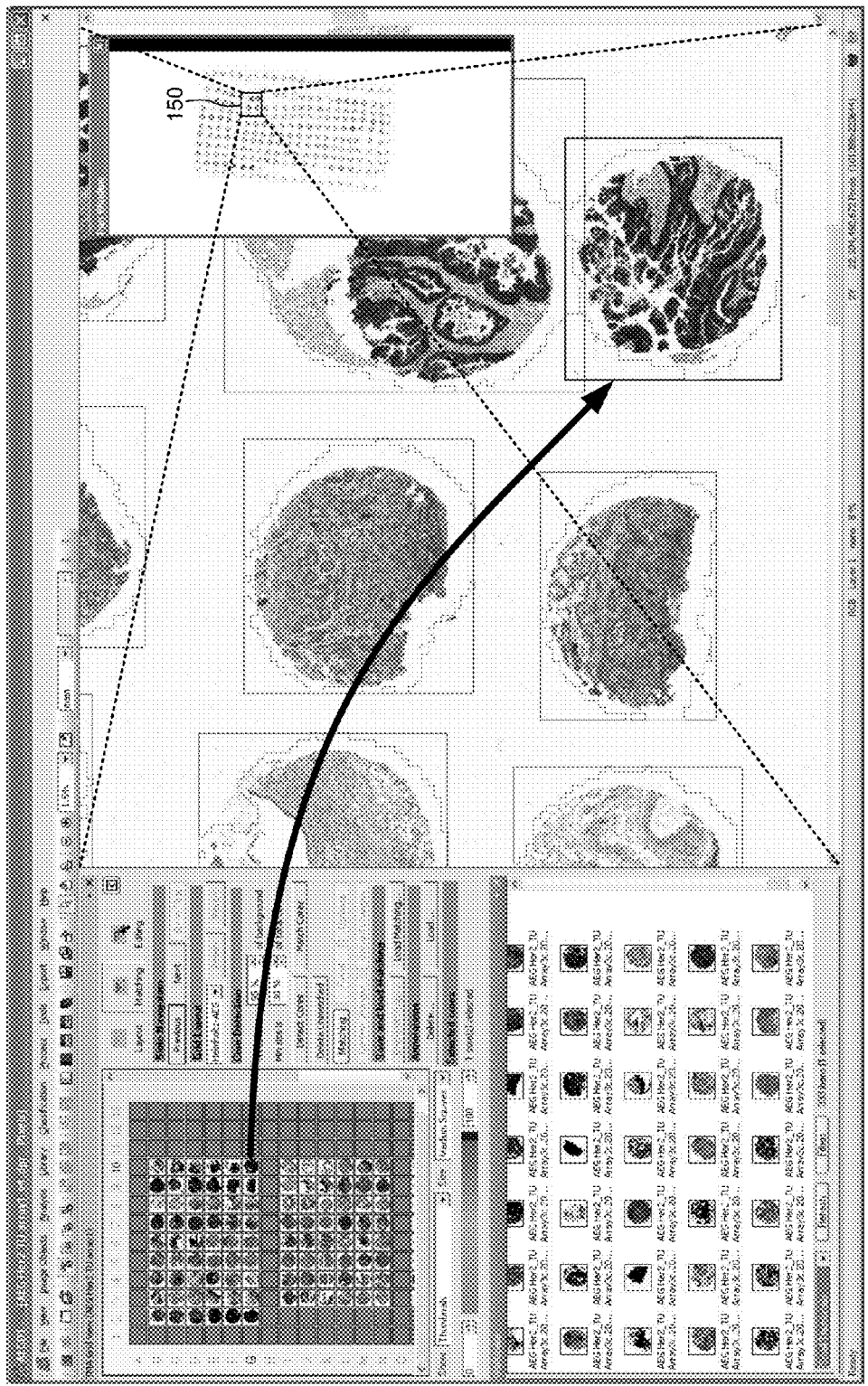
FIG. 31 is a screenshot of the graphical user interface of the Cognition Program showing a portion of the tissue micro array of FIG. 29.

FIG. 31 is another screenshot of the graphical user interface of the Cognition Program. The digital image on the right side of the screenshot is a more detailed view of box 150 shown in FIG. 29. Each of the biopsy tissue cores has been segmented as an object of data network 11. The substructures in each of the biopsy tissue cores have also been segmented and classified. The digital image of the lower right biopsy tissue core in box 150 has been placed in a matrix of tissue cores on the left side of the screenshot. The plurality of image features for the objects in each tissue core are then accessible by clicking on the appropriate tissue core in the matrix.

In step 139, a first subset of image features is then selected from the multitude of possible image features that can make up a first image-based biomarker. For example, the first image-based biomarker correlates the image features to the overall survival time (OS) of each patient.

In step 140, the values of the subset of image features that belong to the image-based biomarker are determined. Method 148 involves an iterative process of improving upon the correlation between an image-based biomarker and a clinical endpoint, such as the overall survival time. Thus, in the first iteration of step 140, the value of each of the first subset of image features of objects generated using object-oriented image analysis is determined, where the first subset of image features belongs to the first image-based biomarker.

Figure 32:
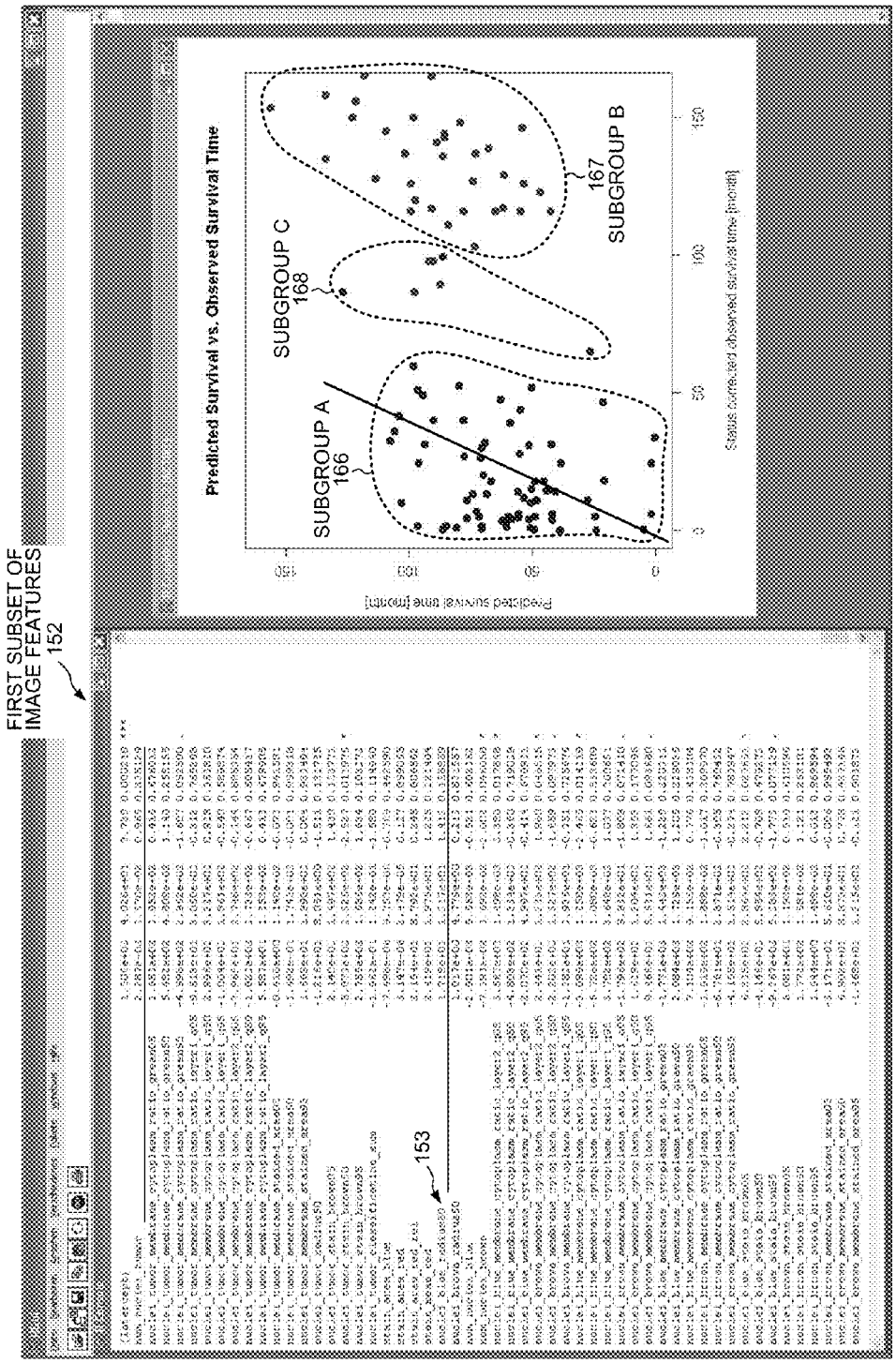
FIG. 32 is a screenshot with a list of image features that make up an image-based biomarker.

FIG. 32 is a spreadsheet generated by the Cognition Program that lists fifty-four image features in a first subset 152 of image features that make up the first image-based biomarker (CORE_METADATA.OS_TIME) that correlates the image features to the overall survival time (OS) of each patient. For example, the beginning image features in subset 152 include: (1) number of nuclei, (2) amount of membrane with a green stain intensity of 5% of the cytoplasm stain intensity, (3) amount of membrane with a green stain intensity of 50% of the cytoplasm stain intensity, (4) amount of membrane with a green stain intensity of 95% of the cytoplasm stain intensity, (5) amount of membrane with a stain intensity of 5% of the cytoplasm layer 1 stain intensity, (6) amount of membrane with a stain intensity of 50% of the cytoplasm layer 1 stain intensity, and (7) amount of membrane with a stain intensity of 95% of the cytoplasm layer 1 stain intensity. Subset 152 also includes the image feature 153 (nuclei_blue_radius50) which indicates the average length of the radius of the blue stained nuclei.

Figure 33:
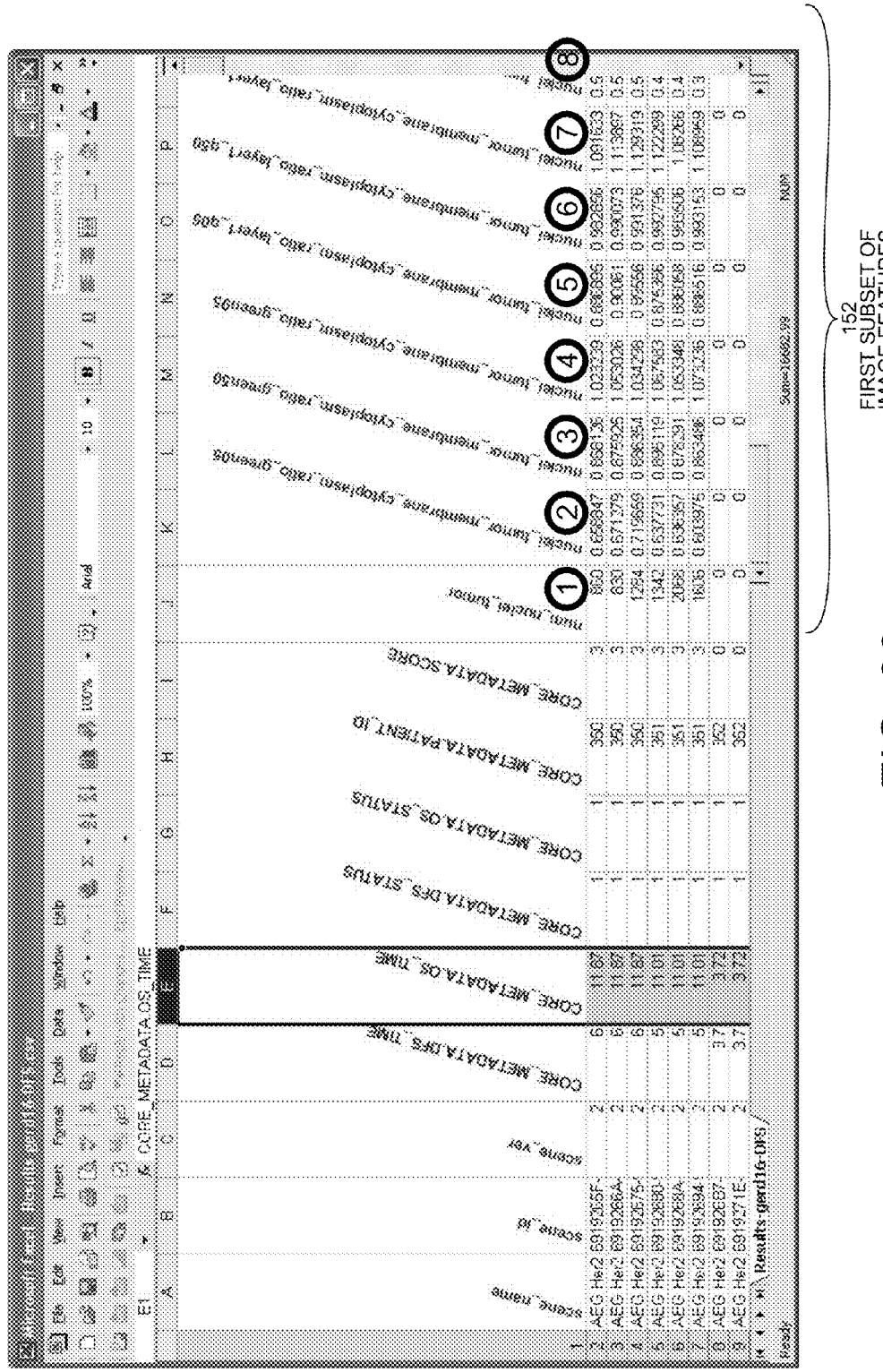
FIG. 33 is a screenshot with a list of the values of image features that make up the image-based biomarker.

FIG. 33 is a spreadsheet generated by the Cognition Program that lists the values of the image features for each of the identified objects, in this case the objects in the biopsy tissue cores in the matrix in FIG. 31. Each of the biopsy tissue cores is associated with the patient from which it was taken. The first image-based biomarker (CORE_METADATA.OS_TIME) is highlighted in FIG. 33. The spreadsheet lists the values of the first eight of the image features from first subset 152. The spreadsheet indicates that the first biopsy tissue core has 860 nuclei, the second tissue core has 830 nuclei, and the third tissue core has 1284 nuclei.

In step 141, the magnitude of the first image-based biomarker is calculated for each patient using the values of image features obtained from the biopsy tissue cores obtained from that patient. In a first embodiment, calculating the magnitude of the image-based biomarker involves weighting each value of each image feature in first subset 152 and then summing all of the weighted values. The spreadsheet of FIG. 32 shows how each of the fifty-four image features is weighted. For example, the image feature indicating the number of nuclei has a weighting of 0.335129, whereas the weighting of feature 153 (nuclei_blue_radius50) is 0.158859. The magnitude of the first biomarker is calculated by multiplying the value of each of the fifty-four image features times the corresponding weighting, and then summing the products. For the first image-based biomarker that correlates the image features to the overall survival time (OS) of each patient, the magnitude of the biomarker is converted into an associated number of months indicating the survival time.

Figure 34:
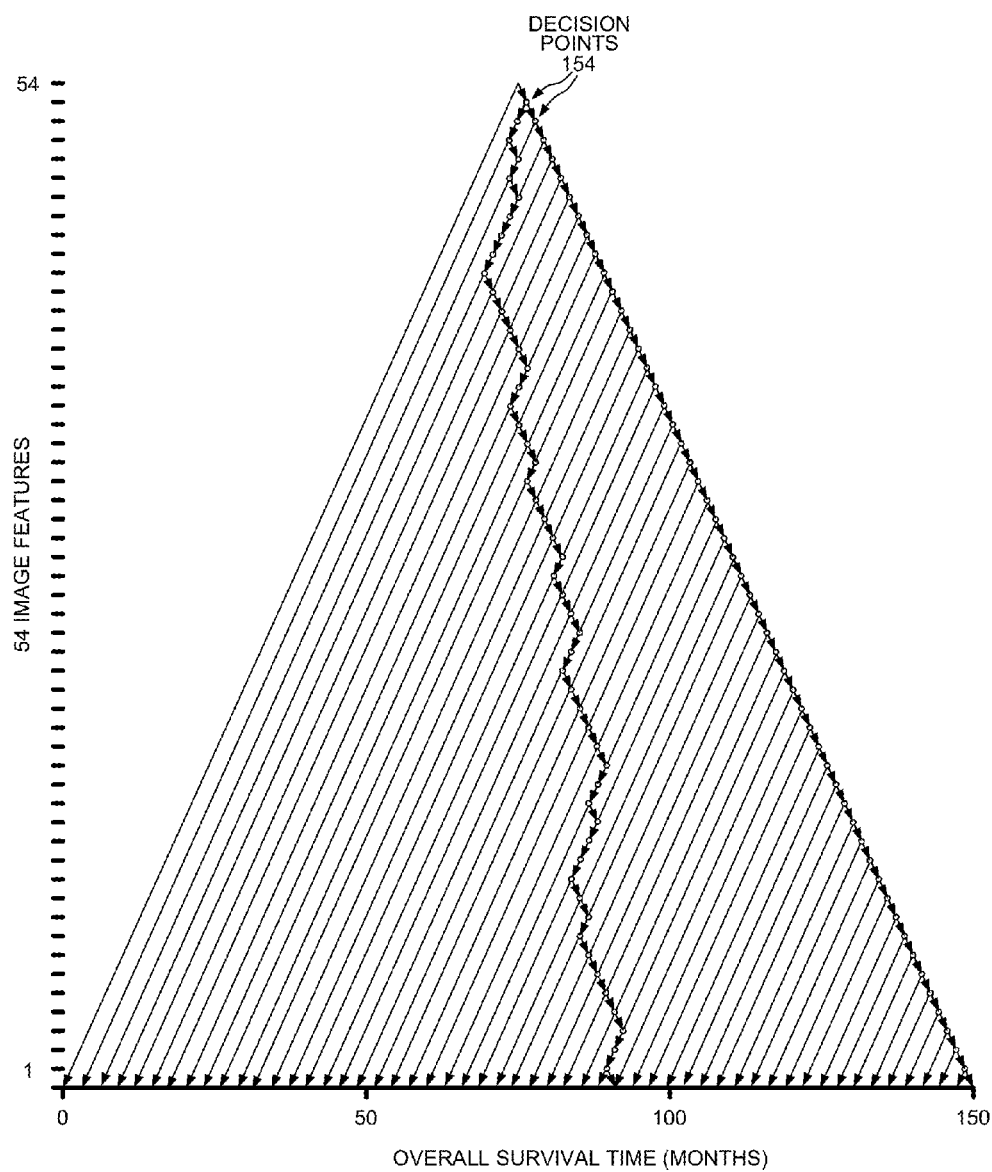
FIG. 34 is a diagram of a decision tree used to determine the magnitude of the image-based biomarker.

FIG. 34 illustrates a second embodiment of how the magnitude of the image-based biomarker is determined. The magnitude of the image-based biomarker is determined by performing a decision tree analysis with each feature in first subset 152 to generate a predicted clinical endpoint for each patient. In the second embodiment, a decision is made based on the value of each image feature as to whether the patient is likely to have a longer life or a shorter life. At each decision point 154 of the decision tree, the analysis takes the path of a longer or shorter overall survival time depending on whether the value of the image feature exceeds a predetermined threshold value. To simplify the illustration of FIG. 34, only the decision points 154 on the outer path of a longer life as well as along one exemplary inner path are shown. In the exemplary decision tree of FIG. 34, the amount of a longer or shorter overall survival time added at the decision point for each image feature is the same. However, weightings similar to those listed in FIG. 32 can be applied to each image feature by adding weighted increments of survival time at each decision point.

In step 142, the magnitude of the first image-based biomarker for each patient is correlated to the clinical endpoint observed for that patient. For the first image-based biomarker (CORE_METADATA.OS_TIME) that predicts overall survival times (OS), the number of months of overall survival time predicted for each patient is correlated to the actual time in months that each patient was observed to survive.

In step 143, how the first image-based biomarker correlates with the clinical endpoint observed for each of the patients in the group of one hundred thirty-two esophagogastric cancer patients is displayed on a graphical user interface generated by the Cognition Program.

Figure 35:
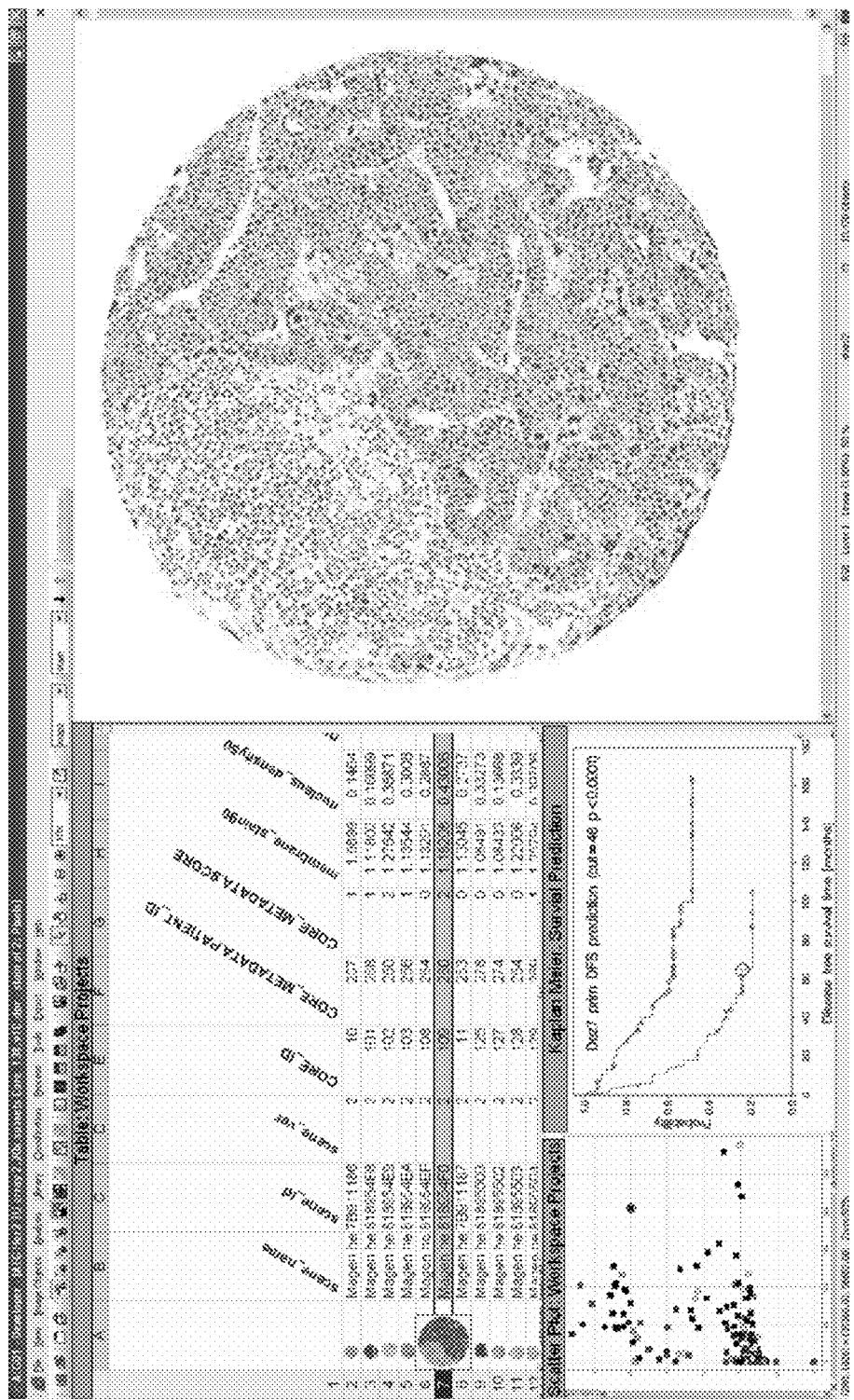
FIG. 35 is a screenshot of the graphical user interface that includes a scatter plot, a list of image features, a Kaplan-Meier graph, and an image of a tissue cores from the tissue micro array of FIG. 29.

FIG. 35 is a screenshot of the graphical user interface generated by the Cognition Program that includes a scatter plot in the lower left corner. The x axis represents the observed survival time, and the y axis represents the survival time predicted by the image-based biomarker. The screenshot of FIG. 35 also includes a list in the upper left showing the values of the image features similar to the list of FIG. 33. The screenshot also includes an image on the right side showing one of the biopsy tissue cores from the tissue micro array 149 of FIG. 29. FIG. 33 also includes a Kaplan-Meier curve showing survival times of the two groups of points in the scatter plot to the left.

A scatter plot of survival times is also included on the right side of FIG. 32. The scatter plot of FIG. 32 correlates the overall survival times predicted by the first image-based biomarker to the overall survival times observed for each of the patients in the group of one hundred thirty-two esophagogastric cancer patients. The correlation of the magnitude of the biomarker to the observed survival times is better the closer the points are grouped around a line that emanates from the intersection of the x and y axes.

In a decision step 144, the user of the Cognition Program decides whether a better correlation is desired between the survival times predicted using the first biomarker and the observed survival times. Considering that all of the point in the scatter plot of FIG. 32 are not located close to any line that emanates from the intersection of the x and y axes, the user determines that a better correlation can be achieved with a new biomarker made up of a different subset of image features. Method 148 of FIG. 28 is now used to improve the correlation between the observed clinical endpoints and a second image-based biomarker.

In a step 145, a second subset of image features is selected that belong to the second image-based biomarker such that the magnitude of the second biomarker for each of the patients better correlates with the clinical endpoint observed for each patient. The second subset can be selected by adding new image features to first subset 152 and/or by deleting other image features. Image features can be added that relate to the relationships between objects as opposed to simply the properties of the objects themselves. For example, the second subset can include the radius of each nucleus as well as the distance to the nearest neighboring nucleus. Steps 140-143 are then repeated for the second image-based biomarker using the second subset of image features. New biomarkers are generated using new subsets of image features until the user decides not to attempt to achieve a better correlation with a different subset of image features.

In a decision step 146, the user of the Cognition Program decides whether a better correlation between predicted and observed survival times can be achieved by calculating the magnitude of the nth biomarker using different weightings of the values of the nth subset of image features.

In a step 147, the manner in which the value of each of the image features in the nth subset is weighted is modified such that the magnitude of the nth biomarker better correlates with the observed clinical endpoints for the patients in the group. The weightings of the image features used to calculate the magnitude of the biomarker are modified until the user decides that a better correlation is not required.

Figure 36:
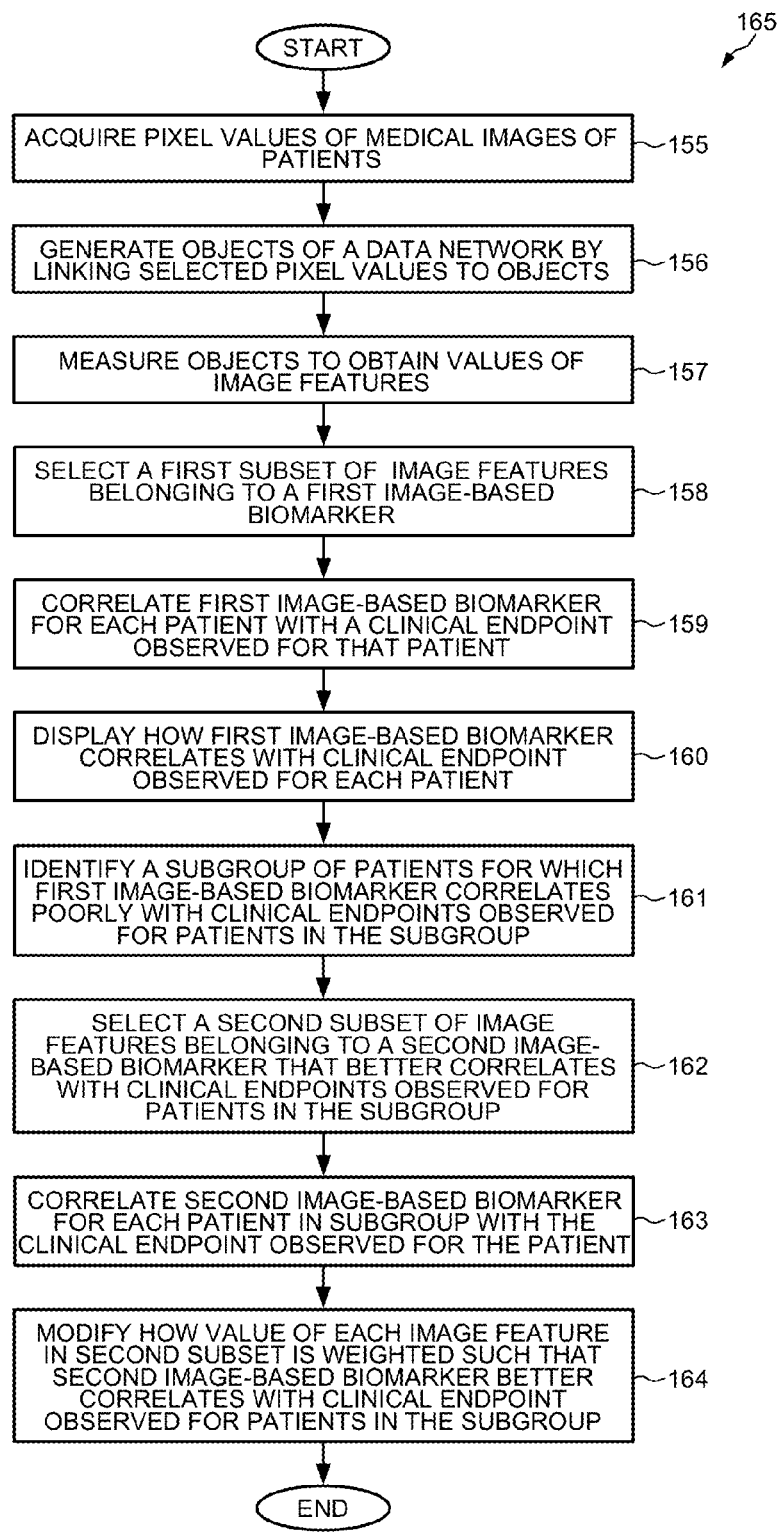
FIG. 36 is a flowchart of steps for analyzing medical images to generate separate image-based biomarkers for two groups of patients whose observed clinical endpoints correlate differently with the biomarkers.

FIG. 36 is a flowchart illustrating steps 155-164 of a method 165 of analyzing medical images of patients to generate separate image-based biomarkers for two groups of patients whose observed clinical endpoints correlate differently with a single biomarker generated using the same set of image features. Method 165 is used to segregate the patients into subgroups that each show a better correlation with a different biomarker generated using different image features.

In a first step 155, pixel values are acquired from medical images of a group of patients. Regions of interest in the digital images are analyzed. For example, the tumor cells in immunohistochemistry (IHC) stained digital pathology slides are identified, segmented and analyzed for HER2 protein expression.

In a step 156, objects of data network 11 are generated for each of the medical images by linking selected pixel values of the images to selected objects according to class network 12 and process hierarchy 13.

In a step 157, the objects are measured to obtain a value for each of a plurality of image features. For example, the image features include the number of tumor cells, the average staining intensity, the average radius of tumor cells, and the substructure of tumor nuclei image objects. Image features also include the relationship between other image features, for example the standard deviation of the area of the nuclei of the tumor cells.

In a step 158, the image features of a first subset are selected that belong to a first image-based biomarker. For example, fifty-four image features are chosen from among the multitude of possible image features that can be obtained by measuring and analyzing the objects in the medical images. The magnitude of the first image-based biomarker is calculated by summing the weighted values of the image features in the first subset.

In a step 159, the magnitude of the first image-based biomarker for each patient is correlated with the clinical endpoint observed for that patient. In this example, the first image-based biomarker is correlated to the overall survival time (OS) and to the disease free survival time (DFS).

In a step 160, the Cognition Program displays how the first image-based biomarker correlates with the observed clinical endpoint. In this example, the correlation is displayed in a scatter plot that plots the predicted overall survival time of each patient based on the value of the first biomarker compared to the observed survival time. An example of such a scatter plot is the graph at the right of FIG. 32. The correlation between the biomarker and the observed survival time is better the closer the points are grouped around a line that emanates from the intersection of the x and y axes. The scatter plot of FIG. 32 shows that not all points are grouped around any single line.

In a step 161, a subgroup of patients is identified for which the first image-based biomarker correlates poorly with the clinical endpoint observed for the patients in the subgroup. The scatter plot at the right of FIG. 32 shows three groupings of points. A subgroup A (166) of points to the left of the graph indicates a good correlation between the observed survival time and the survival time predicted by the first biomarker. A subgroup B (167) to the right of the graph represents patients who recovered from the disease and did not die of the disease. The first image-based biomarker correlates poorly with the observed survival times of the patients in subgroup B because the patients recovered from the esophagogastric cancer.

The first image-based biomarker also correlates poorly with the observed survival times of the patients in subgroup C (168). Each of the patients in subgroup C (168) represents an outlier for which the fifty-four image features of the first image-based biomarker do not provide a good indication of the overall survival time. For example, each of the patients in subgroup C is an outlier because the point plotting the magnitude of the first biomarker versus the observed survival time lies far away from the linear regression line through the center of the points of subgroup A.

In a step 162, a second subset of image features is selected that belong to a second image-based biomarker that better correlates with the clinical endpoints observed for the patients in subgroup C (168). Additional image features can be added to the second biomarker, or some image features can be removed. For example, if the first biomarker used the average staining intensity of tumor cells, the second biomarker uses the relative staining intensity of the membrane compared to the cytoplasm of the tumor cells. Thus, a different subset of image features is used for the patients in subgroup A (166) than is used for patients in subgroup C (168). The magnitude of the second biomarker is then determined for each patient in subgroup C using the image features in the second subset.

In a step 163, the magnitude of the second image-based biomarker for each patient in subgroup C is correlated with the clinical endpoint observed for each patient. The correlation is then displayed in a new scatter plot for just the patients in subgroup C.

In a step 164, the manner in which the value of each of the image features in the second subset is weighted is modified such that the magnitude of the second image-based biomarker better correlates with the observed clinical endpoints for the patients in subgroup C (168). Once the user of the Cognition Program is satisfied with the correlation between the image-based biomarker and the observed clinical endpoint observed for the patients in subgroup C, the image features and weightings that make up the second biomarker are saved to the file system.

The second image-based biomarker is then used to predict the clinical endpoint in new patients whose clinical endpoints have not yet been observed and for whom the first image-based biomarker results in a magnitude that falls outside a predefined base range.

Figure 37:
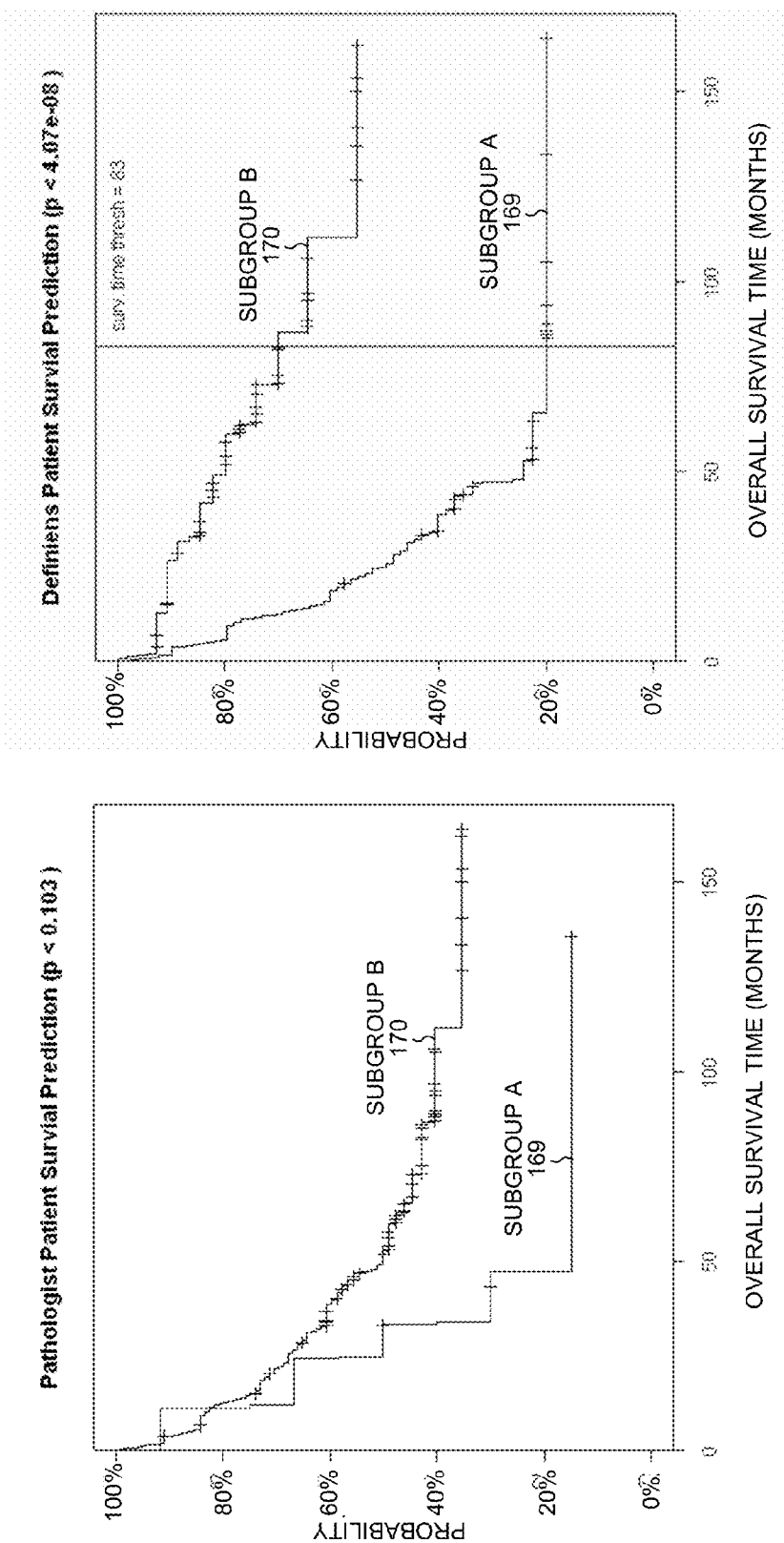
FIG. 37 is a Kaplan-Meier graph that shows overall survival times (OS) for two groups of patients.

FIG. 37 shows two Kaplan-Meier graphs that illustrate the ability of the Cognition Program to distinguish between patients that belong to a main group of patients and an outlier subgroup of patients for which a first image-based biomarker does not provide a good correlation with observed clinical endpoints. As shown in FIG. 35, the Cognition Program generates such Kaplan-Meier graphs. A Kaplan-Meier curve descends step-like over time and plots the percentage of the observed population still alive after a given period. For example, the lower curve of the Kaplan-Meier graph on the left side of FIG. 37 indicates that after about twenty-five months about fifty percent of the patients in a subgroup A (169) still survive. The upper curve indicates that after about one hundred months about forty percent of the patients in a subgroup B (170) still survive.

Two Kaplan-Meier curves can be compared to determine whether they differ statistically using a log-rank test or Wilcoxon's test. The "p value" indicates the probability of finding a difference between the two curves more extreme than the one observed even if the survival distributions of the two curves do not differ. If a predictor, such as an image feature used to generate a biomarker, results in a p value (comparing the results using the image feature and not using the image feature) of greater than 0.25, it is highly unlikely that the image feature will contribute anything to a biomarker that includes other image features.

In both Kaplan-Meier graphs of FIG. 37, the patients in subgroup A (169) along the lower curve correspond to patients in subgroup A (166) of FIG. 32 whose reduced overall survival time (OS) due to esophagogastric cancer correlates well with a baseline image-based biomarker. The patients in subgroup B (170) along the upper curve correspond to patients in subgroup B (167) of FIG. 32 who recovered at least partially from esophagogastric cancer and may have died from other causes.

The Kaplan-Meier graphs of FIG. 37 show that the Cognition Program provided a better segmentation into two subgroups of patients exhibiting different survival characteristics. The p value separating the curves of subgroups A and B was $4.07 \times 10^{-8}$ when the patients in subgroup A (169) were identified using method 165 and the survival times were predicted using a second image-based biomarker. The p value separating the curves of subgroups A and B, on the other hand, was 0.103 when the patients in subgroups A and B were identified by a pathologist scoring biopsy tissue cores obtained from the patients. The patients in subgroup B (170) in the graph on the left were those patients whose tissue cores were scored by the pathologist as 0, 1+ or 2+. The patients in subgroup A (169) in the graph on the left were those patients whose tissue cores were scored by the pathologist as 3+, a positive score for the presence of the HER2 protein. By segmenting patients into groups for which a particular set of image features better correlated to the observed survival times of test subgroups of patients, the Cognition Program can better predict the survival time of individual patients for which the survival time is not yet known.

Figure 38:
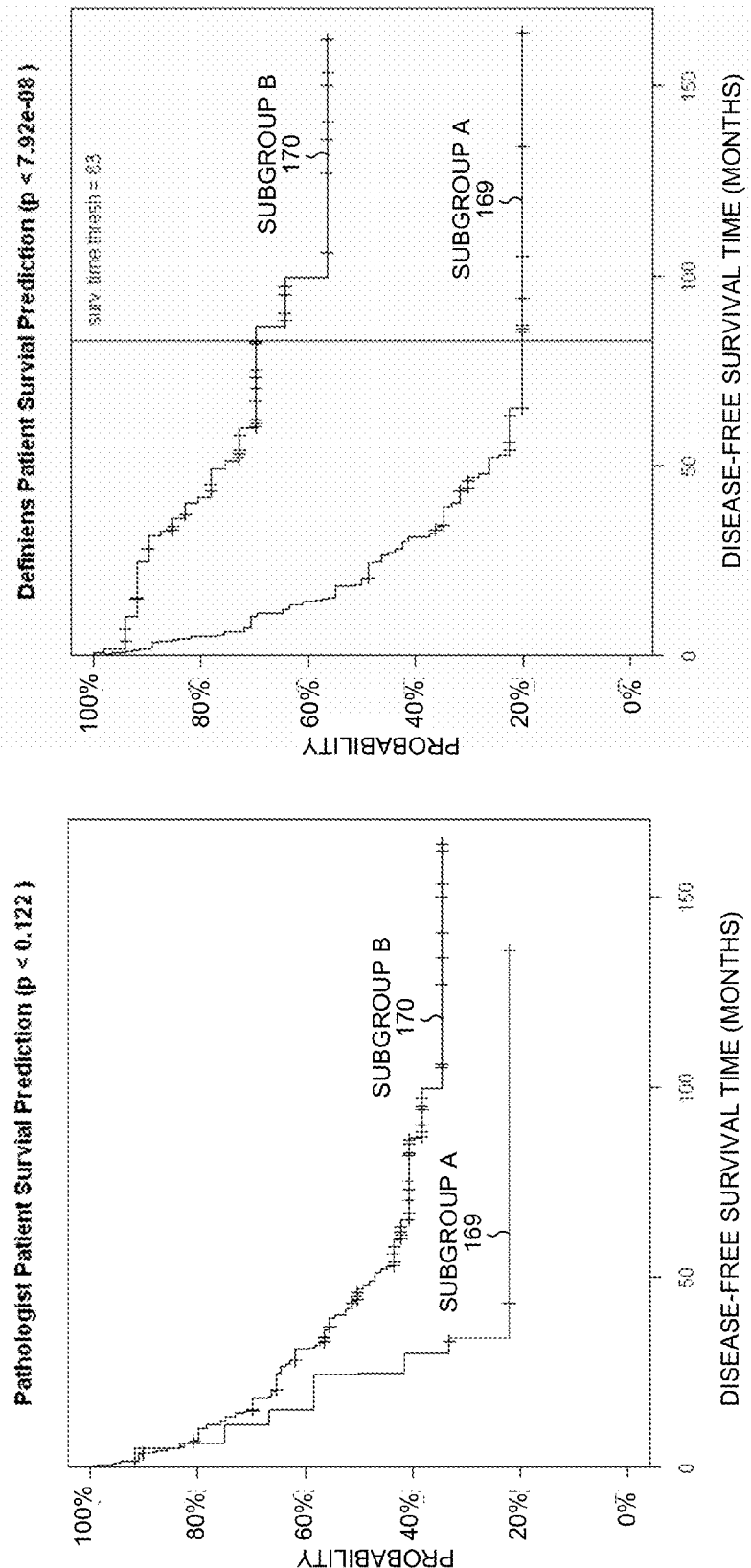
FIG. 38 is a Kaplan-Meier graph that shows disease-free survival times (DFS) for the two groups of patients.

FIG. 38 shows two Kaplan-Meier graphs that are similar to the graphs of FIG. 37 except that the curves represent the disease-free survival time (DFS) instead of the overall survival time (OS). The p value for the survival predictions of the two subgroups using method 165 performed by the Cognition Program is much smaller than the p value obtained by a pathologist scoring the tissue cores.

In yet another embodiment, an image-based biomarker is developed especially for medical images acquired by a specific imaging device, such as a computed tomography (CT) device, a magnetic resonance imaging (MRI) device, or a positron emission tomography (PET) device. For example, a physician identifies malignant cells in the breasts of test patients by using microscopy to analyze biopsy tissue cores. PET scans are then taken of the test patients, and the locations in the patients' breasts from where the biopsies were taken are determined. Then a PET-specific image-based biomarker is developed that marks the objects in the vicinity of where the biopsy tissue cores were taken. Using method 148, a subset of image features and the weightings of those features are modified to arrive at the PET-specific image-based biomarker whose magnitude is large for the malignant cells around the biopsy locations but small for other objects in the PET scans. The PET-specific image-based biomarker can then be used for new patients to identify malignant cells in PET scans of their breasts. A new patient need not experience the discomfort of a biopsy in order to determine whether a suspicious mass in her breast is malignant. Using method 148, the experience of physicians at interpreting medical images acquired using one type of imaging device can be used to identify objects in medical images acquired using another type of imaging device.

In yet another embodiment, a custom biomarker is developed for a specific object in a region of interest in a medical image. For example, a physician identifies a "suspicious mass" in a medical image of a breast (a mammogram) of a particular patient. The Cognition Program is then used to generate a custom image-based biomarker that specifically marks the suspicious mass. Using method 148, a subset of image features and the weightings of those features are modified to arrive at the custom image-based biomarker whose magnitude is large for the suspicious mass but small for other objects in the region of interest. Then a database of medical images is searched to find objects in mammograms of other patients that are also marked by the custom image-based biomarker. The physician then checks the medical records to determine whether the objects marked by the custom image-based biomarker were known to be malignant.

One such custom biomarker for detecting suspicious mass lesions in mammograms was developed based on 1024 images acquired from three hundred three different patients. Five different segmentation routines were performed on the images after a preprocessing step involving scaling the image size and conforming pixel gray values from different manufacturers' conventions. Because this segmentation produces a large number of objects, a pre-classification is applied that excludes non-plausible mass lesion objects by means of size, contrast and position criteria. A training database includes the image features of the remaining objects together with related patient meta-data (e.g., age). The training database also includes mammograms annotated by physicians that are used to test the performance of the custom biomarker.

Correlations between the annotated suspicious objects and the image features of the segmented objects are used to develop the custom biomarker for suspicious mass lesions. The goal is to define a custom biomarker that selects from all segmented objects more than 80% of the objects whose size and position are very similar to those of the annotated objects. Thus, the custom biomarker should achieve a hit rate of greater than 80%. The second goal is to minimize the number of objects marked by the biomarker that do not correspond to an annotation. Thus, a hit rate of more than 80% should be achieved at the same time that the number of false positives is minimized.

This goal is achieved in two ways. First, only those image features are selected that are best suitable for the custom biomarker. Second, the image features are combined in a mathematical logical expression in order to mark objects as being suspicious or not suspicious. Alternatively, the magnitude of the biomarker can be obtained using a decision tree approach for each image feature.

The initial custom biomarker is tested and provides performance measures, such as absolute and relative numbers of true positive objects (hits) and false positive objects, as well as the number of remaining suspicious mass lesion objects (misses) that are not yet found by the current development state of the custom biomarker. The initial output is investigated in a systematic manner. Image features that result in hits, false positives and misses are presented in a list and sorted by classification result. An interactive visual inspection of the list and the corresponding image objects helps the user, i.e., the person developing the custom biomarker, to identify new features and image segmentation procedures not yet used in the present state of the biomarker.

The visual inspection focuses on a subset of objects. If the number of false positives is much higher than the number of misses, then the visual inspection of the misses represents a less time consuming task. In that case, the reason for not detecting the suspicious masses might become obvious after a visual inspection of the misses. Compared to the hits that are already found, the appearance of the missed objects might be so much different that a new separate class description might be required. In this manner, a complex problem is divided into two or more less complex problems. So the extension of the class description of a suspicious mass is represented by several subclass descriptions. Through visual inspection of the misses, it becomes clear whether a new type of suspicious mass needs to be introduced. If this is the case, an additional biomarker for this new type of suspicious lesion is defined by taking the special features of this new object type into account. The revised custom biomarker is then tested, and the number of false positives is treated statistically with only minor visual inspection. The goal is to turn misses into hits without increasing the number of false positives.

A new subclass description can be created after a quick and sorted visual inspection of a small subgroup (in this case the misses). Thus, the software tool for optimizing the custom biomarker supports the visual inspection of subgroups of objects. Subgroups are defined within the list of objects and their image features. The software tool displays the corresponding objects as sections of the images containing the objects. The tool also displays the segmentation results. The segmentation results enable the user to judge whether the segmentation failed completely or was not precise enough. Depending on such a conclusion, either an additional segmentation can be introduced, or an existing segmentation procedure can be improved. In this way, the quality of the image features used by the custom biomarker is improved. New or modified segmentations allows for both improved as well as for new image features. This step-wise procedure involving visual inspection successively enhances the quality of the custom biomarker. Without visual inspection of the subgroups of objects, however, the process might not lead to a positive result.

Another way to enhance the quality of the custom biomarker is to recognize that a certain range of the values of an image feature result in false positives. This range of values can be excluded from contributing to the biomarker magnitude. The quality of the biomarker can also be enhanced by recognizing a correlation between certain hits and other available data in the database that can exclude false positives. For example, in the classification of one type of suspicious mass lesion, using the patient's age as a feature excludes some false positives. Using such meta data as features improves the custom biomarker by increasing the number of hits and decreasing the number of false positives.

The first implementation of a customer biomarker typically delivers many hits for a certain type of suspicious mass lesion but also too many false positives. Then using visual feedback and statistical investigation, image features for two types of suspicious mass lesion objects are developed. Additional biomarkers are developed using the visual feedback and statistical refinement for each different type of suspicious mass lesion in the training database.

When existing image features are not powerful enough adequately to differentiate visually recognized types of different suspicious mass lesions, new image features can be created, derived or improved upon. New image features can be calculated by combining existing features and metadata. For example, an image feature that measures breast density can be multiplied by the patient's age. New image features can also be derived from objects obtained by modifying or improving upon the initial segmentation used in the image analysis.

The custom biomarker for detecting suspicious mass lesions in mammograms is called the "Definiens Mammo" biomarker. The Definiens Mammo biomarker detects suspicious mass lesion objects for ten subclasses of lesion types. The Definiens Mammo biomarker was used to mark the mammograms from two hundred patients that were not present in the training database.

Many of the steps for defining image features and new types of segmentation are independent of the type of images being analyzed. Those standard step routines are included in the Cognition Program. This is helpful because many of those routines might take weeks to accomplish with visual inspection, whereas it takes only minutes for the Cognition Program to perform the routines on the images. The Cognition Program automates the cycle from image analysis results, to data mining, back to image analysis, to data mining and back to image analysis, etc. In the case of the suspicious lesions described above, the misses are detected by the Cognition Program in the first step. The misses are defined by the manually annotated objects for which no corresponding suspicious lesions were selected by the first iteration of the custom biomarker. The outlier objects are also detected. The desired result of the outlier detection must be defined by the user beforehand. For example, the user could require the best possible prediction of a clinical outcome derived from the image features. Or the user could require the best possible prediction of which drug is best suited to cure a specific disease detected by the image features in medical images. The outliers are defined as those results derived from the images that deviate most from the desired results, e.g., have the worst predictions compared to the actual clinical outcome. In other words, outliers are represented by those objects for which the results are worst compared to the desired results.

The software tool searches for additional image features by focusing on the outliers. As only a small subset of data needs to be investigated in more detail, many options can be tested. For instance, a large number of algorithmic combinations of existing image features are defined as new image features and their values are calculated for the outliers. Several different statistical investigations, such as cluster analysis, are then applied to the image features that mark the outliers. If clusters can indeed be found, a few non-outliers are picked randomly, and their new features are compared against those of the outliers. If the outliers and the non-outliers are marked differently by the new combined image features, the new image features are combined into a new version of the custom biomarker and tested with all of the existing data.

A similar procedure is applied to the modification of the segmentation procedures. A list of alternative segmentations and a list of segmentation extensions is tested on the outlier objects. The segmentation extensions and the alternative segmentations both lead to modified values of the old image features. The procedure for then selecting the correct new image features is similar to the procedure for selecting the correct combined new image features as described above. The difference is that the segmentations are usually much more time consuming than are the classifications.

The selection of new image features can also be knowledge driven. Normal ranges of the values of the image features are defined by the user beforehand. After a new segmentation is performed on outlier objects, the values of a large list of image features are compared to their predefined normal ranges. For example, the comparison can indicate a contrast of objects to their environment in certain image channels derived after the new segmentation. Based on what the user knows is normal and what is unusual, the image features for the outlier objects that are unusual are chosen as good candidates for further investigations taking more images and objects into account than just the outliers. The alternative segmentations that are first tested on the outlier objects can be selected by the user and picked from a library of algorithms.

Although the present invention has been described in connection with certain specific embodiments for instructional purposes, the present invention is not limited thereto. For example, although embodiments of the Cognition Program and computer-implemented network structure have been described above in relation to the computer-aided detection of breast cancer apparent in mammograms and esophagogastric cancer apparent on biopsy tissue cores, the Cognition Program and network structure can equally be applied to detecting and analyzing target patterns in digital imagery of geographical objects, military targets and weather patterns. The Cognition Program and network structure can be used to detect and analyze radar and sonar shadows of airplanes, ships, submarines and schools of fish. The Cognition Program and network structure can also be used to detect and analyze anatomical regions other than the human brain, breasts and esophagus. For example, the Cognition Program can be used to detect and analyze cancerous regions in human lungs. Accordingly, various modifications, adaptations, and combinations of various features of the described embodiments can be practiced without departing from the scope of the invention as set forth in the claims.

What is claimed is:

1. A method comprising:
generating a plurality of image objects by segmenting a digital image using object-oriented image analysis;
selecting selected image objects from among the plurality of image objects;
displaying one of the selected image objects on a graphical user interface;
determining a value of each of a subset of image features of the plurality of image objects, wherein the subset of image features constitutes a custom image-based biomarker;
calculating magnitudes of the custom image-based biomarker for each of the plurality of image objects; and
changing the image features included in the subset of image features such that magnitudes of the custom image-based biomarker for the selected image objects are greater than the magnitudes of the custom image-based biomarker for image objects other than the selected image objects.

2. The method of claim 1, further comprising:
searching a database of digital images for which magnitudes of the customer image-based biomarker have been calculated for image objects in the digital images and identifying identified digital images that include matched image objects for which the magnitudes of the custom image-based biomarker are greater than the magnitudes of the custom image-based biomarker for image objects in the identified digital images other than the matched image objects.

3. The method of claim 2, further comprising:
retrieving an indication of the medical condition of patients associated with the identified digital images.

4. The method of claim 2, further comprising:
displaying a list of the identified digital images.

5. The method of claim 1, wherein the calculating the magnitudes of the custom image-based biomarker involves weighting each value of each image feature of each subset and summing all of the weighted values of the image features in the subset.

6. The method of claim 1, wherein the digital image is a medical image of a patient.

7. The method of claim 1, wherein the selected image objects are manually selected by a clinical expert.

8. The method of claim 1, wherein the selected image objects are generated from within regions of interest in the digital image, and wherein the regions of interest depict cancerous tissue identified by a pathologist.

9. The method of claim 1, wherein the selected image objects correspond to human tissue taken from the group consisting of: tumor cells, lung cells and lymph nodes.

10. The method of claim 1, wherein the digital image is acquired by a computed tomography (CT) system.

11. The method of claim 1, wherein the digital image is acquired by a digital pathology slide scanner.

12. The method of claim 1, wherein the digital image depicts tissue stained using immunohistochemistry, and wherein antibodies are used to measure protein expression in the stained tissue.

13. The method of claim 1, wherein the digital image depicts tissue stained using fluorescence in situ hybridization (FISH), and wherein genetic markers are used to measure gene amplification in the tissue.

14. A method comprising:
generating image objects by segmenting first digital images of tissue using object-oriented image analysis, wherein the tissue is taken from a first patient;
determining a value of each of a first subset of image features of the image objects, wherein the image features of the first subset belong to a first custom biomarker;
calculating a magnitude of the first custom biomarker for each of the first digital images based on the values of the first subset of image features for the image objects in the first digital images; and
selecting a second subset of image features that belong to a second custom biomarker such that the magnitude of the second custom biomarker for each of the first digital images is greater than the magnitude of the first custom biomarker for each of the first digital images.

15. The method of claim 14, wherein the calculating the magnitude of the first custom biomarker involves weighting each value of each image feature of the first subset and summing all of the weighted values of the image features in the first subset.

16. The method of claim 14, further comprising:
modifying how the value of each image feature in the second subset is weighted such that the magnitude of the second custom biomarker for each of the first digital images increases.

17. The method of claim 14, further comprising:
searching a database of second digital images for which magnitudes of the second customer biomarker have been calculated and identifying matched digital images for which the magnitudes of the second custom biomarker are greater than the magnitudes of the second custom biomarker for the first digital images.

18. The method of claim 17, further comprising:
displaying a list of the matched digital images.

19. The method of claim 17, further comprising:
retrieving an indication of the medical condition of patients associated with the matched digital images.

20. The method of claim 14, further comprising:
saving the second custom biomarker on a computer-readable medium.

\* \* \* \* \*